US012678180B2

(12) United States Patent
Sirhan et al.

(10) Patent No.: US 12,678,180 B2
(45) Date of Patent: ***Jul. 14, 2026

(54) METHODS AND APPARATUS FOR PLAQUE DISRUPTION

(71) Applicant: Elixir Medical Corporation, Milpitas, CA (US)

(72) Inventors: Motasim Sirhan, Los Altos, CA (US); Benjamyn Serna, Gilroy, CA (US); Bozena Treadwell, Aptos, CA (US); John Yan, Los Gatos, CA (US)

(73) Assignee: Elixir Medical Corporation, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/655,102

(22) Filed: May 3, 2024

(65) Prior Publication Data

US 2024/0293131 A1     Sep. 5, 2024

Related U.S. Application Data

(63) Continuation of application No. 17/863,265, filed on Jul. 12, 2022, now Pat. No. 12,011,184, which is a
(Continued)

(51) Int. Cl.
*A61B 17/22*     (2006.01)
*A61F 2/24*     (2006.01)
(Continued)

(52) U.S. Cl.
CPC ............ *A61B 17/22* (2013.01); *A61F 2/2418* (2013.01); *A61F 2/2436* (2013.01);
(Continued)

(58) Field of Classification Search
CPC ........... A61B 2017/00783; A61B 2017/22001; A61B 2017/22051; A61B 2017/22061;
(Continued)

(56) References Cited

U.S. PATENT DOCUMENTS 4,944,745 A     7/1990 Sogard et al.
4,986,830 A     1/1991 Owens et al.
(Continued)

FOREIGN PATENT DOCUMENTS

AU          2020268374 A1     11/2021
CN          108452427 A     8/2018
(Continued)

OTHER PUBLICATIONS

PCT/US2022/022213 International Search Report and Written Opinion dated Jul. 18, 2022.
(Continued)

*Primary Examiner* — Kathleen S Holwerda
(74) *Attorney, Agent, or Firm* — Wilson Sonsini Goodrich & Rosati

(57)          ABSTRACT

Balloon catheters, sleeves, cages, and endoluminal prostheses are provided with stress-applying and spacing features coupled to expandable surfaces thereof. The stress-applying features may have blunt and/or rounded contact regions which contact tissue or calcified regions in the vasculature. The contact regions dent or fracture occlusive material on the wall of a vascular lumen and/or patient valve leaflets when expanded. The spacing features permit blood, drug, and contrast perfusion past structures expanded in the vasculature, particularly balloon catheters.

26 Claims, 33 Drawing Sheets

Related U.S. Application Data continuation of application No. PCT/US2022/022213, filed on Mar. 28, 2022, and a continuation-in-part of application No. 16/786,736, filed on Feb. 10, 2020, now Pat. No. 11,622,872.

(60) Provisional application No. 63/322,372, filed on Mar. 22, 2022, provisional application No. 63/287,813, filed on Dec. 9, 2021, provisional application No. 63/240,811, filed on Sep. 3, 2021, provisional application No. 63/200,794, filed on Mar. 29, 2021.

(51) Int. Cl.
*A61M 25/10* (2013.01)
*A61B 17/00* (2006.01)

(52) U.S. Cl.
CPC .............. *A61B 2017/00783* (2013.01); *A61B 2017/22001* (2013.01); *A61B 2017/22051* (2013.01); *A61B 2017/22098* (2013.01); *A61F 2250/006* (2013.01)

(58) Field of Classification Search
CPC .. A61B 2017/22098; A61B 17/320725; A61B 17/22; A61M 2025/1086
See application file for complete search history.

(56) References Cited

U.S. PATENT DOCUMENTS

| | | | |
|---|---|---|---|
| 5,087,247 A | 2/1992 | Horn et al. | |
| 5,102,402 A | 4/1992 | Dror et al. | |
| 5,196,024 A * | 3/1993 | Barath ........... | A61B 17/320725 |
| | | | 606/191 |
| 5,242,397 A | 9/1993 | Barath et al. | |
| 5,295,959 A | 3/1994 | Gurbel et al. | |
| 5,308,356 A | 5/1994 | Blackshear, Jr. et al. | |
| 5,383,856 A | 1/1995 | Bersin | |
| 5,395,333 A | 3/1995 | Brill | |
| 5,423,745 A | 6/1995 | Todd et al. | |
| 5,443,446 A | 8/1995 | Shturman | |
| 5,458,575 A | 10/1995 | Wang | |
| 5,545,132 A | 8/1996 | Fagan et al. | |
| 5,569,195 A | 10/1996 | Saab | |
| 5,591,129 A | 1/1997 | Shoup et al. | |
| 5,591,197 A | 1/1997 | Orth et al. | |
| 5,599,306 A | 2/1997 | Klein et al. | |
| 5,643,171 A | 7/1997 | Bradshaw et al. | |
| 5,653,690 A | 8/1997 | Booth et al. | |
| 5,893,840 A | 4/1999 | Hull et al. | |
| 6,047,700 A | 4/2000 | Eggers et al. | |
| 6,129,706 A | 10/2000 | Janacek | |
| 6,197,013 B1 | 3/2001 | Reed et al. | |
| 6,210,392 B1 | 4/2001 | Vigil et al. | |
| 6,234,952 B1 | 5/2001 | Liprie | |
| 6,450,988 B1 | 9/2002 | Bradshaw | |
| 7,070,576 B2 | 7/2006 | O'Brien et al. | |
| 7,413,558 B2 | 8/2008 | Kelley et al. | |
| 7,494,497 B2 | 2/2009 | Weber | |
| 7,632,288 B2 | 12/2009 | Wu | |
| 7,662,163 B2 | 2/2010 | Grayzel et al. | |
| 7,686,824 B2 | 3/2010 | Konstantino et al. | |
| 7,731,744 B1 | 6/2010 | Cox | |
| 7,799,043 B2 | 9/2010 | O'Brien et al. | |
| 7,803,168 B2 | 9/2010 | Gifford et al. | |
| 8,048,093 B2 | 11/2011 | Mapes et al. | |
| 8,052,703 B2 | 11/2011 | St et al. | |
| 8,080,026 B2 | 12/2011 | Konstantino et al. | |
| 8,092,470 B2 | 1/2012 | Miyamoto et al. | |
| 8,123,737 B2 | 2/2012 | Bertolero et al. | |
| 8,187,223 B2 | 5/2012 | Spargias | |
| 8,221,484 B2 | 7/2012 | Wesselmann | |
| 8,262,687 B2 | 9/2012 | Igaki | |
| 8,323,325 B2 | 12/2012 | Valencia | |

| | | | |
|---|---|---|---|
| 8,348,987 B2 | 1/2013 | Eaton | |
| 8,398,662 B2 | 3/2013 | Granada et al. | |
| 8,419,671 B2 | 4/2013 | Matheis et al. | |
| 8,454,636 B2 | 6/2013 | Konstantino et al. | |
| 8,523,887 B2 | 9/2013 | Grayzel et al. | |
| 8,632,559 B2 | 1/2014 | Gershony et al. | |
| 8,685,075 B2 | 4/2014 | Stoltze et al. | |
| 8,808,237 B2 | 8/2014 | Thielen et al. | |
| 8,876,882 B2 | 11/2014 | Barongan | |
| 8,882,790 B2 | 11/2014 | Kassab | |
| 8,992,553 B2 | 3/2015 | Diamant et al. | |
| 9,055,965 B2 | 6/2015 | Chang et al. | |
| 9,056,004 B2 | 6/2015 | Ginsburg et al. | |
| 9,119,944 B2 | 9/2015 | Chambers et al. | |
| 9,302,071 B2 | 4/2016 | Manderfeld et al. | |
| 9,339,291 B2 | 5/2016 | Aggerholm et al. | |
| 9,370,644 B2 | 6/2016 | Rocha-Singh | |
| 9,375,555 B2 | 6/2016 | Pedersen et al. | |
| 9,409,001 B2 | 8/2016 | Aggerholm et al. | |
| 9,504,807 B2 | 11/2016 | Drasler et al. | |
| 9,717,513 B2 | 8/2017 | Golan | |
| 9,724,121 B2 | 8/2017 | Hefer | |
| 9,808,276 B2 | 11/2017 | Silvestro | |
| 9,827,096 B2 | 11/2017 | Weber et al. | |
| 9,937,280 B2 | 4/2018 | Yan et al. | |
| 9,993,625 B2 | 6/2018 | Roth et al. | |
| 10,143,452 B2 | 12/2018 | Golan | |
| 10,182,841 B1 * | 1/2019 | Rousu ........... | A61B 17/320725 |
| 10,245,419 B2 | 4/2019 | Drasler et al. | |
| 10,292,849 B2 | 5/2019 | Boyle et al. | |
| 10,299,823 B2 | 5/2019 | Piccagli | |
| 10,300,257 B2 | 5/2019 | Wu et al. | |
| 10,342,962 B2 | 7/2019 | Gerrans et al. | |
| 10,471,238 B2 | 11/2019 | Schneider et al. | |
| 10,478,202 B2 | 11/2019 | Adams et al. | |
| 10,485,571 B2 | 11/2019 | Moffarah et al. | |
| 10,661,061 B2 | 5/2020 | Gerrans et al. | |
| 10,729,893 B2 | 8/2020 | Manderfeld et al. | |
| 10,758,255 B2 | 9/2020 | Adams | |
| 10,786,661 B2 | 9/2020 | Grace | |
| 10,881,426 B2 | 1/2021 | Bacino et al. | |
| 10,888,443 B2 | 1/2021 | Schneider et al. | |
| 10,980,553 B2 | 4/2021 | Or et al. | |
| 11,000,299 B2 | 5/2021 | Hawkins et al. | |
| 11,065,029 B2 | 7/2021 | McMAHON et al. | |
| 11,089,944 B2 | 8/2021 | Rentschler et al. | |
| 11,154,320 B2 | 10/2021 | Haverkost et al. | |
| 11,701,502 B2 | 7/2023 | Schneider et al. | |
| 12,011,184 B2 * | 6/2024 | Sirhan ................... | A61B 17/22 |
| 2001/0037146 A1 | 11/2001 | Lau et al. | |
| 2002/0010489 A1 * | 1/2002 | Grayzel ................. | A61F 2/958 |
| | | | 606/194 |
| 2003/0153870 A1 | 8/2003 | Meyer et al. | |
| 2004/0133223 A1 | 7/2004 | Weber | |
| 2005/0119678 A1 * | 6/2005 | O'Brien ......... | A61B 17/320725 |
| | | | 606/159 |
| 2005/0137621 A1 | 6/2005 | Stahl et al. | |
| 2006/0122684 A1 | 6/2006 | Lye et al. | |
| 2006/0129229 A1 | 6/2006 | Fukaya et al. | |
| 2006/0182873 A1 | 8/2006 | Klisch et al. | |
| 2006/0271161 A1 | 11/2006 | Meyer et al. | |
| 2007/0213761 A1 | 9/2007 | Murphy et al. | |
| 2008/0228139 A1 * | 9/2008 | Melsheimer ........ | A61M 25/104 |
| | | | 604/103.08 |
| 2009/0105687 A1 | 4/2009 | Deckman et al. | |
| 2009/0240270 A1 | 9/2009 | Schneider et al. | |
| 2011/0021985 A1 | 1/2011 | Spargias | |
| 2012/0116289 A1 | 5/2012 | Hawkins et al. | |
| 2012/0191111 A1 | 7/2012 | Aggerholm et al. | |
| 2013/0066257 A1 | 3/2013 | Folan et al. | |
| 2013/0150874 A1 | 6/2013 | Kassab | |
| 2013/0211381 A1 | 8/2013 | Feld | |
| 2014/0277562 A1 | 9/2014 | Seddon et al. | |
| 2015/0216552 A1 | 8/2015 | Hefer | |
| 2016/0067465 A1 | 3/2016 | Gerrans et al. | |
| 2016/0128718 A1 | 5/2016 | Aggerholm et al. | |
| 2017/0049997 A1 | 2/2017 | Chao et al. | |
| 2017/0106174 A1 | 4/2017 | Schneider et al. | |
| 2017/0333686 A1 * | 11/2017 | Schneider ............... | B29C 70/72 |

(56) References Cited

U.S. PATENT DOCUMENTS

| | | | |
|---|---|---|---|
| 2018/0304052 A1 | 10/2018 | Schneider et al. |
| 2019/0344054 A1 | 11/2019 | Slattery et al. |
| 2019/0350651 A1 | 11/2019 | Gifford, III et al. |
| 2020/0197033 A1 | 6/2020 | Pasquino et al. |
| 2020/0316350 A1 | 10/2020 | Patel |
| 2020/0323545 A1 | 10/2020 | Or et al. |
| 2021/0008354 A1 | 1/2021 | Bhamanyar |
| 2021/0378744 A1 | 12/2021 | Fanier et al. |
| 2021/0393281 A1 | 12/2021 | Golan |

FOREIGN PATENT DOCUMENTS

| | | | |
|---|---|---|---|
| CN | 111228633 | A | 6/2020 |
| CN | 211301685 | U | 8/2020 |
| CN | 112472228 | A | 3/2021 |
| CN | 110201289 | B | 9/2021 |
| EP | 0750919 | A2 | 1/1997 |
| EP | 0808613 | A1 | 11/1997 |
| EP | 1056518 | A1 | 12/2000 |
| EP | 1352672 | A2 | 10/2003 |
| EP | 2919707 | A1 | 9/2015 |
| EP | 1480709 | B1 | 10/2018 |
| JP | 2004504111 | A | 2/2004 |
| JP | 2007512873 | A | 5/2007 |
| JP | 2011515147 | A | 5/2011 |
| KR | 20200077682 | A | 7/2020 |
| WO | WO-9940971 | A1 | 8/1999 |
| WO | WO-2002007795 | A2 | 1/2002 |
| WO | WO-0226323 | A1 | 4/2002 |
| WO | WO-03084594 | A2 | 10/2003 |
| WO | WO-2005060840 | A1 | 7/2005 |
| WO | WO-2006124398 | A2 | 11/2006 |
| WO | WO-2009117158 | A2 | 9/2009 |
| WO | WO-2012040225 | A2 | 3/2012 |
| WO | WO-2013126779 | A1 | 8/2013 |
| WO | WO-2018204782 | A1 | 11/2018 |
| WO | WO-2019209696 | A1 | 10/2019 |
| WO | WO-2020014515 | A1 | 1/2020 |
| WO | WO-2021040675 | A1 | 3/2021 |
| WO | WO-2021046001 | A1 | 3/2021 |
| WO | WO-2021251963 | A1 | 12/2021 |
| WO | WO-2021251980 | A1 | 12/2021 |
| WO | WO-2022022223 | A1 | 2/2022 |
| WO | WO-2022212290 | A1 | 10/2022 |
| WO | WO-2024064843 | A2 | 3/2024 |

OTHER PUBLICATIONS

PCT/US2023/074810 International Search Report and Written Opinion dated Apr. 15, 2024.

U.S. Appl. No. 17/863,265 Notice of Allowance dated Mar. 26, 2024.

U.S. Appl. No. 17/863,265 Notice of Allowance dated May 16, 2024.

U.S. Appl. No. 17/863,265 Office Action dated Feb. 9, 2024.

U.S. Appl. No. 17/863,265 Office Action dated Jan. 13, 2023.

U.S. Appl. No. 17/863,265 Office Action dated Mar. 24, 2023.

U.S. Appl. No. 17/863,265 Office Action dated Nov. 16, 2023.

EP20220781978.6 Extended European Search Report dated Jan. 3, 2025.

JP2023-556767 Office Action dated Dec. 26, 2025.

* cited by examiner

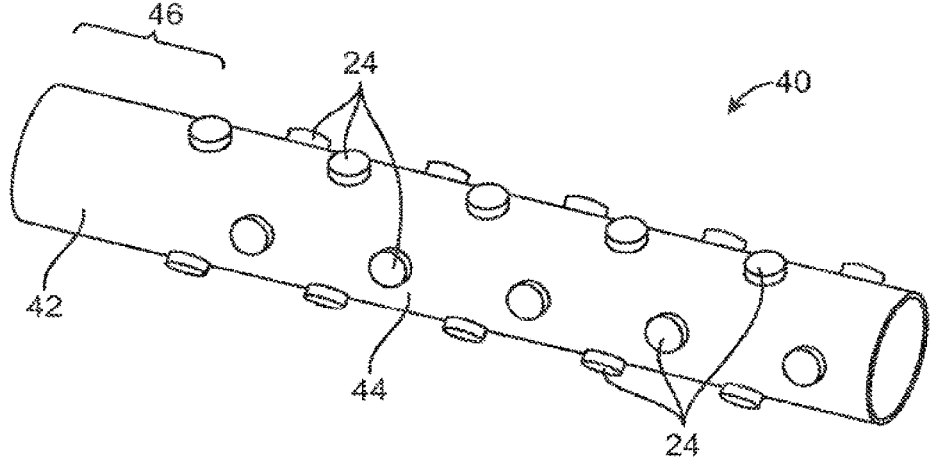
FIG. 3
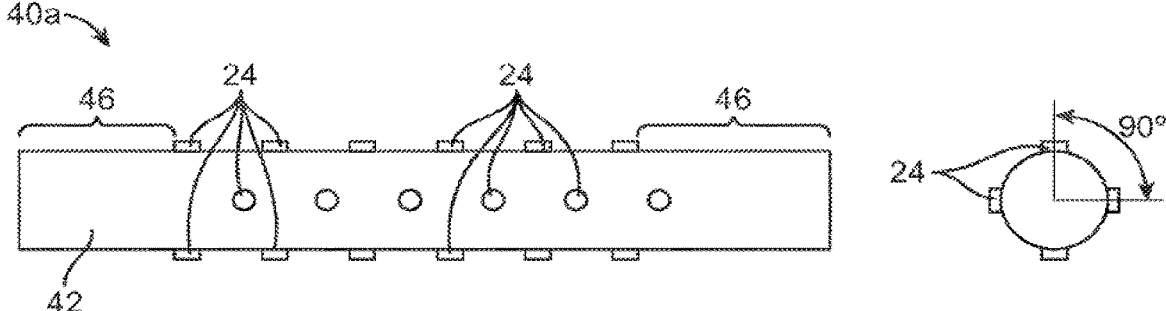
FIG. 4A
FIG. 4B
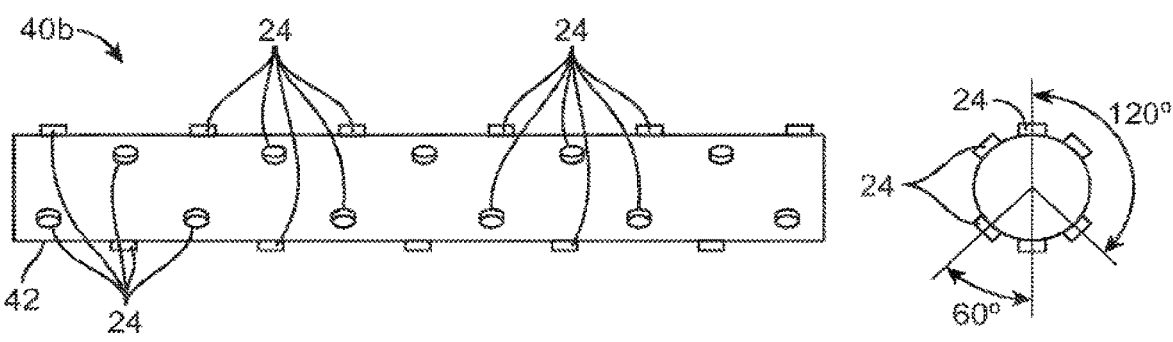
FIG. 5A
FIG. 5B

FIG. 14A                    FIG. 14B

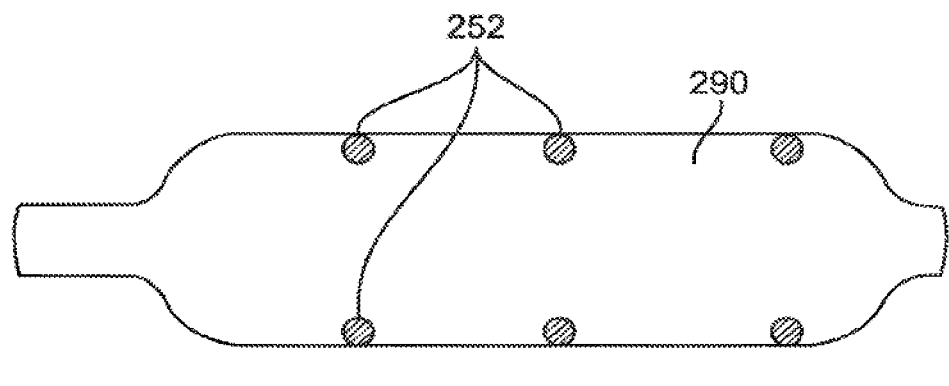
FIG. 18A
FIG. 18B
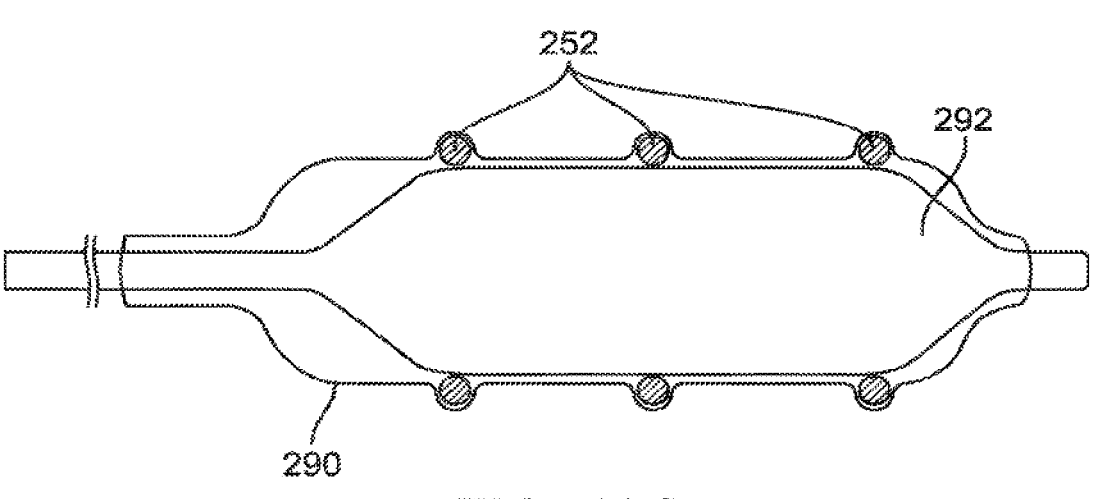
FIG. 18C

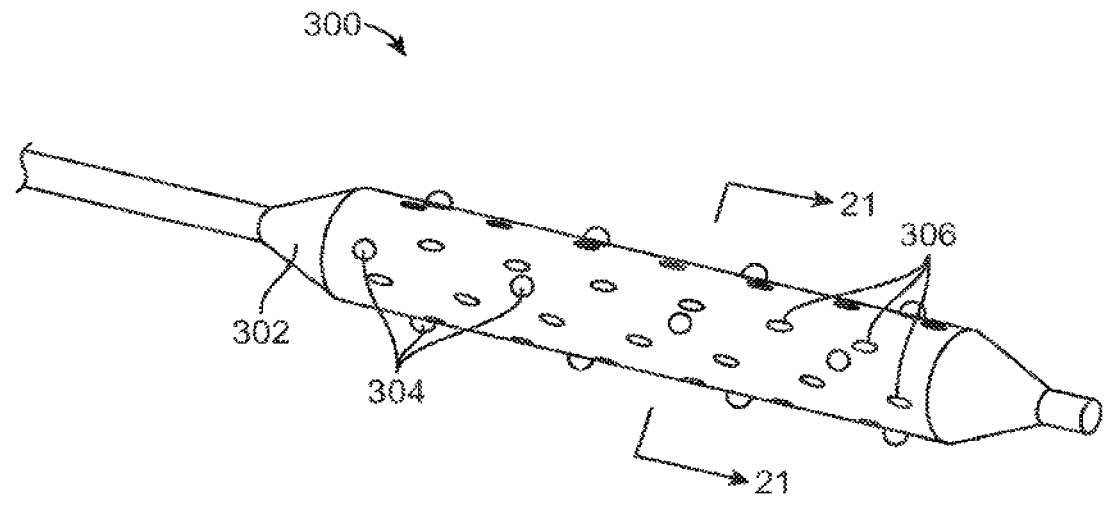
FIG. 19
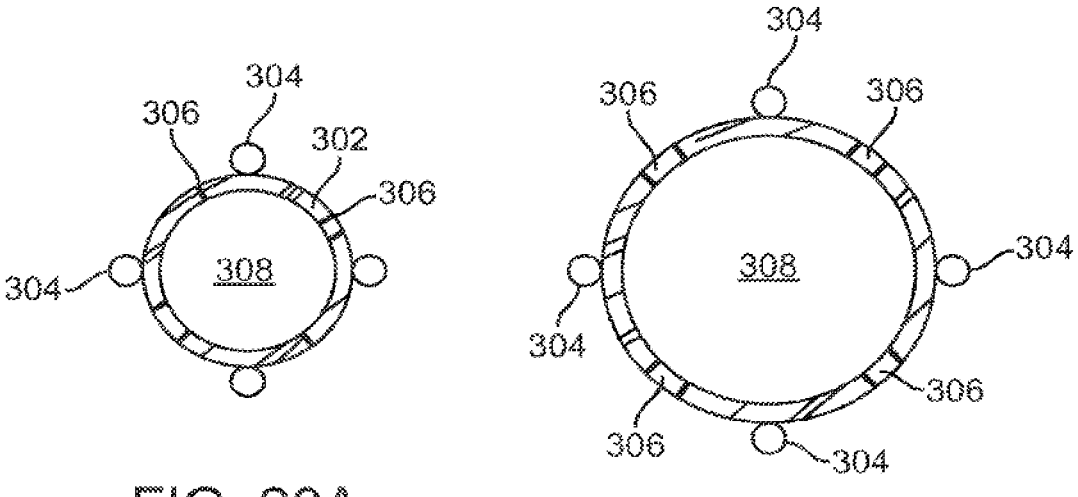
FIG. 20A
FIG. 20B

FIG. 24A                    FIG. 24B

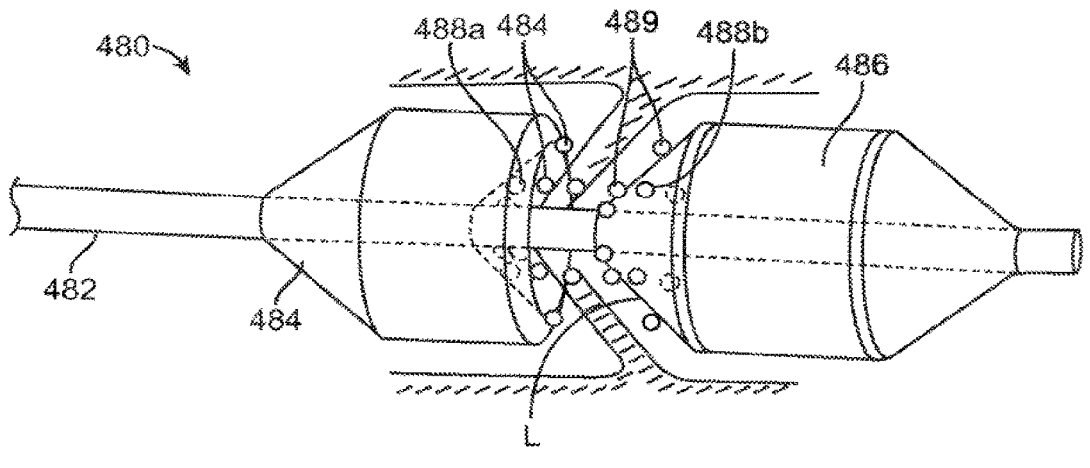
FIG. 30A
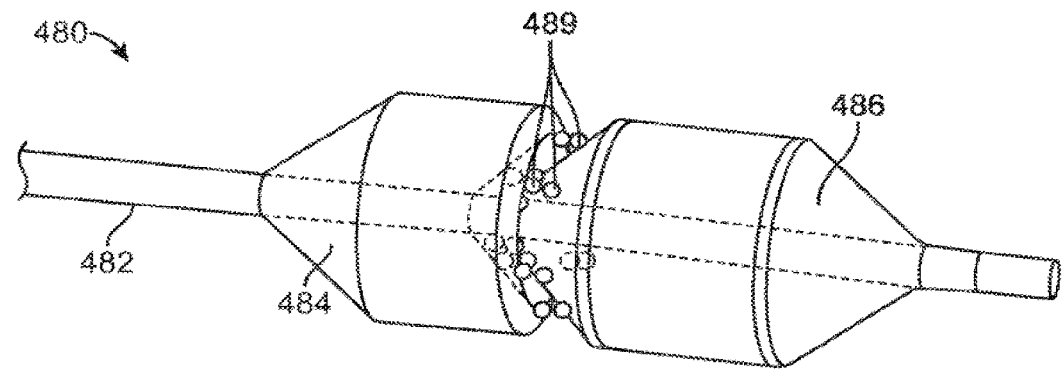
FIG. 30B
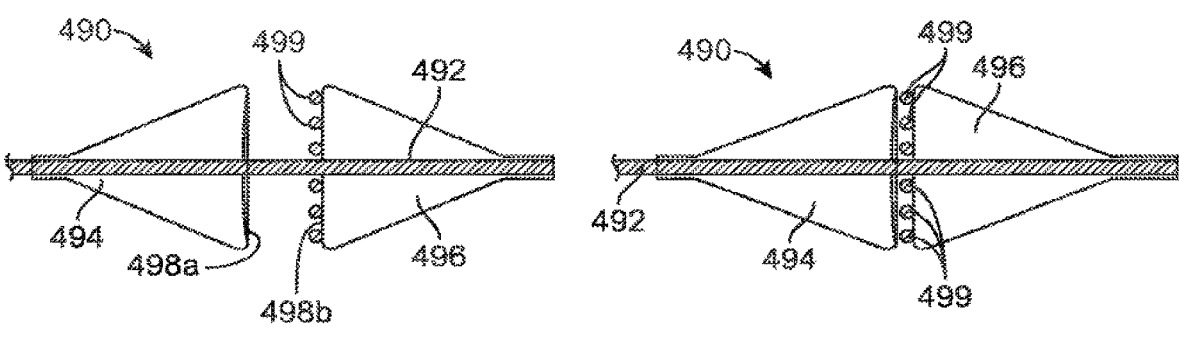
FIG. 31A                    FIG. 31B

METHODS AND APPARATUS FOR PLAQUE DISRUPTION

CROSS-REFERENCE TO RELATED APPLICATIONS

This application is a continuation of U.S. patent application Ser. No. 17/863,265, filed Jul. 12, 2022, which is a continuation-in-part of U.S. patent application Ser. No. 16/786,736, filed Feb. 10, 2020, the entire content of which is incorporated herein by reference; U.S. patent application Ser. No. 17/863,265, filed Jul. 12, 2022, is also a continuation of PCT Application No. PCT/US22/22213, filed Mar. 28, 2022, which claims the benefit of provisional application 63/322,372, filed on Mar. 22, 2022, of 63/287,813, filed on Dec. 9, 2021, of provisional application 63/240,811, filed on Sep. 3, 2021, and of provisional application 63/200,794, filed on Mar. 29, 2021, the full disclosures of which are incorporated herein by reference.

BACKGROUND OF THE INVENTION

1. Field of the Invention

The present invention relates generally to medical devices and methods. More particularly, the present invention relates to devices comprising or consisting of expandable structures, including vascular devices, vascular catheters, expandable sleeves, expandable cages, balloon catheters, scaffolds, stents, vascular grafts, implantable vascular prostheses configured to open, expand, delivery drugs, and/or fracture calcified and/or hardened lesions in a blood vessel and/or valve, and/or body lumen.

Balloons, cages, stents, grafts, and other prostheses and devices are commonly used to provide or maintain patency in blood vessels and heart and venous valve structures which have been narrowed by lesions or other disease conditions. In cases where the lesion is hardened by plaque, calcium, and the like, a "cutting balloon" may be used for the initial treatment step to break the plaque and calcifications to permit the balloon to widen the lesion prior to stent placement. Optionally, a stent may be post-dilated using a non-compliant angioplasty balloon to ensure good apposition to the blood vessel wall. The post-dilation balloon is taken to higher atmospheric pressures using a balloon inflation device. Stenting after angioplasty with a cutting balloon, however, can be problematic in several respects, particularly when followed by post dilation at higher pressures. In some instances, the blood vessel wall can be injured, or such injury propagates. In others, debris generated by the cutting balloon can be released as emboli.

The use of cutting balloons, cutting cages, and cutting stents has been proposed for disrupting vascular calcifications with various issues including being less deliverable, tend to be bulky limiting access, or patient injury. The cutting stent was proposed to be used in a "primary stenting" procedure without use of a pre-dilation angioplasty balloon to widen the area to be stented. Primary stenting reduces or eliminates the need to perform two or three sequential interventions, which in turn reduces the risk of vessel injury and emboli release as discussed above. However, cutting stents have similar limitation of being bulky, cause injury, and are less deliverable.

Heart and venous valve function can be adversely affected by the presence of calcifications on the valve leaflets. Valvuloplasty procedures rely on disrupting the lesions by expanding a balloon inside of the opposed leaflet surfaces in order to crack the calcifications. The use of cutting and caged balloons for enhancing such valvuloplasty procedures has been proposed but has not found widespread use as it increases the risk of damaging the valve and/or the valve function.

While a significant potential improvement in many instances, such cutting balloons, cages, and stents typically employ sharpened blades which are oriented radially outwardly and present a risk of injury to the patient.

In addition, cutting blades can make a device bulky and less deliverable, often limiting access to distal vessel regions. Cutting blades also tend to rupture the blood vessel wall beneath calcified/hardened plaque lesions, particularly at higher inflation pressures, which may cause patient injury.

Another challenge in performing angioplasty and valvuloplasty procedures is the temporary blockage of the of the vessel lumen or valve annulus by balloon expansion. While temporary blockage of blood flow is often acceptable, a more serious concern can be the loss of contrast medium flow downstream of the balloon. Even a short loss of contrast medium can make fluoroscopic imaging of the procedure more difficult. While a variety of perfusion catheters have been proposed, they often require an additional flow lumen through the balloon, making the catheter larger and less useful in many circumstances.

For these reasons, it would be desirable to provide improved methods and apparatus for opening, expanding, delivering drugs, improved visualization, and/or treating calcified or hardened lesions with a reduced risk to the patient and equivalent or improved efficacy in treating the calcifications or hardened lesions. The improvements would preferably apply to a wide variety of vascular and cardiac devices, including expandable structures, such as vascular catheters, expandable sleeves, expandable cages, balloon catheters, stents, implantable vascular prostheses, drug delivery devices, others, and the like. It would be still further desirable if the devices and procedure could improve the perfusion of both blood and/or contrast medium during the procedure. At least some of these advantages will be provided by the present invention.

2. Listing of Background Art

Patents and printed publications describing different types of plaque disruptive and other features on various supporting structures include: US2009/0105687; US2006/0129229; US2005/0137621; U.S. Pat. Nos. 9,370,644; 9,119,944; 8,992,553; 8,882,790; 8,523,887; 8,323,325; 7,799,043; 6,197,013; 5,242,397; and EP2919707; Patents and printed publications describing expandable scaffolds having plaque disruptive and other features include: U.S. Pat. Nos. 8,876,882; 7,494,497; 9,724,121; 7,731,744; 5,591,197; US2006/122684; US2014/277562; US2001/037146; US2006/271161; US2020/0323545; U.S. Ser. No. 10/143,452; U.S. Pat. Nos. 9,717,513; 8,398,662; 8,092,470; 8,080,026; 7,803,168; 6,047,700; 5,443,446; and Patents and printed publications describing multiple surface valvuloplasty include: US2021/0378744; U.S. Ser. No. 11/000,299; U.S. Ser. No. 10/758,255; U.S. Ser. No. 10/478,202; U.S. Pat. Nos. 9,827,096; 8,187,223; US20210393281; US20200197033; U.S. Ser. No. 11/000,299; U.S. Ser. No. 10/980,553; U.S. Ser. No. 10/342,962; U.S. Ser. No. 10/245,419; U.S. Pat. Nos. 9,504,807; 9,375,555; 4,986,830; EP13526772; EP1480709; KR20200077682; WO2020014515; WO2012040225; WO2003/084594; and WO2013126779.

SUMMARY OF THE INVENTION

Devices according to the present invention comprise stress-applying features or force-applying features which may have any one of a variety of specific designs and geometries selected to fracture, dent, or otherwise disrupt regions of calcified or otherwise hardened plaque, expand, deliver drugs, improve visualization, and/or enlarge lesions in a patient's vasculature with low to minimum risk to underlying patient tissue. The devices of the present invention will often find use in angioplasty, stent placement, drug delivery, enhanced visualization, and other interventions in the arterial or venous vasculature. In addition, the devices of the present invention will find use in treating or modifying cardiac and venous valve structures, for example in performing valvuloplasty procedures in a patient's aortic valve.

The stress-applying and force-applying features of the present invention are also referred to herein as plaque-disrupting features, plaque-engaging features, calcium-engaging features, and these terms will be used interchangeably herein and in the claims. Other suitable descriptors for these features include plaque-denting features, and stress-inducing features, and unless otherwise stated, these terms and phrases will be used interchangeably. The stress-applying features of the present invention may have any one of a variety of designs as described in this invention.

A first type of stress-applying features will typically comprise a blunt contact region configured to engage the plaque or other hardened or calcified material to expand, fracture, dent, otherwise disrupt that material while minimizing risk to underlying tissue or vascular wall, the valve annulus, or other patient tissue which would be at risk if pressure will be applied by a blade or other sharpened structure. A variety of specific designs for the stress-applying features of the present invention are described below, including discs, plates, balls, spheres, hemispheres, partial spheres, ellipsoidal solids, oblong, other, and the like. The stress-applying features may be solid or comprise a hollow interior. The stress-applying features of the present invention may be (1) pre-formed and attached to the device such as balloon, a sleeve, a stent, or a cage or (2) fabricated as in integral part or component part of a balloon, a sleeve, a stent, or a cage, as described in more detail in the present invention, or (3) a combination of (1) and (2).

The devices of the present invention will usually further comprise an apparatus or structure for radially advancing or deploying the stress-applying features within a patient target site, such as a blood vessel, valve annulus, or other body lumen or cavity. In some instances, pre-formed stress-applying features may be directly attached or coupled to an outer surface of any one of a variety of expandable structures, such as balloons, stents/scaffolds, stents, cages, sleeves, valve prostheses, valvuloplasty balloon catheters, and the like. In other instances, stress-applying features may be fabricated directly as an integrated part of such expandable structure. In still other instances, the stress-applying features may be attached to or fabricated as part of an intermediate structure which, while itself not being configured to expand, may be placed over a separate expandable structure. For example, the stress-applying features of the present invention may be attached to or formed as a part of sleeves, sheaths, covers, meshes, or other supporting structures which may be placed to surround or otherwise be supported by an expandable structure, such as an elastic sleeve being placed over an expandable balloon.

Exemplary stress-applying features of the present invention will have a circumscribed "footprint," or base typically having a maximum length, width, diameter, or other dimension of 4 mm or less, often being 3 mm or less, more often being no more than 1 mm, and frequently being no more than 0.75 mm, and sometimes being no more than 0.5 mm, or being no more than 0.25 mm. In another example, the base of the stress-applying features have a length, width, diameter, or configuration ranging from 0.1 mm to 4 mm, preferably ranging from 0.2 mm to 2 mm, more preferably ranging from 0.3 mm to 0.75 mm. Footprint refers to the maximum coverage area dimension of a stress-applying feature at the base over an underlying support surface, such as an outer surface of balloon, sleeve, scaffold, cage, or stent. The contact region or coverage area dimension of the stress-applying feature may be equal to that of the base, such as in the case of discs, balls, spheres, or may be greater than that of the base when the feature tapers radially outwardly as in the case of inverted cones or inverted hemispheres, or inverted partial-spheres, or may be smaller than that of the base when the feature tapers radially outwardly as in the case of cones, hemisphere, or partial-spheres. In one example, the contact region of the stress-applying features have a length, width, diameter, or configuration ranging from 0.01 mm to 4 mm, preferably ranging from 0.1 mm to 2 mm, more preferably ranging from 0.1 mm to 0.75 mm. In another example, the stress-applying features are spheres, or the like, wherein the contact region and/or base have a length, width, diameter, or configuration ranging from zero or near zero to 0.1 mm, more often ranging from 0.001 to 0.1 mm. The stress-applying features of the present invention will typically not be axially extended elongated members, such as blades, or similar elongate cutters, but rather have a circumferential elongation or configuration and axial elongation or configurations being about the same. In a preferred example, the footprint at the base of the stress-applying features has a maximum axial length to maximum circumferential width ranges from 0.5:1 to 1:0.5, more preferably ranges from 0.75:1 to 1:0.75, and most preferably about 1:1. In another preferred example, the dimensions at the base of the stress-applying features are substantially the same as the dimensions of the contact coverage area dimensions, as in the case of balls, hemisphere, partial sphere, spheres, or square for example.

Exemplary stress-applying features of the present invention will also typically have a height measured from the base attached to the supporting surface or substrate to the contact coverage area (contact region), typically being at least 0.05 mm, 0.1 mm, 0.15 mm, 0.2 mm, 0.25 mm, or more, and often not exceeding 1 mm, 0.5 mm, 0.4 mm, 0.3 mm, 0.25 mm, 0.15 mm, 0.1 mm or less, including all ranges between the minimum and maximum recited heights. In a preferred example, the height of the features ranges from 0.1 mm to 1 mm, preferably ranges from 0.2 mm to 0.75 mm, and more preferably ranges from 0.25 to 0.5 mm. The features may have the same height along the entire structure or different heights along the circumference and/or axial length of the substrate.

In a preferred example, the stress-applying features are discrete features to enhance flexibility and deliverability of the device in a patient vasculature or body lumen. Such discrete stress-applying features will typically be distributed over an expandable surface at a density when inflated or otherwise expanded of from 0.1 to 20 features/mm², preferably 0.1 to 5 features/mm², more preferably from 0.2 to 4 features/mm², more preferably from 0.25 to 3 features/mm².

In a preferred example, the stress-applying features are discrete, independent, and/or separated from one another features to enhance flexibility and deliverability of the device in a patient vasculature or body lumen. Such stress-applying features will typically be distributed over an expandable surface at a density when inflated or otherwise expanded from 0.1 to 20 features/mm$^2$, preferably 0.1 to 5 features/mm$^2$, more preferably from 0.2 to 4 features/mm$^2$, more preferably from 0.25 to 3 features/mm$^2$. In a preferred example, each of the features apply an independent or focal force to the plaque, vessel wall, tissue, hardened plaque, or calcified lesion.

In a preferred example, the stress-applying features are discrete, wherein each of the features contact region, body, and/or base are dull, rounded, smooth, and/or atraumatic, to enhance flexibility and deliverability of the device in a patient vasculature or body lumen. Such stress-applying features will typically be distributed over an expandable surface at a density when inflated or otherwise expanded ranging from 0.1 to 100 features/mm$^2$, preferably ranging from 0.1 to 20 features/mm$^2$, more preferably ranging from 0.1 to 5 features/mm$^2$, or in some instances ranging from 0.2 to 4 features/mm$^2$, more preferably ranging from 0.25 to 3 features/mm$^2$. In another example, the features shape comprising the contact region, base, and body, are rounded, dull, and atraumatic, to enhance flexibility and deliverability of the device in a patient vasculature or body lumen, while being able to disrupt, dent, or expand a hardened and/or calcified plaque.

In yet another example, the stress-applying features are coated with one or more material to provide roundness, smooth surface, dullness, and/or atraumatic surface, to enhance flexibility and deliverability of the device in a patient vasculature or body lumen, while being able to disrupt, dent, or expand a hardened and/or calcified plaque. In a preferred example, the material comprises one or more of metallic material, ceramic material, polymeric material, adhesive material, hydrophilic material, or other. The material is deposited, soldered, coated, plated, dipped, or otherwise applied to the surface of the stress-applying features. The material may be degradable or non-degradable in physiologic environment. In yet another instance, the coating material provides further attachment means of the stress—applying features to the expandable structure surface, wherein the coating covers the features and a portion of the expandable structure surface adjacent to the feature.

In preferred examples, at least most of, and preferably all of, the surface of the stress-applying feature which is exposed above the outer surface of the expandable member or other supporting surface will be rounded free from irregularities and imperfections that might inhibit advancement though a target body lumen and will typically be configured to present low friction smoothed surfaces free from edges to the walls of the vasculature or other body lumen as the expandable structure is advanced therethrough. By "at least most of" it is meant that at least 50%, preferably at least 60%, more preferably at least 70%, still more preferably at least 80%, and most preferably at least 90% of the exposed surface of the stress-applying feature will be rounded, smoothed, free from edges, or otherwise configured to present low friction. It has been found by the inventors herein that such smoothed, rounded features will still be able provide the force necessary to dent/disrupt even hardened plaque when deployed as described herein.

Pre-formed stress-applying features according to the present invention may be attached to an expandable structure, e.g. a balloon, or intermediate structure, e.g. a scaffold or sleeve or cage, by one or more of soldering, use of an adhesive (gluing), heat bonding, fusing, welding, threaded attachment, riveting, crimping, press fit, other, and the like.

Stress-applying features formed integrally as part of the balloon, scaffold, stent, cage, or sleeve may at a late or final process or location, e.g. by molding, a deposition process to build-up a structure on the outer surface of the scaffold, balloon, or sleeve or, in a preferred alternative, may be formed as a tab or other element projecting from a component of the scaffold, such as a crown, strut, or link, and folded over the outer surface of the component after forming scaffold but before implantation. Specific examples of such features are described in more detail as appurtenant features in the present invention. Pre-formed stress-applying features according to the present invention may be attached to an expandable structure, e.g. a balloon, or intermediate structure, e.g. a scaffold or sleeve or cage, by one or more of soldering, use of an adhesive (gluing), heat bonding, fusing, welding, threaded attachment, riveting, crimping, press fit, other, and the like. Stress-applying features formed integrally as part of the balloon, scaffold, stent, cage, or sleeve may at a late or final process or location, e.g. by molding, a deposition process to build-up a structure on the outer surface of the scaffold, balloon, or sleeve or, in a preferred alternative, may be formed as a tab or other element projecting from a component of the scaffold, such as a crown, strut, or link, and folded over the outer surface of the component after forming scaffold but before implantation. Specific examples of such features are described in more detail as appurtenant features in the present invention In a preferred example, the expandable structure comprises one of the following: a balloon surfaces, a stent surfaces, a sleeve surfaces, a cage surfaces, or a drug delivery surfaces. The stress-applying features may be applied to at least one of the expandable structure surfaces, wherein the surfaces comprise outer surface, inner surface, side surface of the expandable structure. In one example, the features may be applied to one or more of the following: outer surface of the balloon, working length of the balloon, taper of the balloon, side of the balloon, inner surface of the balloon, outer surface of a sleeve, outer surface of a cage, outer surface of a stent, inner surface of a sleeve, inner surface of a cage, or other surfaces. When the features are applied to an inner surface of an expandable structure, the features protrude radially outwardly to engage the hardened plaque upon expansion or inflation of the expandable structure.

In particular instances, the stress-applying features may be affixed to an expandable structure at least partially to an outer surface of one or more elements of, for example, a scaffold ring such as on a crown and/or strut. Such features can also be affixed at least partially to a link where the link connects two adjacent rings of the scaffold. The stress-applying feature can be formed from the same material or from a different material or materials from the scaffold. The stress-applying features can be 3D printed (deposited) or be laser cut from a tube, either separately from the scaffold fabrication or as part of the scaffold fabrication. In either case, the stress-applying feature protrudes radially outwardly from a scaffold element, such as crown, strut, or link. The stress-applying features may be formed as part of the scaffold and positioned in place after forming and before implantation, e.g. fixed by solder, welding, adhesive (such as an epoxy), press fit, mechanical fit, tying or other technique as described previously, where the stress-applying feature may be fixed or attached to the outer surface of the scaffold or optionally be positioned in a recess, hole or other receptacle formed in or through the outer surface the scaffold.

Affixing the stress-applying feature comprises one or more of coating, adhesive, fusing, solder, welding, vapor or chemical deposition, laser deposition, constriction with a sleeve, press fit or mechanical lock onto the scaffold outer surface (onto an indented scaffold surface, a recess, or a hole through the scaffold where portion of the stress-applying feature is forced into or through), epoxy, or combination thereof, or other.

The scaffold can be formed from a degradable material or a non-degradable material. In a preferred example, the scaffold formed from a metal or metal alloy or other non-degradable material having a Mohs hardness of 2.5 or greater, preferably 3.5 or greater, and more preferably 4.5 or greater. In a preferred example, the stress-applying feature will have a Mohs hardness equal to or greater than the Mohs hardness of the scaffold or other expandable structure. In other preferred example, the stress-applying feature will have a Mohs hardness greater than the Mohs hardness of the scaffold or other expandable structure. For example, the stress-applying features may be formed from material to have a Mohs hardness in a range from 2 to 10, usually from 2.5 to 10, more usually from 3 to 10, 3.5 to 10, 4 to 10, 4.5 to 10, 5 to 10, 5.5 to 10, 6 to 10, or 6.5 to 10.

In a preferred example, the expandable structure comprises stress-inducing features having a Mohs hardness of 2.5 or greater, preferably 3.5 or greater, and more preferably 4.5 or greater, often 5.5 or greater, and most preferably 6.5 or greater. In yet another example, the stress inducing features have a Mohs hardness ranging from 2 to 9, preferably ranging from 3 to 9, more preferably ranging from 4 to 9. In yet another example, the Mohs hardness of the stress-applying features will be greater than the Mohs hardness of the expandable structure supporting said features.

In a preferred example, the stress-applying features, spacer features, and all other protruding features and elements as described herein comprise at least one material from the following list: metallic, polymeric, ceramic, glass, metal alloy, or the like. The at least one material may be coated with another material. For example, a stainless-steel hemisphere may be coated with an adhesive and/or a polymeric material, wherein the adhesive and/or polymeric material has a Mohs hardness that is less than the Mohs hardness of the stainless-steel hemisphere. In a preferred example, the stress-applying features comprise a metal or other hard core as disclosed above covered partially or fully by a coating where the coating preferably has a Mohs hardness less than the Mohs hardness of the core. The softer coating can provide any one of roundness, dullness, lubricity, smoothness, and the like without sacrificing the stress-applying feature's ability to dent or fracture hardened plaque. In yet another example, the Mohs hardness of the stress-applying features will be at least two times greater than the Mohs hardness of the expandable structure supporting said features. In a preferred example, the expandable structure comprises or consists of polymeric material, while the stress-inducing features comprise or consist of metal or metal alloy material.

In further preferred examples, the stress-applying features, spacer features, and all other protruding features and elements as described will possess some degree of radiopacity to assist in viewing under fluoroscopy, either inherently as is the case with many metals, as a result of as combining or coating with a radiopaque material or filler, or both. Suitable radiopaque fillers suitable for combination with polymers include barium salts and iodine salts. Metals having a high radiopacity suitable for coating or plating metal and non-metal features include bismuth, gold, tungsten, and silver.

In other examples, the core may be polymeric and be coated with a metallic coating having a Mohs hardness larger than a Mohs hardness of the polymeric feature. Specific combinations of a core Mohs hardness and a coating Mohs hardness may be selected to provide sufficient force to dent, disrupt, or otherwise expand a hardened or calcified tissue or lesion, while being sufficiently flexible and smooth to be safely advanced through the vasculature or other anatomy.

When layering or mixing of multiple adhesives, one adhesive material may be softer than an adjacent material. Alternatively or additionally, a first adhesive material may more compatible with the material of the expandable member and be layered directly over the member surface, while one or more additional materials may be layer over the first layer to provide bonding to the stress-applying feature or other propertied to enhance the overall bonding of the stress-applying feature to the expandable member.

The material(s) of the stress-applying features are typically selected and configured to compress by 0.2 mm or less, by 0.1 mm or less, by 0.05 mm or less, and/or by 0.01 mm or less, when deployed against calcified or other plaque by a balloon, sleeve, or other expandable member. In other words, the material compressibility against a hard surface when pressurized through an expandable structure range from 0.001 mm to 0.2 mm, preferably from 0.001 mm to 0.1 mm, and more preferably from 0.001 mm to 0.01 mm. In other examples, the stress-applying feature has a material compressibility which is less than the compliance of the material of the expandable member when pressurized to a nominal inflation pressure.

The stress-applying features in another example have a fracture toughness of at least 10 $MPa \cdot m^{1/2}$, preferably at least 20 $MPa \cdot m^{1/2}$, more preferably at least 50 $MPa \cdot m^{1/2}$, and most preferably at least 100 $MPa \cdot m^{1/2}$. In a preferred example, the stress applying features have a Moh's hardness being greater than 4 and a fracture toughness being greater than 50 $MPa \cdot m^{1/2}$. In a preferred example, the stress applying features consist of a metal or metal alloy. In a preferred example, the stress applying features consist of or comprises a radiopaque material that provides radiopacity under x-ray/fluoroscopy. In yet another example, the stress applying features consist of or comprises a radiopaque material configured to provide radiopacity sufficient to visualize the features under fluoroscopy, preferably sufficient to visualize the features under fluoroscopy without the aid of radiopaque contrast material. In yet another preferred example, the stress applying features are attached to an expandable balloon catheter outer surface wherein the features consist of or comprises a radiopaque material configured to provide radiopacity sufficient to visualize the features under fluoroscopy, wherein the visualization is equal to or greater than the visualization of the contrast filled balloon under fluoroscopy. These advantages provide accurate sizing of the vessel, enhanced boundaries definition of the expandable structure such as an expanded/inflated balloon, and/or provides enhanced detection of hardened plaque or plaque morphology.

The stress-applying features of the present invention present a generally rounded, dull, and atraumatic structure above the surface of the expandable structure to facilitate advancement through the vasculature while still providing the force necessary to dent/disrupt the hardened plaque when expanded by the expandable member. This is advantageous as many of the cutting features of the prior art are sharp and would catch on the vasculature as the catheters are being advanced. Thus, in preferred examples of the present invention, at least the entire surface above the substrate and sometimes including the feature surface attached to the substrate) is rounded, smooth, and presents minimal friction as it is advanced.

The stress-applying features of the present invention in another example present a generally rounded, dull, free from peripheral edges, and atraumatic structure above the surface of the expandable structure to facilitate advancement through the vasculature while still providing the force necessary to dent/disrupt the hardened plaque when expanded by the expandable member. The stress-applying features of the present invention in another example present a generally rounded, dull, free from peripheral edges, free from rounded (beveled) peripheral edges, and atraumatic structure above the surface of the expandable structure to facilitate advancement through the vasculature while still providing the force necessary to dent/disrupt the hardened plaque when expanded by the expandable member. The plaque disrupting features in yet another example may have a peripheral edge or a rounded (beveled) peripheral edge. However, in a preferred example, the plaque disruption features are free from a peripheral edge. In yet another preferred example, the plaque disruption features are free from a peripheral edge or peripheral beveled edge.

In some instances, the stress-applying features of the present invention may comprise a sharp or potentially traumatic core which is covered by or coated with another material that provides a rounded, dull, or otherwise atraumatic engagement surface to avoid injury to the vasculature or other body lumen at the expandable member is advanced therethrough. In such instances, at least the potentially injurious contact regions of the features is covered or coated.

The expandable structure such as a balloon or scaffold can have any one of various shapes or configurations comprising one or more of cylindrical, substantially cylindrical, hourglass, dog bone, tapered, elliptical, oblong, or other shape, exterior shape, profile, or configuration. In many instances, the balloon, sleeve, cage, or scaffold will be expandable from a crimped or small configuration to a deployed or larger configuration by applying an interior expansion force, usually by fluid or balloon expansion as commonly employed for vascular devices and stents. Alternatively, the scaffold can be constrained and deployed from the constrained configuration by removing or withdrawing the constraint. Constraint may be provided by a catheter, a sleeve, a sheath, or other conventional or novel constraining structures. Such designs are commonly referred to as "self-expanding."

The stress-applying features can be formed from one or more of a metal, a metal alloy, a ceramic, a mineral, a polymer, a polymer blend, a mixture of polymers, an epoxy, a diamond, or combination thereof, including both degradable and non-degradable materials. Suitable metals and metal alloys include stainless steel, cobalt chrome, platinum chromium, silver, nickel-titanium alloy (NiTi), tungsten, tungsten carbide, palladium, cobalt, gold, platinum, titanium, carbide, titanium carbide, zirconium, chromium, magnesium or magnesium alloys such as magnesium-zinc and magnesium yttrium, zinc or zinc alloys such as zinc-calcium and zinc-lithium, and the like. In a specific example, which is particularly useful when place over balloons and sleeves, a chrome-plated steel ball may be used which is corrosion resistant and harder than an underlying metal, typically having a hardness comparable to that of a solid chromium ball.

In some examples, the plaque disrupting features comprise one or more material coating, covering, plated, or otherwise attached to one or more of features contact region, feature base, and/or features outer surface. In a preferred example, the material provides one or more of round, dull, smoothness, slipperiness, less friction, convexity, atraumatic surface, and/or lubricity to the surface of the feature, base, or contact region. In some examples, the material is polymeric comprising one or more of Poly-Para-Xylylene such as Parylene, Parylene N, and Parylene C, silicone such as polydimethylsiloxane, poly(diphenyl)siloxane, poly(methyl-co-phenyl)siloxane, poly(methyltrifluoropropyl) siloxane, poly(methyl-co-methyltrifluoropropyl) siloxane, or the like, polyurethanes and their copolymers such as tecoflex, pellathane, chronoflex, chronoprene, chronothane, chronosil, polyblend, or the like, polyethylene-vinyl acetate, polyvinylidene fluoride, polyvinylidene fluoride-co-hexafluoropropylene, polybutylmethacrylate, poly(styrene-butadiene-styrene), poly-lactide, hydrophilic material, or the like, or combinations thereof. Metal or metal alloy examples to coat providing hard or harder surface yet smooth, rounded, convex, and/or dull, applied to for example a polymeric features by evaporative, sputtering, vapor deposition, or plasma coating to the surface of the feature using a metal or alloy such as titanium, Ti-6Al-4V alloy, titanium-magnesium, stainless steel such as 316, 304, 420, or the like, magnesium alloys such as yttrium-zirconium-magnesium, chromium, cobalt, cobalt-chrome, CoCrMo, nitinol, tungsten, gold, platinum, silver, zinc, palladium, iridium, ruthenium, rhodium, indium, tin, molybdenum, iron, vanadium, nickel, niobium, zirconium, or the like, or combination thereof. Examples of polymeric features hardened by fillings of fine glass, quartz or silica fibers or particles such as 40% glass-filled Nylon, carbon fibers, carbon nanospheres, carbon nanotubes, carbon nanofibers, carbon nanotubes, talc, aramid or the like, are another example.

In a preferred example, adhesives are used to attach, secure, couple, and/or bond the feature or feature base the expandable structure surface. Examples include but not limited to one or more of light-cured materials such as Henkel Loctite 3943, 3973, 3972, 3321, 3311, 3526, Permabond UV610, UV670, UB7141, or the like, epoxy such as 5 min epoxy, Epo-tek MED-353ND, Epo-tek MED-HYB-353ND, Masterbond EP41SMed, Henkel Loctite 3981, polyurethanes such as Permabond PT321, PT326, and PT328, epoxy-polyurethane blends, and cyanoacrylates such as HB Fuller M2240-05, Permabond ET5393, Permabond 2011, Infinity CA-110-M, Loctite 4014 with or without primer such as HB Fuller 6070 or Loctite 713, structural acrylic adhesives such as Permabond TA430, TA435, TA437, TA49, TA459. TA4246 with or without initiator 41 or 46, or the like, or combination thereof. In a preferred example, the adhesive material covers a footprint at least the size of the footprint of the feature (or feature base) contacting the expandable structure surface, larger footprint than and including the footprint of the feature or feature base contacting the expandable structure surface, at least some of the feature surface above the expandable structure surface, or at least the entire outer surface of the feature. In yet another example, the adhesive covers at least an inner surface of a hollow feature.

In a preferred example, the stress-applying features have a blunt contact region of which acts to concentrate the force applied to the occlusive material, resistant material, plaque, or calcified plaque on or within the wall of the blood as the expandable structure or scaffold expands in the blood vessel or other body lumen.

In a preferred example, the plaque disrupting features contact region is symmetrical. Symmetrical configurations provide for the smooth navigation through the vasculature without hanging up or causing a vessel injury. In other examples, the plaque contact region is asymmetrical.

Individual stress-applying features will typically possess a single blunt contact region, but in some instances may possess two, three, or more separately formed blunt contact regions each defined by a continuous peripheral boundary. Individual blunt contact regions will typically have an area in a range from 0.0001 mm$^2$ to 5 mm$^2$, preferably from 0.001 mm$^2$ to 2 mm$^2$, more preferably from 0.001 mm$^2$ to 0.2 mm$^2$, and most preferably from 0.01 mm$^2$ to 0.2 mm$^2$. In one example, the total outer surface area of the sinusoidal scaffold ring or balloon will typically have an area in a range from 0.05 mm$^2$ to 10 mm$^2$, preferably from 0.5 mm$^2$ to 2.5 mm$^2$, more preferably from 0.5 mm$^2$ to 1.5 mm$^2$. Depending on both the total number of blunt contact regions and contact areas of the individual blunt contact regions, the force per unit area (pressure) applied by the stress-applying features will be increased by a factor in a range from 1 to 1000, often from 1 to 100, preferably from 1 to 50.

The radial distance of the blunt contact region of the stress-applying feature above the outer surface of the expandable structure such as scaffold or other structures may be in a range from 0.05 mm to 1 mm, preferably 0.15 mm to 0.5 mm. The blunt contact regions may have a width or diameter (in the case of circular blunt contact regions) in a range from 10 μm to 2.5 mm, preferably ranging from 30 μm to 250 μm. In some instances, the blunt contact regions may have a width to length ratio in a range from 1:3 to 3:1, often 1:2 to 2:1, and about 1:1, often being circular.

The stress-applying feature will typically be positioned directly over the outer surface of the scaffold, i.e., the feature will be integrally formed, subsequently deposited, or other located so that it extends or protrudes radially away from the outer surface of a strut, crown, link, or other primary component of the scaffold. In other instances, however, the stress-inducing feature can be formed as an integral but appurtenant component of the scaffold, e.g., has an arm or other integral connector (similar to a link between adjacent rings) extending from and connecting the feature to a primary scaffold element. Examples include a stress-applying features attached to a scaffold crown, strut, or link by an arm. In some examples, a single appurtenant stress-applying feature may be attached to two or more primary scaffold components (e.g., crowns, struts, or links) by two or more individual arms.

Such appurtenant stress-applying features may be formed to have a radially outwardly protruding blunt contact region and be useful with further reconfiguring or deformation. In this way, the blunt contact regions can be positioned laterally away from the outer surfaces primary scaffold components. In other instances, the appurtenant features can be folded, typically over by bending the attachment arms, so that they overlie an outer surface of an adjacent primary scaffold component. Optionally, such folded appurtenant features can be further attached to the primary component by any of soldering, welding, gluing, press fit, mechanical fit, tying or other technique, as described previously.

In some examples, the stress-applying features are placed on opposite surface regions on an expandable structure such as a balloon surface or a scaffold circumferential ring, such as on substantially opposite crowns and/or struts, i.e., being separated by 180°. In other examples, individual stress-applying features may be distributed over the circumference of a balloon, sleeve, cage, or an individual ring by other equal angular separations, e.g., by 30°, 45°, 60°, 90°, or 120°, typically being located on the surface of a crown, strut, axial link or bridging two or more of such scaffold structures. In these and other instances, the stress-applying features on an expandable structure or on an individual ring may be circumferentially offset from those on axial length or one or more axially separated rings, e.g. by about 10°, 20°, 30°, 40°, 60°, or 90°. In still further examples, the stress-applying features may be disposed in a helical pattern along a partial or entire length of the expandable structure or scaffold. In other example, the stress-applying features on an expandable structure, a stent, or an individual ring may be circumferentially and axially offset from each other within said structure, stent, or ring and/or may be circumferentially and axially offset from those on regions of the expandable structure, or one or more other rings. In yet another example, at least one end of the expandable structure or scaffold may have fewer (compared to a middle structure or scaffold region) or no stress-applying features, over at least one, two, three, four, five, six, or more terminal length as measured in mm or cm or circumferential rings on either or both ends of the scaffold, often being free of stress-applying features over these terminal ends or end rings.

In preferred examples, the stress-applying features may be placed on crown regions only; the stress-applying features may be oriented circumferentially around the surfaces of some or all individual rings; the number of stress-applying features per ring may range ranges from 1 to 5, preferably ranges from 2 to 5, and more preferably ranges from 2 to 3 stress-applying features; the stress-applying features may be located only on crown regions, only on link regions, or only on crown and link regions; the stress-applying features may be located only on diametrically opposed crown regions, only on diametrically opposed link regions, or only on diametrically opposed crown and link regions; or the stress-applying features may be located only on crown regions, link regions, or crown and link regions circumferentially separated by 30°, 45°, 60°, 90°, 120°, or 180° on the same ring or on axially adjacent or separated rings. In still other examples, the stress-applying features may be present at a ratio of "stress-applying features" to "crowns" within an individual circumferential ring in a range from 1:1 to 1:4, often from 1:2 to 1:3.

The stress-applying features of the present invention may have any one of a variety of specific shapes and configurations characterized by a blunt contact region at a location spaced-radially outwardly from the outer surface of the expandable structure or scaffold. For example, they may have a disk-like shape, truncated conical shape, a sphere, a ball, an ellipse, a truncated prism-like shape, a truncated tear-drop shape, or the like. The base of the stress-applying feature may contact the outer surface of the expandable structure or scaffold with a footprint having an elliptical, triangular, circular, polygonal, or irregular periphery with the blunt end positioned radially outwardly from the outer surface of the expandable structure or scaffold. In some instances, the stress-applying features can be layered with a base layer affixed to the outer surface of the expandable structure or scaffold and one, two, three or more additional layers formed or attached over the base layer. The layers can be formed from the same or different materials and can be applied or deposited in situ or be pre-formed and attached by any of the methods described previously and can have the same or different shapes, lengths, widths, or height. The stress-applying features will typically be symmetrical but in some instances may be constructed asymmetrically with respect a circumferential and/or axial line or plane.

The blunt contact regions will typically be circular, but in some instances may be square, rectangular, polygonal, and/ or elongated in an axial or lateral direction. For example, the blunt contact region may have a length and a width with an aspect ratio in a range from 5:1 to 1:10, preferably ranging from 3:1 to 1:10, more preferably 2:1 to 1:10. In a preferred example, the length to width ratio of the blunt contact region ranges from 2:1 to 1:2, about 1:1, or about 1:2. In yet another preferred example, the width of the stress-applying feature or stress-applying feature base is longer than the width of the stress-applying feature. In yet another example, the height of the blunt contact region (radially spaced distance from the outer surface of the expandable structure or scaffold at the point of attachment of the stress-applying figure) is greater than the length or width of the blunt contact region, greater than both said length and width, greater than said length but less that said width, or less than said length but greater than said width. In yet another example, the circumferential width is equal or longer than the axial length of at least some of the stress inducing features.

In most instances where the expandable structure is a stent (scaffold), the base of the stress-applying feature does not extend beyond the edges of the outer surface of a single crown region, a single strut region, or a single link region, but in other instances the base may extend beyond the edges of the scaffold surface and/or may span two or more adjacent crowns, struts, and/or links.

The stress-applying feature will be configured to shear, fracture, break, disrupt, dent, or fragment occlusive material on or in an inner wall of a blood vessel, valve, or body lumen, including both arteries and veins in the cardiac and peripheral vasculature. The occlusive material may comprise calcified lesions often in the form of calcified plaque partially or fully occluding or partially or fully encircling the blood vessel, valve leaflet, or lumen. In a preferred example, the features are composed of or comprised of blunt contact regions which are configured to shear, fracture, dent, break, disrupt, or fragment occlusive material on or in an inner wall of the vessel or body lumen when the expandable structure, such as a balloon, stent, sleeve, or the like, is inflated or expanded to its radially expanded, deployed configuration. For example, the blunt contact region may also have a peripheral edge which shears, fractures, breaks, disrupts, or otherwise fragments the occlusive material while the surface of the blunt contact region inhibits the peripheral edge from unintended cutting or otherwise causing substantial injury, such as dissection, to the blood vessel wall, valve leaflet, or body lumen. In yet another example, the stress-applying feature contact region and peripheral edges are blunt, which expands, dents, shears, fractures, breaks, disrupts, or otherwise fragments the plaque or occlusive material when the blunt contact surface and periphery are forced or pressed against the vessel wall, hardened plaque, valve annulus, valve leaflet or body lumen. In this example, the peripheral edge is dulled by beveling the edges or polishing said edges or coating said edges or feature surface. In yet another example, the stress-applying feature surfaces comprising the contact region, the peripheral regions, the base, and the feature body are blunt which dents, shears, fractures, breaks, disrupts, or otherwise fragments the plaque or occlusive material when the blunt surfaces are forced or pressed against the vessel wall, hardened plaque, valve annulus, valve leaflet or body lumen. In yet another example, the stress-applying feature surfaces comprising the contact region, the base, and the feature body being blunt and free from peripheral edges which dents, shears, fractures, breaks, disrupts, or otherwise fragments the plaque or occlusive material when the blunt surfaces are forced or pressed against the vessel wall, hardened plaque, valve annulus, valve leaflet or body lumen. In yet another example, the stress-applying features on one or more surfaces are blunt, dull, or otherwise causes minimal to no injury to the blood vessel, body lumen, valve annulus, valve leaflet, when the expandable structure containing said features is radially or axially expanded or deployed against a vessel wall, body lumen, or valve annuals/leaflet. In yet another example, the stress-applying features surfaces have the same degree of bluntness, or different degrees of bluntness.

In a preferred example, the stress-applying features comprise one or more of applying force to the tissue, resistant tissue, plaque, calcified plaque, and/or fibrotic plaque to disrupt vessel occlusion, dent vessel tissue and/or occlusion, and/or enlarge a vessel lumen, or body lumen.

In a preferred example, stress-applying features on a contact region may comprise one or more of the following configurations: blunt, atraumatic, dull, wherein the feature contact region of the stress-applying feature shears, dents and/or disrupts and/or fractures hardened vessel tissue and/or calcified plaque to enlarge a vessel lumen.

In another example, the stress-applying feature has one body. In another examples the stress-applying feature comprises a base wherein the base is separate from the feature body and wherein the feature and the base are attached together.

In another example, the stress-applying features are formed on a balloon, on an expandable member, on a sleeve, on a cage, or other devices. In other examples, the stress-applying feature is formed on an outer surface of a balloon, an expandable member, or a sleeve, or cage, or is formed on an inner surface of a balloon, expandable member, or a sleeve, or cage. In one example, the stress-applying features are formed on an inner surface of a balloon, sleeve, cage, or expandable member, said features are configured to protrude radially outwardly above the surface of said balloon, sleeve, cage, or expandable member, upon expansion of the balloon, sleeve, cage, or expandable member, from a crimped or small configuration to an expanded configuration. In another example, the stress-applying features are formed on an inner surface of a balloon, sleeve, cage, or expandable member, and then the balloon, sleeve, cage, or expandable member is inverted inside out providing the features onto the outer surface of the balloon, sleeve, cage, or expandable member prior to expansion of the balloon, sleeve, cage, or expandable member, from a crimped or small configuration to an expanded configuration.

While in many embodiments and examples, the stress-applying features of the present invention are intended to be placed and attached directly to the outer surfaces of expandable structures such as balloons, stent and graft structures, in other instances they may be placed on an outer and/or inner surface of an expandable sleeve or similar support structure that that may be placed over a conventional balloon or stent or vascular graft. In still other instances, the stress-applying features of the present invention may be placed directly on an angioplasty balloon as a supplement or alternative to the blades/elements of a conventional cutting or scoring balloon. In some instances, a balloon having stress-applying features as described herein may be used to expand a stent or vascular graft and the balloon and stress-applying features removed from the stent or vascular graft after expansion.

A wide variety of stress- and force-applying features are described and claimed herein, such as blunt, domed, those having sharp elements, and the like, and a wide variety of expandable structures, or components, or substrates are described and claimed herein, such stents, grafts, balloons, sleeves, cages, and the like. The present invention will include each and every individual type of stress- or force-applying element in combination with each and every expandable structure/component, individually and in combination Additionally, in some instances, the preferred stress-applying features of the present invention may be incorporated on scaffold components that open out radially outwardly from an outer surface of a stent when the stent is radially expanded.

In still other instances, the surfaces of stress-applying features, including the blunt contact regions, can be roughened or otherwise modified to enhance adherence to the surface of the vessel, or calcified lesion, for example having one or more tissue interfacing features such as a texture, polish, friction, barbs, spikes, wedges, microstructure patterns, or the like on, on, over, or adjacent to the surface, features to stably engage the vessel wall tissue before, during, or once occlusive material has been fractures to minimize mispositioning or sliding of the expandable structure such as balloon, sleeve, cage, or of the scaffold at or adjacent to the stress-applying features. In yet another example, the base of the feature may be roughened to enhance bonding of the base to the expandable structure surface.

In still other instances, the stress-applying features may comprise a sharp element projecting outwardly from the blunt contact region. The sharp element, e.g., a shaft or other body having a sharp tip or sharp edge, is typically configured to concentrate stress when engaged against the occlusive material on the wall of a vascular lumen when the blunt contact region is pressed against a surface of the occlusive material. The height of the sharp element will be selected to be sufficient to enhance or "nucleate" fracturing of a hardened lesion while reducing or eliminating the risk of injury to the arterial wall, both underlying the lesion and away from the lesion. For example, the blunt surface may extend above a surface of the balloon, or scaffold by a first distance and the sharp element projects from the surface of the blunt contact region by a second distance equal to 0.05 to 0.1 mm of the first distance. Typically, the sharp element will have a height or length of at least 0.01 mm, typically being in a range from 0.01 mm to 0.2 mm, usually being in a range from 0.01 mm to 0.1 mm.

In a first aspect, the present invention provides an endoluminal prosthesis comprising a scaffold and a plurality of stress-applying features coupled to an outer surface of the scaffold. The scaffold is composed at least partly of a non-degradable material and configured to expand from a crimped configuration to an expanded, deployed configuration. At least some of said stress-applying features comprise a blunt contact region spaced outwardly from said outer surface where the blunt contact region is configured to fracture occlusive material in the wall of a vascular lumen when the scaffold is expanded from the crimped configuration to the expanded configuration in the vascular lumen. The scaffold in other examples may be composed of degradable materials, such as degradable polymeric materials or degradable metallic materials, or may be composed of non-degradable material such as non-degradable metallic or metallic alloy materials, wherein the materials are configured to expand from a crimped configuration to an expanded, deployed configuration.

In preferred example, the plaque disrupting features are applied to a non-degradable scaffold structure. In other examples, the plaque disrupting features are applied to a degradable scaffold structure in a physiologic environment, wherein the degradable material comprises a degradable polymeric material or a degradable metallic or metallic alloy material.

In specific examples, the scaffold or expandable structure may have a tubular geometry, for example having a cylindrical shape, an ellipsoidal shape, a tapered profile, an hourglass shape, a dog-bone shape, other shapes, or the like.

In specific examples, at least some of the blunt contact regions comprise a peripheral edge configured to concentrate stress when engaged against the occlusive material on the wall of a vascular lumen when the expandable structure such as a scaffold is expanded from the crimped configuration to the expanded configuration in the vascular lumen. Such concentrated stresses will shear, fracture, break, disrupt, or otherwise fragment the occlusive material which is contacted by the blunt contact regions. The peripheral edge may be formed by an intersection between the blunt contact region and a peripheral wall at least partially surrounding the blunt contact region. The blunt contact region may have a variety of shapes or surfaces such as flat, rounded, convex, or concave.

In specific examples, the blunt contact region may be flat, and the blunt contact region may be parallel to the outer surface of the scaffold. Alternatively, the blunt contact region may be inclined relative to the outer surface of the expandable structure or scaffold. The peripheral wall may be oriented at an angle in a range from 75° to 105° relative to the blunt contact region. A peripheral edge may extend fully or partially about the blunt contact region and may have a width in a range from 10 μm to 200 μm. In some instances, the peripheral edge may be circular, and the width comprises a diameter.

In specific examples, at least some of the plurality of stress-applying features comprise one or more plates having a total thickness in a range from 0.1 mm to 1 mm, 0.15 mm to 1 mm, or 0.25 mm to 1 mm and a width when attached to the surface of the expandable structure or tubular scaffold in a range from 0.05 mm to 2 mm or 0.1 mm to 2 mm. At least some of the plates may be configured as disks, stacked disks, truncated cones, disks stacked with truncated cones, ellipsoidal disks, asymmetric cones, and the like. In other example the stress-applying feature may comprise one or more spheres, balls, hemispheres, partial spheres, or the like forming various shapes a "snowman" shape, or other configurations, or combination thereof.

In specific examples, the scaffolds may be formed as conventional intravascular stents, typically comprising a plurality of struts joined by crowns. The struts and crowns may be formed into circumferential rings, and in some instances the plurality of struts joined by crowns may be joined into a plurality of successive, adjacent circumferential rings joined by axial links and in other cases the rings may be joined in a helical or other pattern.

In preferred instances, at least some of the stress-applying features may be located at or adjacent to crowns and optionally at least some of the crowns carrying stress-applying features may be not joined to adjacent rings. Often, each of the stress-applying features will be located at or adjacent to a crown.

In alternative instances, at least some of the stress-applying features may be located on the struts between crowns or may located on one or more links joining adjacent rings.

In some instances, at least some of the stress-applying features may be arranged in diametrically opposed pairs and optionally successive diametrically opposed pairs of crowns may be circumferentially offset. Such successive diametrically opposed pairs of crowns may be circumferentially offset by an angle from 45° to 90°.

In alternative instances, at least some of the stress-applying features may be arranged in groups of three, four, or five, which may be circumferentially separated about a circumference or circle on the surface of the expanded structure or tubular scaffold by about 120°, 90, or 72°, respectively. In another instances, at least some of the stress-applying features may be arranged in groups of three, four, or five, which may be circumferentially separated about a circumference or circle on the surface of the expanded structure or tubular scaffold by about 120°, 90, or 72°, respectively along the length of the expanded structure or stent.

In still other instances, the stress-applying features may be arranged in other regular and/or random patterns. For example, in some patterns, successive axially spaced-apart stress-applying features will be circumferentially offset by an angle in a range from 5° to 15°. Alternatively, or additionally, at least some successive circumferentially spaced apart stress-applying features may be axially offset by the same or a different angle in the range from 5° to 15°.

In a specific example, the scaffolds of the present invention may be formed by patterning a tubular substrate, laser cutting a tubular substrate, rolling a cut substrate, bending a wire, by three-dimensional printing, or by other known stent fabrication techniques. The stress-applying features may be pre-formed and attached by gluing, soldering, welding, threaded attachment, riveting, crimping, or the like. For example, the stress-applying features may comprise pre-formed plates glued to the scaffold with an adhesive. Alternatively, the stress-applying features may be formed in situ by three-dimensional printing, chemical vapor deposition, electrostatic deposition, molding, or folding of a component of the scaffold. For example, the stress-applying features may comprise tabs attached to the scaffold and folded over onto the outer surface of the scaffold.

In specific examples, the scaffold may comprise a vascular stent or stent-graft. In other examples, the scaffold may comprise a prosthetic valve, a valvuloplasty device, a sleeve, or the like. In each of such instances, the scaffold may be balloon expandable or self-expanding.

In a second aspect, the present invention provides a method for fracturing calcified plaque in a patient's vasculature. A scaffold as in any one of the embodiments described previously is expanded from a crimped configuration to an expanded configuration in a calcified body vascular lumen. A plurality of stress-applying features fixed to an outer surface of the scaffold are caused to dent, expand, open, or fracture occlusive material on or in the wall of a vascular lumen when the tubular scaffold is expanded from the crimped configuration to the expanded configuration. The occlusive material typically comprises hardened plaque or calcification.

In specific instances, expanding the scaffold comprises expanding a balloon to expand the scaffold or alternatively allowing the scaffold to self-expand. For example, expanding the scaffold may comprise expanding a prosthetic heart valve in a heart valve annulus, wherein the scaffold comprises a structural support of the heart valve annulus, e.g., expanding the prosthetic heart valve may comprise expanding a balloon to expand the prosthetic heart valve in the heart valve annulus or may comprise removing a crimped elastic scaffold from radial constraint after positioning in the heart valve annulus.

In other examples, expanding the scaffold comprises expanding a valvuloplasty device in a heart valve annulus.

The scaffold of the valvuloplasty device may comprises an expandable cage and expanding the valvuloplasty device comprises expanding the cage in the heart valve annulus.

Cages according to the present invention may be formed from elastic and/or malleable metals and polymers, including but not limited to any of the materials described herein for the fabrication of scaffolds and stents. Such cages may be self-expanding, balloon expandable, or the like, and self-expanding cages may be configured to self-expand when released from radial constraint and/or to radially expand in response to mechanical actuation, e.g., by axial foreshortening. Each of these radial expansion mechanisms is well known and need not be described further.

In a third aspect, the present invention provides a method for fabrication of a vascular scaffold. A tubular scaffold comprises a plurality of struts joined by crowns within a tubular envelope. A plurality of tabs extending outwardly from the struts and/or crowns within the tubular envelope are folded over an outer surface of the tubular envelope to form a plurality of stress-applying features on an outer surface of the tubular scaffold.

In specific instances, pairs of adjacent tabs folded one over the other to form stacked stress-applying features. The adjacent tabs in the pairs may be arranged side-by-side on the scaffold prior to folding. Alternatively, the adjacent tabs in the pairs may be arranged in tandem on the scaffold prior to folding. As a further alternative, the adjacent tabs in the pairs may be arranged on opposite sides of a strut prior to folding.

The stress-applying features can also be placed on extensions to a crown, strut, link or other structural element of the scaffold. The extension can be supported or connected to the same or a different structural element on the same ring or a diametrically opposite ring, and preferably the extension has a free terminal end wherein the stress-inducing feature is placed on or about such terminal end. Such an extension can have a width which is the same as or different from that of the element from which the extension extends and can have any one of various shapes and configurations.

Stress-inducing features may be placed on struts, strut extensions, crowns, crown extensions, links and/or link extensions. Preferably, the stress-inducing features are placed on a structural element that is deflectable in a radially outward direction when the scaffold is expanded from a crimped configuration to a deployed configuration, for example being located at a terminal or other free end or side structure of a crown, strut, link, or extension that is free to deflect as a "cantilevered" element. In a further preferred example, the stress inducing feature is placed on a terminal end of an extension or on hinge element wherein the hinge element comprising a crown or part of a link such as a Z, M, W, U, V, S-shaped link.

In some instances, a stress-inducing feature can be located on an inner surface of the scaffold, for example on a cantilevered end of a crown region or extension, a strut region or extension, and/or link region or extension. In such instances, expansion of a balloon or other expandable element within the scaffold will deflect the cantilevered end radially outwardly relative to the reminder of the outer surface of the scaffold (the feature on the inner surface will act as a spacer to preferentially expand the outer surface), thus acting as if the feature had been placed on the outer surface of the scaffold. In such instances, the feature on the inner surface need not be configured to fracture occlusive material (preferably being configured not to damage the expanding balloon) but the outer surface of the crown, strut, link or extension, which is deflected will have a peripheral edge configured to fragment or crack plaque, calcium, or other occlusive material.

In some instances, the stress-inducing features may be held on the outer or inner surface of the scaffold by an arm, clamp, or other connecting element which is fabricated together with the scaffold. Such stress-inducing features may be coupled and positioned in place (for example by bending an attaching arm) but not affixed. In such cases, the stress-inducing feature may contact the surface of the scaffold or there may be a gap left between the feature and the surface of the scaffold. As with other cases, these stress-inducing features will contact the occlusive material upon expansion of the scaffold.

In some examples, a plurality of stress-inducing features may be circumferentially and axially offset within a single row or more of features on a circumferential ring or a circumference of an expanded structure. For example, three stress-inducing features placed on three crowns within a ring will be circumferentially offset but may or may not be axially offset. They will be axially offset if the crowns are axially offset and/or certain of the stress-inducing features are located on struts.

While the stress-applying features of the present invention will usually have blunt contact regions, as described previously, in alternative instance they may comprise cones or pyramids which are not truncated and may or may not comprise a blunt contact region.

In a further aspect of the present invention, apparatus for treating hardened plaque, or calcification on or in a wall in a patient's body vessel or lumen or valve annulus or leaflet, comprises a catheter including a catheter body having a proximal end and a distal segment, an expandable structure disposed at or near the distal segment of the catheter, said expandable structure having an outer surface configured to be displaced radially outwardly toward an inner surface of the vessel wall, body lumen wall, or valve annulus, and a plurality of plaque-disrupting features distributed over the outer or inner surface of the expandable structure, wherein at least some of the plaque-disrupting features are attached to the outer or inner surface of the expandable structure and have, in one example, a convex rounded upper or base surfaces configured to dent, open, expand, or fracture, the calcification or vessel or body lumen while minimizing damage to the vessel or body lumen when the expandable structure is expanded within the vessel or body lumen. The expandable structure may be advanced into the target vessel or body lumen, prior to advancing a balloon catheter into the expandable structure to expand said expandable structure to disrupt a hardened plaque.

Alternatively, the expandable structure is advanced over a balloon catheter which is already in place at the target site, the expandable structure is then bridged over (placed over) the balloon segment, prior to expansion of the balloon to expand the expandable structure to disrupt a hardened plaque. In yet a third example, the expandable structure is placed over (bridged over) the balloon segment of the balloon catheter prior to insertion in a patient body and the system is introduced together into the patient body. In yet a fourth alternative, the expandable structure is advanced distally to the target site, the balloon catheter is advanced to the target site, the expandable structure is retracted to bridge over (placed over) the expandable balloon segment, in order to expand the expandable structure. In one preferred example, the expandable structure comprises an elastic tubular body being expandable from a crimped or small configuration to an expanded configuration. In another example, the expandable structure comprises a cage comprising two or more elongated members that are axially and circumferentially separate connecting the distal end of the catheter to a proximal end of the catheter distal segment, said strip are not connected to adjacent strips except at said proximal and distal ends, wherein the elongated members are expandable from a small configuration to an expanded larger configuration.

In another example, Such apparatus in any of the examples may be configured for treating a blood vessel, a valve annulus, a venous valve, or AV shunt, a body lumen, where the hardened plaque or calcification is typically located on or within an inner wall, an intimal layer, a medial layer, an adventitial layer, a valve leaflet, valve annulus, venous filter, or an implant.

In some examples, the expandable structure may be less rigid when not expanded and more rigid when fully expanded.

In some examples, the outer surface of the expandable structure may be generally cylindrical when fully or partially deployed or deployed or expanded. In other examples, the expandable structure may be oblong, convex, hour-glass shape, tapered, cone shaped, ellipsoid shape, or other shapes or configurations, when expanded or deployed to the expanded configuration.

In some examples, the plaque-disrupting features comprise convex rounded upper surfaces of plurality of plaque-disrupting features may extend radially outwardly beyond the outer surface of the expandable structure when fully expanded. For example, the convex rounded upper surfaces of plurality of plaque-disrupting features may extend radially outwardly beyond the outer surface of the expandable structure by a distance in a range from 0.25 mm to 3 mm, preferably ranging from 0.5 mm to 3 mm when partially or fully expanded.

In some examples, the convex rounded upper surfaces of the plaque-disrupting features may be free from edges and irregularities which could damage the wall when the expandable structure is expanded within the body lumen.

In some examples, at least some of the plaque-disrupting features may have a single convex rounded upper surface and a lower base independently attached to the outer surface of the expandable structure.

In some examples, at least some of the plaque-disrupting features may have a convex rounded tissue contacting surface and a base attached to the surface of the expandable structure.

In some examples, at least some of the plaque-disrupting features may have a concave tissue contacting surface and a base attached to the surface of the expandable structure. In other examples, at least some of the plaque-disrupting features may have a convex tissue contacting surface and a base attached to the surface of the expandable structure.

In some examples, at least some of the plaque-disrupting features may have a convex rounded tissue contacting surface and a base attached to the surface of the expandable structure, wherein the base has the maximum configuration or maximum dimension of the feature maximum configuration or maximum dimension.

In some examples, at least some of the plaque-disrupting features are formed from a metal or metal alloy. In other examples, the features are formed from polymeric material. In yet a third example, the features are formed from a polymeric material and coated with a harder material such as metal or metal alloy material to provide the necessary hardness to disrupt hardened plaque. In yet another example, the material forming the features may be ceramic. In yet another example, the material forming the feature may be coated with a harder material to provide sufficient strength to disrupt hardened plaque. In yet another example, the material forming the feature may be coated with a softer (less hardness) material to provide roundness, convexity, lubricity, less friction, or dullness, such as in the example of a metallic material forming the features and such material coated with an adhesive material, polymeric material, and/or hydrophilic coating. In yet another example, the material forming the features may be coated with a similar hardness material to provide one or more of roundedness, convexity, dullness, and/or atraumatic surface.

In another example, the plaque disrupting features along the circumference and/or axial length of the expandable structure may have same or different height, width, length, diameter, shape, and/or configuration.

In some examples, at least some of the plaque-disrupting features is composed of or comprise a quadratic surface, configuration, or shape. In some examples, the base surface of the quadratic shaped feature attached to the expandable structure surface is flat, oval, rounded, square, rectangle, or contoured to the surface of the expandable structure. In some examples, the maximum height from the contact region to the base of the quadratic shaped feature is about equal to half the maximum width, length, or diameter of the base of said feature. In other examples, the maximum height from the contact region to the base of the quadratic shaped feature is smaller than half of the maximum width, length, or diameter, of the base of said feature. In yet other examples, the maximum height from the contact region to the base of the quadratic shaped feature is larger than half of the maximum width, length, or diameter, of the base of said feature.

In some examples, at least some of the plaque-disrupting features comprise a quadratic shape or configuration comprising at least one of sphere, ellipsoid, oblate, or prolate structure.

In some examples, at least some of the plaque-disrupting features are composed of or comprise partial sphere, partial ellipsoid, partial oblate, or partial prolate structure.

In a preferred example, at least some of the plaque disrupting features have a contact region surface formed having rounded, contoured, dull, smooth, convex, and/or atraumatic surface. In other examples, the plaque disrupting features contact region surface are coated, covered, or plated with a material to provide rounded, contoured, dull, smooth, convex, and/or atraumatic surface. In one example, the material coated, covered, or plated is metallic, polymeric, ceramic, or other type material configured to provide rounded, contoured, dull, smooth, convex, and/or atraumatic surface.

In a preferred example, at least some of the plaque disrupting features have their entire surface(s) above the base surface attached to the expandable structure surface have rounded, contoured, dull, smooth, convex, and/or atraumatic surface as formed or as plated, as coated, or as covered.

In a preferred example, at least some of the plaque disrupting features have their entire surface(s) including the base surface attached to the expandable structure surface being rounded, dull, smooth, convex, rounded, and/or atraumatic surface as formed, as plated, as coated, and/or as covered.

In some examples, at least some of the plaque-disrupting features may comprise spheres or ellipsoids.

In other examples, at least some of the plaque-disrupting features are formed from spheres, partial spheres, or hemispheres. In one example, the partial spheres maximum height ranges from 0.1 mm to 3 mm, preferably ranges from 0.25 mm to 2 mm. In one example, the partial spheres maximum diameter ranges from 0.1 mm to 2 mm, preferably ranges from 0.25 mm to 1 mm. In yet another preferred example, the partial spheres have a configuration ranging from 10% to 90% of a configuration of a sphere, preferably ranging from 25% to 75% of a sphere configuration. In a preferred example, the partial sphere is a hemisphere (half a sphere). In a preferred example, the plaque disrupting features comprise a plurality of spheres wherein the spheres diameter ranges from 0.20 mm to 2 mm, preferably ranges from 0.25 mm to 1 mm. In another example, the plaque disrupting features comprise a plurality of partial spheres or hemispheres. In one example, the partial spheres or hemispheres have a maximum diameter ranging from 0.2 mm to 2 mm, preferably ranging from 0.25 mm to 2 mm. In another example, the plurality of spheres, partial spheres, or hemispheres have the same size, height, and/or diameter along the expandable structure circumference and/or axial length. In other example, the plaque disrupting spheres, partial spheres, or hemispheres have different size, height, and/or diameter along the expandable structure circumference and/or axial length. The partial sphere in one example may be directly attached to the expandable structure surface. In another example, the partial sphere may have a separate base attached to the expandable structure surface and attached to the partial sphere base. In yet another example, the partial sphere may have an integral base to the partial sphere that is attached to expandable structure surface.

In some examples, at least some of the plaque-disrupting features may comprise hemispheres having lower surfaces attached to the outer surface of the expandable structure. For example, the lower surfaces may be flat or may be contoured to the expandable structure surface.

In some examples, at least some of the plaque-disrupting features may comprise posts having hemispherical upper surfaces and lower surfaces attached to the outer surface of the expandable structure.

In some examples, the expandable structure may comprise an inflatable balloon. For example, the inflatable balloon may have a distensibility below or not more than 10% when inflated to a pressure of at least 8 atm, at least 10 atm, at least 12 atm, at least 16 atm, at least 18 atm, or at least 20 atm.

In some examples, the plaque-disrupting features are attached to the outer surface of the expandable structure by at least one of an adhesive bonding, ultrasonic welding, fusion, heat welding, a fastener, solvent bonding, bonding with a polymeric material, or combinations thereof. In a preferred example, the plaque disrupting features are bonded using 2 or more adhesives one adhesive adheres better or is more compatible with the expandable structure material while the other adhesive adheres better or is more compatible to the feature material.

In some examples, the inflatable balloon has a central surface region, a distal tapered surface region, and a proximal tapered surface region where the stress-applying features or plaque-disrupting features are present on one or more of these surface regions. In some examples, the inflatable balloon has a central surface region, distal and/or proximal flat regions, one or more radially protruding surface regions, one or more hour-glass region, and/or one or more oblong-shaped region, where the stress-applying features or plaque-disrupting features are present on one or more of these surface regions. Usually, the stress-applying features or plaque-disrupting features are present on at least the central region. More usually, the plaque-disrupting features are present on at least one of the distal and/or proximal flat or tapered regions, or radially as formed protruding surface regions, and sometimes, the plaque-disrupting features are present on both of the distal and proximal tapered regions. In some instances, the stress-applying features are present on at least the central region, wherein the central region adjacent to the proximal and/or distal taper of the balloon are void of stress-applying features. In some instances, the stress-applying features are present on at least the central region, wherein the central region near to the proximal and/or distal taper of the balloon are void of stress-applying features, said region ranging in length from 0.1 mm to 3 mm are void of stress-applying features.

In some examples, the apparatus may further comprise an outer sleeve having plaque disrupting features on the inner surface or on the outer surface of the sleeve, wherein the sleeve is advanced or retracted over an expandable structure such as a balloon typically in-vivo, where the outer sleeve features protrude radially outwardly before, upon advancing or retracting the sleeve over the balloon, or upon inflation of the balloon to the expanded configuration. The sleeve conforms to the plaque-disrupting features when the expandable structure is expanded, wherein the elastomeric tubular member is configured to expand and contract with the expandable structure expansion and contraction.

In another example, an elastomeric tubular member may be placed over and expandable structure such as a balloon containing plaque disrupting features, where the sleeve shields the plaque disruption features as the apparatus is advanced or retracted in a body vessel or lumen. The sleeve may be laminated or attached to at least a portion of the outer surface of the expandable structure. For example, the elastomeric tubular member may be attached to the expandable balloon segment, to a segment distal to the expandable balloon segment, or to a segment proximal to the balloon segment. Alternatively, the outer sleeve may comprise an elastic, a non-distensible or semi-compliant sheath covering or folded over the balloon before the balloon is inflated. In most instances, the outer sleeve fully covers the clot disruption features on the outer surface of the expandable structure, typically comprising a polymer. In some examples, the outer sleeve comprises perforations sufficient to allow at least some of the plaque-disrupting features protrude outwardly radially through said perforations when the expandable structure is expanded. In a preferred example, said perforations permit the contact surface region of the stress-applying features to protrude through said perforations.

For example, at least some of the plaque-disrupting or stress-applying features may be attached to an inner surface of the elastomeric tubular member or expandable balloon. In particular instances, at least some of the plaque-disrupting features may be formed as a protrusion from the inner surface of the elastomeric tubular member and are pushed to protrude radially outwardly over the elastomeric tubular member or balloon when the expandable structure is advanced or retracted inside said tubular member and/or when the expandable structure is expanded inside the elastic tubular member, or when the balloon is inflated.

In some examples, the apparatus may further comprise an outer sleeve or a balloon member having radially outwardly facing protrusion formed the same material of the sleeve or balloon, where the features would be hollow at their base or comprise a hole at their base, and where the features cover, encapsule, or sit onto the outer surface of the sleeve or balloon protrusions. The protrusions provide a larger surface area to attach to the features. The protrusions typically have a configuration that would fit within or inside the feature, where the fit ranges from lose fit to tight fit. The height of the protrusions ranges from 10% of the height of the feature to 100% of the height of the feature.

In some examples, the apparatus may further comprise an outer sleeve or a balloon member having radially inwardly facing protrusion, crater, or indentation formed the same material of the sleeve or balloon, where the features would sit in the outer surface of the sleeve or balloon indentation, and where the indentation covers partially the feature surface ranging from covering 10% to 60% or more of the feature surface. The indentation provides a larger surface area to attach to the features to secure it when the sleeve or balloon are advanced and/or retracted in a patient body, or when the sleeve and/or balloon are expanded to disrupt a hardened plaque. The indentations typically have a configuration that would partially contain the feature. In some examples, the feature fits snugly within the indentation. In other examples, the feature fits tightly within the indentation. In some other examples, the feature or feature base stretches the indentation. In yet another example, the indentation has a shape or configuration that contours to the shape of the feature or feature base. In indentation typically is coupled to or attached to the feature by press fit and/or one or more adhesive material covering the surface of the indentation and/or feature surface and/or feature base surface.

In some examples, at least some of the plaque-disrupting features may have a base attached to the outer surface of the expandable structure, said base having a width in an axial direction (Wa) and a width in a circumferential direction (Wc) with a width ratio Wa:Wc in a range from 1:0.5 to 1:5; usually from 1:1 to 1 to 1:5; more usually from 1:1 to 3:1. For example, at least some of the bases may have a circular periphery or may have an oval periphery. In other examples, the Wa:Wc is in a range from 3:1 to 1:3, usually ranging from 2:1 to 1:2, and more usually ranging from 1.5:1 to 1:1.5, and most usually about 1:1. In some examples, the base is an integral part attached to the plaque-disrupting features, and is attached to the expandable structure surface. In other examples, the base is a separate part from the plaque disrupting feature and is attached to the plaque disrupting feature and attached to the expandable structure surface.

In some examples, at least some of the plaque-disrupting features may be arranged in diametrically opposed pairs. For example, successive diametrically opposed pairs of plaque-disrupting features may be circumferentially offset. For example, the successive diametrically opposed pairs of plaque-disrupting features may be circumferentially offset by an angle from 45° to 90°.

In some examples, at least some of the plaque-disrupting features may have a base attached to the outer surface of the expandable structure, wherein the base of each feature in the group of features about the expandable structure circumference in the expanded configuration do not overlap one another. In other examples, the base of each of said features do not overlap with other base of features located along a certain axial length of the expandable structure, or along the length of the expandable structure axial length. In yet another example, the base of each feature does not overlap another feature base along the circumference of an expandable structure when expanded and does not overlap an axially adjacent feature along the axial length of the expandable structure when the structure is expanded.

In some examples, at least some of the plaque-disrupting features may be arranged in groups of three which are circumferentially separated about a circle on the surface of the expandable structure by about 120°.

In some examples, at least some of the plaque-disrupting features may be arranged in groups of 2 which are circumferentially separated about a circle on the surface of the expandable structure by about 180°.

In some examples, at least some of the plaque-disrupting features may be arranged in groups of 4 which are circumferentially separated about a circle on the surface of the expandable structure by about 90°.

In some examples, at least some of the plaque-disrupting features may be arranged in groups of 2-4 each which are circumferentially separated about a circle on the surface of the expandable structure by about 90° to 180°, wherein each group forms a helical pattern along the length of the expandable structure when the structure is in the expanded configuration.

In some examples, at least some of the plaque-disrupting features may be arranged in groups of 3 to 10 features per group which are circumferentially separated about a circle on the surface of the expanded structure by about 36° to 120° wherein each feature footprint or base about said circle overlaps no more than one other feature footprint or base along said circle.

In some examples, at least some of the plaque-disrupting features may be arranged in groups of 3 to 10 features per group which are circumferentially separated about a circle on the surface of the expanded structure by about 36° to 120° wherein each feature footprint or base about said circle overlaps no more than two other feature footprint or base along said circle, and wherein each feature about said circle overlaps no more than one to five other features along an axial length path of the expandable structure when the structure is expanded, preferably along the entire length of the expanded structure.

In some examples, at least some of the plaque-disrupting features may be arranged in groups of 3 to 10 features per group which are circumferentially separated about a circle on the surface of the expanded structure by about 36° to 120° wherein each feature footprint or base from each group about said circle does not overlap other features footprint or base from the same group along said circle, and wherein each feature about said circle also does not overlap other features from other groups along an axial length path of the expandable structure when the structure is expanded, preferably along the entire length of the expanded structure.

In some examples, at least some of the plaque-disrupting features may be arranged in groups of 3 to 10 features per group which are circumferentially separated about a circle on the surface of the expanded structure by about 36° to 120° wherein each feature footprint or base from each group about said circle has a gap when the underlying structure is fully expanded between said feature and other features footprint or base of the same group said gap ranging from 0.05 mm to 2.5 mm, preferably ranging from 0.1 mm to 1.5 mm. In a preferred example, the gap between any two features of the same group is measured along an axial length between said two features footprint or base circles.

In some examples, at least some of the plaque-disrupting features may be arranged in groups of 3 to 10 features per group which are circumferentially randomly separated about a circle on the surface of the expanded structure by about 10° to 180°.

In some examples, the plaque-disrupting features may be arranged in a helical pattern along a length of the expandable structure, preferably along the entire length of the expandable structure when the structure is in the expanded configuration. In some instances, the helical pattern of at least some plaque-disrupting features completes one to five 360° turns along said length, or along the entire length of the expanded structure. In some examples, the plaque disrupting features or features bases do not overlap about the circumference of the expandable structure and/or axial length.

In some examples, the plaque-disrupting features may be arranged in a straight pattern along a length of the expandable structure, preferably along the entire length of the expandable structure when the structure is in the expanded configuration.

In some examples, the plaque-disrupting features may be arranged in one region of the expandable structure. For example, the plaque disrupting features may be arranged in a mid-region of the expandable structure, such as mid region of a balloon working length.

In other examples, the inflatable balloon coupled to plaque disrupting features may be arranged to prevent the outer surface of the expandable structure surface such as balloon outer surface from contacting hardened plaque or tissue, or are arranged to have the outer surface of said balloon not contact hardened plaque before a minimum threshold pressure, wherein said minimum threshold pressure may be any one of the following nominal or rated balloon inflated pressures: 3 atm, 5 atm, 7 atm, 10 atm, 12 atm, 15 atm, or other.

In other examples of the present invention, the expandable structure such as inflatable balloons may be further configured to deliver drugs and other medicaments. For example, the inflatable balloon may be configured to release an inflation medium comprising a medicament in response to an inflation pressure above a minimum threshold value, e.g., where the minimum threshold value is above 1 atm, 3 atm, 5 atm, or 7 atm. In specific instances, the inflatable balloon may comprise a plurality of ports or perforations within the balloon material surface adjacent to at least some features which open in response to the inflation pressure above the minimum threshold pressures. In some other examples, the inflatable balloon may have a separate a distal conduit formed from an elongated tubular body extending from proximally to said distal conduit to outside the patient to infuse medicaments while the balloon is in the expanded configuration. In yet another example, the medicaments are coated onto one or more of the stress—applying features surfaces, more particularly the engaging or contact surface region of the stress-applying features, to provide medicaments to the tissue when the features come into contact with the vessel or annulus or leaflet tissue. In one example, the medicaments are coated or sprayed directly onto at least the contact region surface of at least some of the features. In other examples, the medicaments are mixed with a polymeric material and the mixture is then coated or sprayed onto at least the contact region of the stress-applying features. In yet another example, the medicaments are sprayed or coated onto the outer surface of the expandable structure outer surface such as balloon and/or stress inducing features. In yet another example an expandable structure comprising an expandable balloon segment wherein the balloon segment is covered by an outer sleeve comprising an elastomeric member, and wherein the balloon and/or elastomeric member comprises at least some stress-applying features attached to the outer surface of the balloon, the outer surface of the elastomeric member, and/or attached to the inner surface of the elastomeric member, wherein the outer surface of the elastomeric member is coated with a medicament comprising one or more drugs. The drugs covering the at least some features embed into the vessel wall, body lumen, or valve annulus, when the balloon is inflated to embed at least part of its medicament content into the adjacent tissue. In a preferred example, the medicaments comprise one or more drugs of an anti-proliferative drug, an m-tor inhibitor drug, a taxol or analogues drug, a direct thrombin inhibitor drug, and a factor Xa inhibitor drug. In yet another example, the medicament is located in spaces between the balloon segment outer surface and the elastomeric segment inner surface and is allowed to penetrate the elastomeric member through apertures or perforation in the elastomeric member when the balloon is expanded to release said medicaments into the vessel wall, body lumen, or valve annulus.

In still other aspects, the present invention provides a method for treating calcification on a wall in a patient's body lumen, where the method comprises positioning an expandable structure at a treatment site proximate the calcification to be treated and radially outwardly expanding the expandable structure to radially outwardly press a plurality of plaque-disrupting features against the calcification. The plaque-disrupting features are distributed over the outer surface of the expandable structure and at least some of the plaque-disrupting features are independently attached to the outer surface of the expandable structure and have convex rounded upper surfaces and wherein radially outwardly pressing the plurality of plaque-disrupting fractures into the calcification fractures the calcification while reducing damage to the wall.

In still other aspects, the present invention provides a method for treating calcification on a patient's valve having calcified leaflets, where the method comprises positioning an expandable structure at a treatment site proximate the calcification to be treated (such as within or though calcified leaflets) and radially outwardly expanding the expandable structure radially outwardly such that the plaque-disrupting feature press the calcified leaflets against the wall of the annulus fracturing the calcified leaflets. The plaque-disrupting features are distributed over the outer surface of the expandable structure and at least some of the plaque-disrupting features are independently attached to the outer surface of the expandable structure and have convex rounded upper surface.

In yet another aspect of the present invention, an apparatus for treating a patient valve having calcified leaflets comprises a catheter body and a segmented balloon structure. The catheter body has a proximal end and a distal end. The segmented balloon is disposed at the distal end of the catheter body and has opposed internal walls (side walls) configured to be expanded on opposite surfaces of the calcified leaflets in a manner which disrupts calcifications on the calcified valve leaflets. In one example, the internal side walls (or axially facing walls) of the segmented balloon are flat or protruding axially outwardly when the balloon is expanded pressing against the calcified leaflets surfaces from opposite sides disrupting calcification on the calcified valve. In yet another example, at least one of the segmented balloon internal side walls comprise one or more stress-applying features coupled to said side walls and configured to engage the calcified valve leaflet when the balloon is expanded to disrupt said calcification, wherein the features press said calcification against the opposite internal side wall of the segmented balloon. In yet another example, the segmented balloon internal side walls comprise one or more stress-applying features coupled to the walls and configured to engage the calcified valve leaflet from opposite sides when the balloon is expanded to disrupt said calcification. In yet another example, the number of stress-applying features range from 0.1 to 100 features/mm², preferably range from 0.1 to 30 features/mm² of the internal side walls surface, more preferably range from 1 to 20 features/mm² of the internal side walls surface. In yet another example, the stress-applying features may be arranged over the side surface of the expandable structure in a variety of configurations such as circular pattern, circle within circle pattern, spiral pattern, valve leaflet conforming or contouring pattern, or other patterns. In another example, at least some of the stress-applying features on one side of the segmented balloon internal wall are configured (or arranged) to oppose other stress-applying features on the opposite internal wall. In another example, at least some of the stress-applying features have blunt contact regions on one side of the segmented balloon internal wall are configured (or arranged) to oppose other stress-applying features blunt contact region on the opposite internal wall when the balloon is expanded, disrupting calcification between said opposing blunt contact regions. In another example, at least some of the stress-applying features contact region configured to have a convex shape on one side of the segmented balloon internal wall are configured (or arranged) to oppose other stress-applying features contact region on the opposite internal wall configured to have a concave shape to fit into the convex opposing shaped features when the balloon is expanded, disrupting calcification between said opposing blunt contact regions.

In yet another example, at least some features on one side of the internal wall are configured to invaginate, or at least partially invaginate the space between two, three, four, or more features on the opposite internal side wall of the segmented balloon when the balloon is inflated, disrupting calcification in a valve leaflet. In another example, the side and/or internal walls may be covered by an elastomeric member covering at least some of the features and optionally said elastomeric member is attached to a balloon segment or other segment of the balloon catheter and is configured to expand when the balloon is expanded.

In another example, the internal side walls and/or the elastomeric member are configured to expand radially and/or axially when the balloon is inflated (or expanded fully) to press against calcified valve leaflet and disrupt calcification of the leaflet. In alterative examples, segments of the balloon structure slidably attached to or mounted on a shaft of the catheter and are configured to draw the internal side walls together after inflation, optionally being configured to nest when the balloon structure is expanded, typically having nesting conical surfaces.

In still other examples, the opposed internal walls may comprise flat surfaces that are configured to close against each other when the balloon structure is inflated and/or expanded. For example, the segmented balloon structure may comprise a pair of opposed conical balloons having flat bases which comprise the flat surfaces.

In some examples, the calcification-disrupting features on the opposed internal wall surfaces are axially aligned as the balloon segments are drawn together, this applying force to opposed surfaces of the valve leaflet. In other instances, the calcification disruption features on the opposed surfaces are laterally offset so that they do not align axially as the balloon segments are drawn together. In still other instances, the calcification-disrupting features may be on only one of the two the opposed internal wall surfaces.

In yet another example, at least one region of the internal segmented balloon side walls and/or at least one region of the elastomeric member cover and/or at least some of the features are coated with one or more coating comprising a polymeric material, adhesive material, an anti-proliferative agent, a factor Xa inhibitor agent, and a factor IIa inhibitor agent, wherein the coating material is configured to deliver a drug, affix debris of the disrupted calcium to the leaflet or to the internal wall of the segmented balloon, or repair a perforated leaflet. In another example, the coated material is configured to attach to the leaflet, transfer material or drug to the leaflet surface, adhere to the leaflet surface, repair a perforation in the leaflet surface, or hold the leaflet together.

In another example, at least some of the features on opposite sides of the internal side walls of the segmented balloon fit into one another such as a concave and convex contact surface regions, a ball and socket contact surface regions, or other. In some examples, the calcium disrupting features on the expandable structure such as an expandable balloon may be arranged on one or more of the expandable structure surfaces comprising side surface, internal surface, or axially facing surface. In some examples, the expandable structure such as an expandable balloon comprise one or more shapes comprising tubular shape, donut shape, hourglass shape, tapered shape, oblong shape, rectangular shape, square shape, or other. In yet another example, the axially facing region of the expandable structure may have various shapes comprising one or more of flat, convex, concave, donut, or other.

In another example of the present invention, an apparatus for treating a patient valve having calcified leaflets comprises a catheter body having at least two expandable structures, where the at least two expandable structures in one example are configured to expanded together such as a dual balloon configuration where the dual balloon share the same inflation lumen and the same guide wire lumen. In another example, the at least two expandable structures are configured to expanded independently such as at least two balloon structures having separate inflation lumen and same or separate guide wire lumen to the at least two balloon structures. In a preferred example, a dual expandable structure is axially movable over a common axial tubular structure.

In specific instances, the valve calcification treatment apparatus will further comprise a plurality of calcification disruption features distributed over at least one of the opposed internal walls of the segmented balloon structure, preferably over both of the opposed internal walls (and/or axial facing wall). The calcification disruption features may comprise any of the stress-applying and calcification disrupting features described in the present application, typically comprising rounded features, including those hemispherical, balls, and spherical features as described herein.

Preferred disruption features will usually have convex rounded leaflet engaging surfaces configured to fracture the calcification while minimizing damage to the leaflet when the balloon structure is expanded in the patient valve. Usually, the convex rounded upper surfaces of the plaque-disrupting features will be configured to extend from the opposed internal walls so as to engage the leaflets when they are captured between the walls. The rounded surfaces of the features that engage the leaflet will typically have a height or width in a range from 0.01 mm to 3 mm, from 0.1 mm to 3 mm, and usually from 0.5 mm to 2 mm, when the balloon is fully inflated. Most often, the convex rounded upper surfaces of the calcification disruption features will be free from edges and irregularities which could damage the leaflets when the balloon structure is inflated within the patient valve.

In some instances, however, the calcification disruption features may be provided with a sharp element projecting outwardly from the convex rounded upper surface where the sharp element is configured to concentrate stress when engaged against the calcification on the valve leaflet as the balloon surface presses against the surface of the valve leaflet. The sharp features will have a very minimal height or depth so that they will engage and disrupt calcifications while substantially avoiding any injury to the valve leaflet. The individual balloon segments may be fixed to the catheter body so that they engage and capture the leaflets when the balloon structure is inflated without any further manipulation. In other instances, however, the balloon segments may be configured to axially translate relative to each other on the catheter body to provide a variable spacing between the internal walls. In such instances, a first of the segments may be inflated and engaged against the valve leaflets and the second segment inflated and then drawn against the opposed surface of the valve leaflet in order to effect disruption.

In yet another aspect, the present invention provides a method for disrupting a calcification or plaque at a lesion comprising advancing a sleeve over a wire through the lesion, advancing an expandable member over the wire and into an interior of the sleeve, and expanding the expandable member within the sleeve to outwardly radially displace features on an inside and/or outside of the sleeve against the lesion to disrupt the calcification or plaque.

In some examples, the method further comprises removing the expandable member from the sleeve and removing the expandable member and the sleeve over the wire, where the expandable structure may comprise either one of a balloon or other expandable member or a stent and wherein the sleeve is left in place between the stent and the lesion after the stent is expanded. The stress-applying features may protrude radially outwardly from the sleeve into the vessel wall when the expandable structure displaces them radially outwardly upon expansion.

In a still further aspect, the present invention provides a method for disrupting a calcification or plaque at a lesion comprising advancing a cage or basket over a wire across the lesion and expanding the cage of basket to radially displace stress-applying features on the cage or basket against the lesion to disrupt the calcification or plaque.

In some examples, expanding the cage or basket comprises mechanically reorienting structural components of the cage or basket. In other examples, expanding the cage or basket comprises inflating a balloon within the cage or basket, where the balloon may be advanced to the lesion together with the cage or basket or after the cage or basket.

In yet another aspect of the present invention, apparatus for treating calcification on a wall in a patient's body lumen comprises a catheter including a catheter body having a proximal end and a distal segment. An expandable structure is disposed at the distal segment of the catheter body and has an outer surface configured to be displaced radially outwardly toward an inner surface of the body lumen wall. A plurality of plaque-disrupting features are distributed over at least a portion of the outer surface of the expandable structure, where at least some of the plaque-disrupting features are disposed on the outer surface of the expandable structure and have a convex rounded apex configured to fracture the calcification while minimizing damage to the body lumen when the expandable structure is expanded within the body lumen.

In specific instances, the convex rounded apex at least some of the plaque-disrupting features have a radial height above the outer surface of the expandable structure in a range from a minimum of 0.05 mm, 0.1 mm, 0.15 mm, 0.2 mm, or 0.25 mm to a maximum of 1 mm, 0.5 mm, 0.4 mm, 0.3 mm, or 0.25 mm, and a distribution density in a range from 0.1 to 5 features/mm$^2$, preferably from 0.2 to 4 features/mm², more preferably from 0.25 to 3 features/mm² when the expandable structure is expanded.

In other specific instances, the plaque-disrupting features may have a footprint with a maximum width, diameter, or other lateral dimension of 4 mm or less, often being 3 mm or less, more often being no more than 1 mm, and frequently being no more than 0.75 mm, and sometimes being no more than 0.5 mm.

The plaque-disrupting features may have any one of or combination of characteristics, for example comprising any one or more of balls, spheres, hemispheres, domes, and ellipsoidal geometries; being solid; being hollow, being coated, being uncoated, having textured surfaces, having smooth surfaces; may be discrete bodies; may comprise a metal, polymer, or combinations thereof.

In preferred aspects, an encapsulation layer may cover a portion or all of the outer surface of the expandable structure and/or the plaque-disrupting features to immobilize the plaque-disrupting features in a desired pattern on the outer surface of the expandable structure.

In specific examples, the plaque-disrupting features may be immobilized solely by encapsulation layer or may be immobilized by an adhesive between the feature and the outer surface in addition to the encapsulation layer. The encapsulation layer may encapsulate the entire plaque-disrupting feature including the convex rounded apex or the encapsulation layer may encapsulate only a lower portion of the plaque-disrupting feature excluding the convex rounded apex.

In preferred examples, the plaque-disrupting feature may be cradled in an indentation, cavity, recess, receptacle, or other depression in the outer surface of the expandable structure. Such cradling helps secure and stabilize the plaque-disrupting features during introduction and use.

The encapsulation layer may comprise one or more polymers selected from the group consisting of thermoplastic fluoropolymers (PVDF), butyl methacrylate (PBMA), and thermoplastic polyesters (PLLA), and the like.

The encapsulation layer is applied over the outer surface and the plaque-disrupting features by any one of coating, direct fluid application, laminating, and fusing.

The encapsulation layer may have a thickness in a range from 0.01 mm to 0.1 mm (0.5 mil to 5 mil), often being 0.01 mm to 0.05 mm (0.4 mil to 2 mil), and more often being 0.01 mm to 0.02 mm (0.4 mil to 0.8 mil).

The plaque-disrupting features may be constrained over the outer surface of the expandable structure by an elastic sleeve.

The plaque-disrupting features are typically attached to the outer surface of the expandable structure but in some instances may be attached to an inner surface of the elastic sleeve. In some instances, the plaque-disrupting features are hollow and mounted on a post projecting radially outwardly from the outer surface of the expandable structure.

In another aspect, an apparatus for treating calcification on a wall in a patient's body lumen in accordance with the present invention comprises a catheter including a catheter body having a proximal end and a distal segment. An expandable structure is disposed at the distal segment of the catheter body and has an outer surface configured to be displaced radially outwardly toward an inner surface of the body lumen wall. A plurality of plaque-disrupting features distributed over the outer surface of the expandable structure, wherein at least some of the plaque-disrupting features are present on the outer surface of the expandable structure and have an upper surface configured to fracture the calcification while minimizing damage to the body lumen when the expandable structure is expanded within the body lumen. An encapsulation layer covering at least a portion of the outer surface of the expandable structure and the plaque-disrupting features to immobilize the plaque-disrupting features in a desired pattern on the outer surface of the expandable structure.

In some instances, at least some of the upper surfaces of the plaque-disrupting features comprise a convex rounded apex and the encapsulation layer may cover the entire outer surface of at least some the plaque-disrupting features including the upper surface. Alternatively, the encapsulation layer may cover only a lower portion of the outer surface of at least some of the plaque-disrupting features. Often, the plaque-disrupting feature will be disposed in an indentation, recess, receptacle or other indentation on the outer surface of the expandable structure. Alternatively, the plaque-disrupting feature may comprise a hemisphere with a flat bottom adhered to the outer surface of the expandable structure.

In yet another aspect, the present invention provides a method for treating a lesion on a wall in a patient's body lumen comprising providing a catheter having an expandable structure disposed at a distal end thereof, where expandable structure has an outer surface configured to be displaced radially outwardly toward an inner surface of the body lumen wall and the outer wall has a plurality of space-separating "spacer" features distributed over the outer surface of the expandable structure. The expandable structure is expanded in the patient's body lumen such that a radially outward force is applied by the outer surface and the features against the wall while the features maintain a gap between the outer surface of the expandable structure and the inner wall.

The spacer features are typically configured to create and/or maintain the one or more gaps by separating the lesion from the outer surface of the expandable structure adjacent to the features when the structure is in the expanded configuration. The spacer feature typically comprise a plurality of features positioned in a configuration around the circumferential length and/or axial length of the expandable structure to provide, create, or maintain said gaps.

In one instance, the spacer features have axially aligned through holes permitting the passage of fluids, such as contrast media, blood, and/or drug (medicament) solutions, therethrough. Typically, the gap allows fluid perfusion therethrough and past the expandable structure while the expandable structure is expanded. For example, a drug may be perfused into the gap while the expandable structure is expanded, e.g., the expandable structure comprises a balloon and the drug is perfused through a wall of the balloon. In alternative instances, at least some of the space-separating features comprise a drug which is released into the gap.

In particular instances, expanding the expandable structure creates one or more gaps between the outer surface of the expandable structure and the inner wall under physiological pressure to allow fluid perfusion through the one or more gaps.

In preferred instances, the spacer features may comprise a convex rounded apex as described previously with respect to stress-applying and plaque disrupting features of the present invention.

The spacer features may have a radial height above the outer surface of the expandable structure in a range from a minimum of 0.05 mm, 0.1 mm, 0.15 mm, 0.2 mm, or 0.25 mm to a maximum of 1 mm, 0.5 mm, 0.4 mm, 0.3 mm, or 0.25 mm, and a distribution density in a range from 0.1 to 5 features/mm², preferably from 0.2 to 4 features/mm², more preferably from 0.25 to 3 features/mm² when the expandable structure is expanded.

In such perfusion methods, the expandable structure is typically expanded with a force sufficient to create and/or maintain one or more gaps against a physiologic pressure from 0.5 psi to 5 psi, preferably from 1 psi to 3 psi.

The illustrative aspects, examples, or embodiments describes are not meant to be limiting. For example, the examples provided for an implantable scaffold comprising a scaffold structure having a surface configured to be expanded in the patient's body can also apply to other devices described in this application such as sleeves, balloon cages, or the like.

These and other embodiments are described in further detail in the following clauses and description related to the appended drawing figures.

Clause 1. An endoluminal prosthesis comprising:

a scaffold composed at least partly of a non-degradable material and configured to expand from a crimped configuration to an expanded configuration; and a plurality of stress-applying features coupled to an outer surface of the scaffold;

wherein at least some of said stress-applying features comprise a blunt contact region having a contact surface spaced outwardly from said outer surface of the scaffold and configured to fracture occlusive material in the wall of a vascular lumen when the scaffold is expanded from the crimped configuration to the expanded configuration in the vascular lumen.

Clause 2. The endoluminal prosthesis of clause 1, wherein the scaffold has a tubular geometry.

Clause 3. The endoluminal prosthesis of clause 2, wherein the tubular scaffold has a cylindrical shape, an ellipsoidal shape, a tapered profile, an hourglass shape, or a dog-bone shape.

Clause 4. The endoluminal prosthesis of clause 1 to 3, wherein at least some of the blunt contact regions comprise a peripheral edge circumscribing the contact surface and configured to concentrate stress when engaged against the occlusive material on the wall of a vascular lumen when the scaffold is expanded from the crimped configuration to the expanded configuration in the vascular lumen.

Clause 5. The endoluminal prosthesis of clause 4, wherein the peripheral edge is formed by an intersection between the blunt contact region and a peripheral wall at least partially surrounding the blunt contact region.

Clause 6. The endoluminal prosthesis of clause 1 to 5, wherein the contact surface of the blunt contact region is flat, convex, rounded, or concave.

Clause 7. The endoluminal prosthesis of clause 6, wherein the contact surface of the blunt contact region is parallel to the outer surface of the scaffold.

Clause 8. The endoluminal prosthesis of clause 6, wherein the contact surface of the blunt contact region is inclined relative to the outer surface of the scaffold.

Clause 9. The endoluminal prosthesis of clause 8, wherein the contact surface of the blunt contact region is inclined an angle in the range from 5° to 45°, preferably from 10° to 30°.

Clause 10. The endoluminal prosthesis of clause 1 to 10, wherein the peripheral wall is oriented at an angle in a range from 75° to 105° relative to the contact surface of the blunt contact region.

Clause 11. The endoluminal prosthesis of clause 4 to 10, wherein the peripheral edge extends fully about the contact surface of the blunt contact region and has a width in a range from 10 μm to 200 μm.

Clause 12. The endoluminal prosthesis of clause 11, wherein the peripheral edge is circular, and the width comprises a diameter.

Clause 13. The endoluminal prosthesis of clause 1 to 12, wherein at least some of the plurality of stress-applying features comprise one or more plates having a total thickness in a range from 0.25 mm to 1 mm and a width where attached to the surface of the tubular scaffold in a range from 0.1 mm to 2 mm.

Clause 14. The endoluminal prosthesis of clause 13, wherein at least some of the plates are configured as disks, stacked disks, truncated cones, stacked disks and truncated cones, ellipsoidal disks, and asymmetric cones.

Clause 15. The endoluminal prosthesis of clause 1 to 12, wherein the scaffold comprises a plurality of struts joined by crowns.

Clause 16. The endoluminal prosthesis of clause 15, wherein the plurality of struts joined by crowns are joined into a plurality of circumferential rings.

Clause 17. The endoluminal prosthesis of clause 15, wherein the plurality of struts joined by crowns are joined in a helical pattern.

Clause 18. The endoluminal prosthesis of clause 13 to 17, wherein at least some of the stress-applying features are located at or adjacent to crowns.

Clause 19. The endoluminal prosthesis of clause 18, wherein at least some of the crowns carrying stress-applying features are not joined to adjacent rings.

Clause 20. The endoluminal prosthesis of clause 18 or 19, wherein each of the stress-applying features is located at or adjacent to a crown.

Clause 21. The endoluminal prosthesis of clause 13 to 17, wherein at least some of the stress-applying features are located on the struts between the crowns or are located on one or more links joining adjacent rings.

Clause 22. The endoluminal prosthesis of clause 1 to 21, wherein at least some of the stress-applying features are arranged in diametrically opposed pairs.

Clause 23. The endoluminal prosthesis of clause 22, wherein successive diametrically opposed pairs of crowns are circumferentially offset.

Clause 24. The endoluminal prosthesis of clause 23, wherein the successive diametrically opposed pairs of crowns are circumferentially offset by an angle from 45° to 90°.

Clause 25. The endoluminal prosthesis of clause 1 to 21, wherein at least some of the stress-applying features are arranged in groups of three which are circumferentially separated about a circle on the surface of the tubular scaffold by about 120°.

Clause 26. The endoluminal prosthesis of clause 1 to 20, wherein at least some successive axially spaced-apart stress-applying features are circumferentially offset by an angle in the range from 5° to 15°.

Clause 27. The endoluminal prosthesis of clause 26, wherein at least some successive circumferentially spaced-apart stress-applying features are axially offset by an angle in the range from 5° to 15°.

Clause 28. The endoluminal prosthesis of clause 1 to 27, wherein the scaffold formed by patterning a tubular substrate, laser cutting a tubular substrate, rolling a cut substrate, bending a wire, or three-dimensional printing.

Clause 29. The endoluminal prosthesis of clause 1 to 28, wherein stress-applying features pre-formed and attached by gluing, soldering, welding, threaded attachment, riveting, or crimping.

Clause 30. The endoluminal prosthesis of clause 29, wherein the stress-applying features comprise preformed plates glued to the scaffold with an adhesive.

Clause 31. The endoluminal prosthesis of clause 1 to 28, wherein the stress-applying features are formed in situ by three-dimensional printing, chemical vapor deposition, electrostatic deposition, molding, or folding of a component of the scaffold.

Clause 32. The endoluminal prosthesis of clause 1 to 28, wherein the stress-applying features comprise tabs attached to the scaffold and folded over onto the outer surface of the scaffold.

Clause 33. The endoluminal prosthesis of clause 1 to 32, wherein the scaffold comprises a vascular stent or stent-graft.

Clause 34. The endoluminal prosthesis of clause 1 to 32, wherein the scaffold comprises a prosthetic valve.

Clause 35. The endoluminal prosthesis of clause 1 to 32, wherein the scaffold comprises a valvuloplasty device.

Clause 36. The endoluminal prosthesis of clause 1 to 35, wherein the scaffold is balloon expandable.

Clause 37. The endoluminal prosthesis of clause 1 to 35, wherein the scaffold is self-expanding.

Clause 38. The endoluminal prosthesis of clause 1 to 37, wherein the stress-applying features are configured to preferentially contact the occlusive material in the wall.

Clause 39. The endoluminal prosthesis of clause 1 to 38, wherein the scaffold comprises a sleeve configured to be placed over a stent or a balloon or to be self-expanding.

Clause 40. The endoluminal prosthesis of clause 1 to 39, wherein the stress-applying features comprise a sharp element projecting outwardly from the blunt contact region and wherein the sharp element is configured to concentrate stress when engaged against the occlusive material on the wall of a vascular lumen when the blunt contact region is pressed against a surface of the occlusive material.

Clause 41. The endoluminal prosthesis of clause 40, wherein the blunt surface extends above a surface of the scaffold by a first distance and the sharp element projects from the surface of the blunt contact region by a second distance equal to 0.05 mm to 0.1 mm of the first distance.

Clause 42. The endoluminal prosthesis of clause 41, wherein the second distance is in a range from 0.01 mm to 0.2 mm, or 0.01 mm to 0.1 mm.

Clause 43. The endoluminal prosthesis of clause 40 to 42, wherein the sharp element comprises a point.

Clause 44. The endoluminal prosthesis of clause 40 to 42, wherein the sharp element comprises an edge.

Clause 45. A method for fracturing calcified plaque in a patient's vasculature, said method comprising:
expanding a scaffold composed at least in part of a non-degradable material from a crimped configuration to an expanded configuration in a calcified body vascular lumen;
wherein said scaffold comprises a plurality of stress-applying features fixed to an outer surface thereof;
wherein at least some of said stress-applying features comprise a blunt contact region spaced outwardly from said outer surface and having a peripheral edge configured to fracture occlusive material on the wall of a vascular lumen when the tubular scaffold is expanded from the crimped configuration to the expanded configuration in the vascular lumen; and
wherein the stress-applying features fracture the occlusive material as the scaffold is expanded.

Clause 46. The method of clause 45, wherein the occlusive material comprises hardened plaque or calcification.

Clause 47. The method of clause 45 or 46, wherein expanding the scaffold comprises expanding a balloon within the scaffold or allowing the scaffold to self-expand.

Clause 48. The method of clause 45, wherein expanding the scaffold comprises expanding a prosthetic heart valve in a heart valve annulus, wherein the scaffold comprises a structural support of the heart valve annulus.

Clause 49. The method of clause 48, wherein expanding the prosthetic heart valve comprises expanding a balloon to expand the prosthetic heart valve in the heart valve annulus.

Clause 50. The method of clause 45, wherein expanding the scaffold comprises expanding a valvuloplasty device in a heart valve annulus.

Clause 51. The method of clause 50, wherein the scaffold of the valvuloplasty device comprises an expandable cage and expanding the valvuloplasty device comprises expanding the cage in the heart valve annulus.

Clause 52. The method of clause 45 to 51, wherein the tubular scaffold has a cylindrical shape, an ellipsoidal shape, a tapered profile, an hourglass shape, or a dog-bone shape.

Clause 53. The method of clause 45 to 52, wherein the peripheral edge is formed by an intersection between the blunt contact region and a peripheral wall at least partially surrounding the blunt contact region.

Clause 54. The method of clause 45 to 53, wherein the blunt contact region is flat.

Clause 55. The method of clause 54, wherein the blunt contact region is parallel to the outer surface of the tubular scaffold.

Clause 56. The method of clause 55, wherein the blunt contact region is inclined relative to the outer surface of the tubular scaffold.

Clause 57. The method of clause 45 to 56, wherein the peripheral edge is formed by an intersection between the blunt contact region and a peripheral wall at least partially surrounding the blunt contact region.

Clause 58. The method of clause 57, wherein the blunt contact region is planar.

Clause 59. The method of clause 57, wherein the peripheral wall is oriented at an angle in a range from 75° to 105° relative to the blunt contact region.

Clause 60. The method of clause 57 to 59, wherein the peripheral edge has a width in a range from 10 μm to 200 μm.

Clause 61. The method of clause 57 to 60, wherein at least some of the plurality of stress-applying features comprise one or more plates having a total thickness in a range from 0.5 mm to 1 mm and a width where attached to the surface of the tubular scaffold in a range from 0.01 mm to 2 mm.

Clause 62. The method of clause 61, wherein at least some of the plates are configured as disks, stacked disks, truncated cones, stacked disks and truncated cones, ellipsoidal disks, and asymmetric cones.

Clause 63. The method of clause 45 to 57, wherein the scaffold comprises a plurality of struts joined by crowns.

Clause 64. The method of clause 63, wherein the plurality of struts joined by crowns are joined into a plurality of circumferential rings.

Clause 65. The method of clause 63, wherein the plurality of struts joined by crowns are joined in a helical pattern.

Clause 66. The method of clause 63 to 65, wherein at least some of the stress-applying features are located at or adjacent to crowns.

Clause 67. The method of clause 66, wherein each of the stress-applying features is located at or adjacent to a crown.

Clause 68. The method of clause 63 to 65, wherein at least some of the stress-applying features are located on the struts between the crowns.

Clause 69. The method of clause 63 to 68, wherein at least some of the stress-applying features are arranged in diametrically opposed pairs.

Clause 70. The method of clause 63 to 69, wherein successive diametrically opposed pairs of crowns are rotationally offset relative to a longitudinal axis of the scaffold.

Clause 71. The method of clause 70, wherein the successive diametrically opposed pairs of crowns are rotationally offset by an angle from 75° to 105° relative to a longitudinal axis of the scaffold.

Clause 72. A method for fabrication a vascular scaffold, said method comprising:

patterning a tubular scaffold comprising a plurality of struts joined by crowns within a tubular envelope, said tubular scaffold having a plurality of tabs extending outwardly from the struts and/or crowns within the tubular envelope; and folding the plurality of tabs over an outer surface of the tubular envelope to form a plurality of stress-applying features on an outer surface of the tubular scaffold.

Clause 73. The method of clause 72, wherein pairs of adjacent tabs folded one over the other to form stacked stress-applying features.

Clause 74. The method of clause 73, wherein the adjacent tabs in the pairs of are arranged side-by-side on the scaffold prior to folding.

Clause 75. The method of clause 73, wherein the adjacent tabs in the pairs of are arranged in tandem on the scaffold prior to folding.

Clause 76. The method of clause 73, wherein the adjacent tabs in the pairs of are arranged on opposite sides of a strut prior to folding.

Clause 77. Apparatus for treating calcification on a wall in a patient's body lumen, said system comprising:

a catheter including a catheter body having a proximal end and a distal segment;

an expandable structure disposed at the distal segment of the catheter, said expandable structure having an outer surface configured to be displaced radially outwardly toward an inner surface of the body lumen wall; and a plurality of plaque-disrupting features distributed over the outer surface of the expandable structure, wherein at least some of the plaque-disrupting features are present on the outer surface of the expandable structure and have convex rounded upper surfaces configured to fracture the calcification while minimizing damage to the body lumen when the expandable structure is expanded within the body lumen.

Clause 78. Apparatus as in clause 77, wherein the body lumen comprises a blood vessel, a valve annulus, a venous valve, or AV shunt.

Clause 79. Apparatus as in clause 77 or 78, wherein the calcification is located within an inner wall, an intimal layer, a medial layer, an adventitial layer, a valve leaflet, valve annulus, venous filter, or an implant.

Clause 80. Apparatus as in any one of clauses 77 to 79, wherein the expandable structure is less rigid when not expanded and more rigid when fully expanded.

Clause 81. Apparatus as in any one of clauses 77 to 80, wherein the outer surface of the expandable structure is generally cylindrically when fully expanded.

Clause 82. Apparatus as in any one of clauses 77 to 81, wherein the convex rounded upper surfaces of plurality of plaque-disrupting features extend radially outwardly beyond the outer surface of the expandable structure when fully expanded.

Clause 83. Apparatus as in clause 82, wherein the convex rounded upper surfaces of plurality of plaque-disrupting features extend radially outwardly beyond the outer surface of the expandable structure by a distance in a range from 0.15 mm to 3 mm, preferably range from 0.25 mm to 3 mm more preferably ranging from 0.5 mm to 3 mm when fully expanded.

Clause 84. Apparatus as in any one of clauses 77 to 83, wherein the convex rounded upper surfaces of the plaque-disrupting features are free from edges and irregularities which could damage the wall when the expandable structure is expanded within the body lumen.

Clause 85. Apparatus as in any one of clauses 77 to 84, wherein at least some of the plaque-disrupting features have a single convex rounded upper surface and a lower base independently attached to the outer surface of the expandable structure.

Clause 86. Apparatus as in any one of any one of clauses 77 to 85, wherein at least some of the plaque-disrupting features comprise spheres, hemispheres, truncated spheres, or ellipsoids.

Clause 87. Apparatus as in any one of clauses 77 to 86, wherein at least some of the plaque-disrupting features are independently attached to the outer surface of the expandable structure.

Clause 88. Apparatus as in any one of clauses 77 to 87, wherein at least some of the plaque-disrupting features comprise hemispheres having lower surfaces attached to the outer surface of the expandable structure.

Clause 89. Apparatus as in clause 88, wherein the lower surfaces are flat.

Clause 90. Apparatus as in clause 88, wherein the lower surfaces are contoured.

Clause 91. Apparatus as in any one of clauses 77 to 88, wherein at least some of the plaque-disrupting features comprise posts having hemispherical upper surfaces and lower surfaces attached to the outer surface of the expandable structure.

Clause 92. Apparatus as in clause 77 to 91, wherein the plaque-disrupting features comprise a sharp element projecting outwardly from the convex rounded upper surface and wherein the sharp element is configured to concentrate stress when engaged against the calcification on the wall of a vascular lumen when the convex rounded upper surface is pressed against a surface of the calcification.

Clause 93. Apparatus as in clause 92, wherein the convex rounded upper surface extends above a surface of the scaffold by a first distance and the sharp element projects from the surface of the convex rounded upper surface by a second distance equal to 0.05 to 0.1 of the first distance.

Clause 94. Apparatus as in clause 92 or 93, wherein the second distance is in a range from 0.01 mm to 0.2 mm, or 0.01 mm to 0.1 mm.

Clause 95. Apparatus as in clause 92 to 94, wherein the sharp element comprises a point.

Clause 96. Apparatus as in clause 92 to 94, wherein the sharp element comprises an edge.

Clause 97. Apparatus as in any one of clauses 77 to 96, wherein the expandable structure comprises an inflatable balloon.

Clause 98. Apparatus as in clause 97, wherein the inflatable balloon has a central region, a distal tapered region, and a proximal tapered region and wherein the plaque-disrupting features are present on one or more of these regions.

Clause 99. Apparatus as in clause 97 or 98, wherein the plaque-disrupting features are present on at least the central region.

Clause 100. Apparatus as in clause 97 to 99, wherein the plaque-disrupting features are present on at least one of the distal and proximal tapered regions.

Clause 101. Apparatus as in clause 100, wherein the plaque-disrupting features are present on both of the distal and proximal tapered regions.

Clause 102. Apparatus as in clause 97 to 101, wherein the inflatable balloon has a distensibility below 10% when inflated to a pressure of at least 8 atm, at least 10 atm, at least 12 atm, at least 16 atm, at least 18 atm or at least 20 atm.

Clause 103. Apparatus as in any one of clauses 77 to 102, wherein the plaque-disrupting features are attached to the outer surface of the expandable structure by at least one of adhesive bonding, ultrasonic welding, heat welding, press fitting, solvent bonding, bonding with a polymeric material, use of a fastener, and combinations thereof.

Clause 104. Apparatus as in any one of clauses 77 to 103, further comprising an outer sleeve positioned over the plaque-disrupting features on the outer surface of the expandable structure.

Clause 105. Apparatus as in clause 104, wherein the outer sleeve comprises a retractable sheath configured to shield the plaque-disrupting features as the apparatus is advanced and/or retracted through the body lumen.

Clause 106. Apparatus as in clause 105, wherein the outer sleeve comprises an elastomeric tubular member positioned over the outer surface of the expandable structure and conforming to the plaque-disrupting features when the expandable structure is expanded, wherein the elastomeric tubular member is configured to expand and contract with the expandable structure.

Clause 107. Apparatus as in clause 104, wherein the elastomeric tubular member is laminated or attached to at least a portion of the outer surface of the expandable structure.

Clause 108. Apparatus as in clause 104, wherein the outer sleeve comprises a non-distensible or semi-compliant sheath folded over the balloon before the balloon is inflated.

Clause 109. Apparatus as in clause 104 to 108, wherein the outer sleeve fully covers the clot disruption features on the outer surface of the expandable structure.

Clause 110. Apparatus as in any one of clauses 104 to 109, wherein the outer sleeve comprises a polymer.

Clause 111. Apparatus as in clause 106 to 110, wherein at least some of the plaque-disrupting features are attached to an inner surface of the elastomeric tubular member.

Clause 112. Apparatus as in clause 111, wherein at least some of the plaque-disrupting features are formed as a protrusion from the inner surface of the elastomeric tubular member.

Clause 113. Apparatus as in any one of clauses 77 to 112, wherein at least some of the plaque-disrupting features have a base attached to the outer surface of the expandable structure, said base having a width in an axial direction (Wa) and a width in a circumferential direction (Wc) with a width ratio Wa:Wc in a range from 1:0.5 to 1:5; usually from 1:1 to 1 to 1:5; more usually from 1:1 to 3:1.

Clause 114. Apparatus as in clause 113, wherein at least some of the bases have a circular periphery.

Clause 115. Apparatus as in clause 113, wherein at least some of the bases have an oval periphery.

Clause 116. Apparatus of any one of clauses 77 to 115, wherein at least some of the plaque-disrupting features are arranged in diametrically opposed pairs.

Clause 117. Apparatus of clause 116, wherein successive diametrically opposed pairs of plaque-disrupting features are circumferentially offset.

Clause 118. Apparatus of clause 117, wherein the successive diametrically opposed pairs of plaque-disrupting features are circumferentially offset by an angle from 45° to 900.

Clause 119. Apparatus of any one of clauses 77 to 115, wherein at least some of the plaque-disrupting features are arranged in groups of three which are circumferentially separated about a circle on the surface of the expandable structure by about 120°.

Clause 120. Apparatus of any one of clauses 77 to 119, wherein the inflatable balloon is configured to release an inflation medium comprising a medicament in response to an inflation pressure above a minimum threshold value.

Clause 121. Apparatus of clause 120, wherein the minimum threshold value is above 3 atm, 5 atm, or 7 atm.

Clause 122. Apparatus of any one of clauses 120 to 121, wherein the inflatable balloon comprises a plurality of ports which open in response to the inflation pressure above the minimum threshold value.

Clause 123. A method for treating calcification on a wall in a patient's body lumen, said method comprising:
positioning an expandable structure at a treatment site proximate the calcification to be treated;
radially outwardly expanding the expandable structure to radially outwardly press a plurality of plaque-disrupting features against the calcification, wherein the plaque-disrupting features are distributed over the outer surface of the expandable structure and at least some of the plaque-disrupting features and have convex rounded upper surfaces and wherein radially outwardly pressing the plurality of plaque-disrupting fractures into the calcification fractures the calcification while reducing damage to the wall.

Clause 124. A method as in clause 123, wherein the body lumen comprises a blood vessel, a valve annulus, a venous valve, or AV shunt.

Clause 125. A method as in clause 123 or 124, wherein the calcification is located within an inner wall, an intimal layer, a medial layer, an adventitial layer, a valve leaflet, a valve annulus, a venous filter, or an implant.

Clause 126. A method as in any one of clauses 123 to 125, wherein the convex rounded upper surfaces of the plaque-disrupting features are free from edges and irregularities which could damage the vascular wall when the expandable structure is expanded within the body lumen.

Clause 127. A method as in clause 123 to 126, wherein the plaque-disrupting features comprise a sharp element projecting outwardly from the convex rounded upper surface and wherein the sharp element is configured to concentrate stress when engaged against the calcification on the wall of a vascular lumen when the convex rounded upper surface is pressed against a surface of the calcification.

Clause 128. A method as in clause 127, wherein the convex rounded upper surface extends above a surface of the scaffold by a first distance and the sharp element projects from the surface of the convex rounded upper surface by a second distance equal to 0.05 to 0.1 of the first distance.

Clause 129. A method as in clause 127 or 128, wherein the second distance is in a range from 0.01 mm to 0.2 mm, or 0.01 mm to 0.1 mm.

Clause 130. A method as in clause 127 to 129, wherein the sharp element comprises a point.

Clause 131. A method as in clause 127 to 129, wherein the sharp element comprises an edge.

Clause 132. A method as in any one of clauses 123 to 131, wherein expanding comprises inflating a balloon having the plurality of plaque disrupting features independently attached to an outer surface of the balloon.

Clause 133. A method as in any one of clauses 123 to 132, wherein at least some of the plaque-disrupting features comprise spheres or ellipsoids having lower surfaces attached to the outer surface of the expandable structure.

Clause 134. A method as in any one of clauses 123 to 132, wherein at least some of the plaque-disrupting features comprise hemispheres having lower surfaces attached to the outer surface of the expandable structure.

Clause 135. A method as in any one of clauses 123 to 132, wherein at least some of the plaque-disrupting features comprise posts having hemispherical upper surfaces and lower surfaces attached to the outer surface of the expandable structure.

Clause 136. A method as in any one of clauses 123 to 135, wherein the lower surfaces are attached directly to the outer surface of the expandable structure.

Clause 137. A method as in any one of clauses 123 to 135, wherein the lower surfaces comprise bases which are attached directly to the outer surface of the expandable structure.

Clause 138. A method as in any one of clauses 123 to 137, wherein at least some of the plaque-disrupting features have a base attached to the outer surface of the expandable structure, said base having a width in an axial direction (Wa) and a width in a circumferential direction (Wc) with a width ratio Wa:Wc in a range from 1:0.5 to 1:5; usually from 1:1 to 1 to 1:5; more usually from 1:1 to 3:1.

Clause 139. A method as in clause 138, wherein at least some of the bases have a circular periphery.

Clause 140. A method as in clause 138, wherein at least some of the bases have an oval periphery.

Clause 141. A method of any one of clauses 123 to 140, wherein at least some of the plaque-disrupting features are arranged in diametrically opposed pairs.

Clause 142. A method of clause 141, wherein successive diametrically opposed pairs of plaque-disrupting features are circumferentially offset.

Clause 143. A method of clause 142, wherein the successive diametrically opposed pairs of plaque-disrupting features are circumferentially offset by an angle from 45° to 900.

Clause 144. A method of any one of clauses 123 to 140, wherein at least some of the plaque-disrupting features are arranged in groups of three which are circumferentially separated about a circle on the surface of the expandable structure by about 120°.

Clause 145. A method as in any one of clauses 123 to 144, wherein radially outwardly expanding the expandable scoring structure comprises inflating an inflatable balloon.

Clause 146. A method as in clause 145, wherein the inflatable balloon has a distensibility below 10% when inflated to 8 atm, at least 10 at, at least 12 atm, at least 16 atm, at least 18 atm or at least 20 atm.

Clause 147. A method of any one of clauses 145 to 146, wherein the inflatable balloon is inflated to a pressure that presses the convex rounded upper surfaces of the plaque-disrupting features against the inner wall of the body lumen while not engaging the outer surface the inflatable balloon against the inner wall of the body lumen.

Clause 148. A method of any one of clauses 145 to 147, wherein prior to inflation, the inflatable balloon remains sufficiently flexible to be advanced through the body lumen.

Clause 149. A method as in any one of clauses 123 to 148, wherein the plaque-disrupting features are attached to the outer surface of the expandable structure by at least one of an adhesive, ultrasonic welding, heat welding, a fastener, solvent bonding, bonding with a polymeric material, or combinations thereof.

Clause 150. A method as in any one of clauses 123 to 149, further comprising an outer sleeve positioned over the plaque-disrupting features on the outer surface of the expandable structure.

Clause 151. A method as in clause 150, wherein the outer sleeve comprises a retractable sheath configured to shield the plaque-disrupting features as the expandable member is advanced and/or retracted through the body lumen.

Clause 152. A method as in clause 150, wherein the outer sleeve comprises an elastomeric tubular member positioned over the outer surface of the expandable structure and conforming to the plaque-disrupting features, wherein the elastomeric tubular member is configured to expand and contract with the expandable structure and the plaque-disrupting features remain configured to disrupt plaque when expanded against plaque.

Clause 153. A method as in clause 152, wherein the elastomeric tubular member is laminated to at least a portion of the outer surface of the expandable structure.

Clause 154. A method as in clause 150, wherein the outer sleeve comprises a non-distensible or semi-compliant sheath folded over the balloon before the balloon is inflated.

Clause 155. A method as in clause 123 to 154, wherein the outer sleeve fully covers the clot disruption features on the outer surface of the expandable structure.

Clause 156. A method as in clause 153 to 155, wherein at least some of the plaque-disrupting features plaque are attached to an inner surface of the elastomeric tubular member.

Clause 157. A method as in clause 156, wherein at least some of the plaque-disrupting features are formed as a protrusion from the inner surface of the elastomeric tubular member.

Clause 158. A method as in any one of clauses 123 to 155, wherein at least some of the plaque-disrupting features have a base attached to the outer surface of the expandable structure, said base having a width in an axial direction (Wa) and a width in a circumferential direction (Wc) with a width ratio Wa:Wc in a range from 1:0.5 to 1:5; usually from 1:1 to 1 to 1:5; more usually from 1:1 to 3:1.

Clause 159. A method as in clause 158, wherein at least some of the bases have a circular periphery.

Clause 160. A method as in clause 158, wherein at least some of the bases have an oval periphery.

Clause 161. A method of any one of clauses 123 to 160, wherein at least some of the plaque-disrupting features are arranged in diametrically opposed pairs.

Clause 162. A method of clause 161, wherein successive diametrically opposed pairs of plaque-disrupting features are circumferentially offset.

Clause 163. A method of clause 162, wherein the successive diametrically opposed pairs of plaque-disrupting features are circumferentially offset by an angle from 45° to 900.

Clause 164. A method of any one of clauses 123 to 160, wherein at least some of the plaque-disrupting features are arranged in groups of three which are circumferentially separated about a circle on the surface of the expandable structure by about 120°.

Clause 165. A method of any one of clauses 123 to 164, wherein plaque-disrupting features are arranged in a multiplicity circumferential ring patterns, wherein each ring pattern includes from 1 to 10 features, preferably ranges from 2 to 5 features, and more preferably ranges from 3 to 4 features.

Clause 166. A method of clause 165, wherein the circumferential ring patterns are axially spaced-apart over a length of the expandable structure and separated by gaps in a range from 0.1 mm to 3 mm.

Clause 167. A method of clauses 165 or 166, wherein the number of features ranges from 2 to 200 per mm of axial length.

Clause 168. A method of any one of clauses 123 to 167, further comprising releasing an inflation medium comprising a medicament through the inflatable balloon in response to an inflation pressure above a minimum threshold value.

Clause 169. A method of clause 168, wherein the minimum threshold value is above 3 atm, 5 atm, or 7 atm.

Clause 170. A method of clauses 168 or 169, wherein the inflatable balloon comprises a plurality of ports which open in response to the inflation pressure above the minimum threshold value.

Clause 171. Apparatus for treating a patient valve having calcified leaflets, said apparatus comprising:

a catheter body having a proximal end and a distal end; and a segmented balloon structure disposed at the distal end of the catheter body, said segmented balloon structure having opposed internal walls configured to be expanded on opposite surfaces of the leaflets to disrupt calcification on the calcified valve.

Clause 172. Apparatus of clause 171, wherein the opposed internal walls are configured to close together when the balloon structure is expanded.

Clause 173. Apparatus of clause 172, wherein the opposed internal walls are configured to nest when the balloon structure is expanded.

Clause 174. Apparatus of clause 173, wherein the nested opposed internal walls comprise nesting conical surfaces.

Clause 175. Apparatus of clause 172, wherein the opposed internal walls comprise flat surfaces that are configured to close against each other when the balloon structure is expanded.

Clause 176. Apparatus of clause 175, wherein the segmented balloon structure comprises a pair of opposed conical balloon having flat bases which comprise the flat surfaces.

Clause 177. Apparatus of clause 171 to 176, further comprising a plurality of calcification disruption features distributed over at least one of opposed internal walls of the segmented balloon structure.

Clause 178. Apparatus of clause 177, wherein the calcification disruption features are distributed over both of the opposed internal walls of the segmented balloon structure.

Clause 179. Apparatus of clause 177 or 178, wherein at least some of the calcification disruption features have convex rounded leaflet engaging surfaces configured to fracture the calcification while minimizing damage to the leaflet when the balloon structure is expanded in the patient valve.

Clause 180. Apparatus as in clause any one of clauses 177 to 179, wherein the convex rounded upper surfaces of plurality of plaque-disrupting features are configured to extend from the opposed internal walls of the expandable balloon when said balloon is inflated.

Clause 181. Apparatus as in clause 180, wherein the convex rounded upper surfaces extend from the opposed internal walls by a distance in a range from 0.1 mm to 3 mm, preferably ranging from 025 mm to 3 mm more preferably ranging from 0.5 mm to 3 mm, when said balloon is fully inflated.

Clause 182. Apparatus as in any one of clauses 204 to 206, wherein the convex rounded upper surfaces of the calcification disruption features are free from edges and irregularities which could damage the leaflets when the balloon structure is inflated within the patient valve.

Clause 183. Apparatus as in clause 179 to 182, wherein the calcification disruption features comprise a sharp element projecting outwardly from the convex rounded upper surface and wherein the sharp element is configured to concentrate stress when engaged against the calcification on the valve leaflet when pressed against a surface of the valve leaflet.

Clause 184. Apparatus as in any one of clauses 171 to 183, wherein the balloon segments are fixed on the catheter body with a fixed spacing between the opposed internal walls.

Clause 185. Apparatus as in any one of clauses 171 to 183, wherein the balloon segments are configured to axially translate relative to each other on the catheter body with a variable spacing between the opposed internal walls.

Clause 186. Apparatus as in any one of clauses 171 to 185, wherein the calcification disruption features on the opposing surfaces are axially aligned as the balloon segments are drawn together.

Clause 187. Apparatus as in any one of clauses 171 to 186, wherein the calcification disruption features on the opposing surfaces are laterally offset so that they do not align axially as the balloon segments are drawn together.

Clause 188. A method for treating a patient valve having calcified leaflets, said method comprising:

providing a catheter body having a segmented balloon structure disposed at a distal end thereof;

intravascularly advancing the segmented balloon structure to the patient valve; and expanding opposed internal walls of the segmented balloon on opposite surfaces of the leaflets to disrupt calcification on the calcified valve.

Clause 189. The method of clause 188, wherein the opposed internal walls are configured to close together when the balloon structure is expanded.

Clause 190. The method of clause 189, wherein the opposed internal walls are configured to nest when the balloon structure is expanded.

Clause 191. The method of clause 189, wherein the nested opposed internal walls comprise nesting conical surfaces.

Clause 192. The method of clause 189, wherein the opposed internal walls comprise flat surfaces that are configured to close against each other when the balloon structure is expanded.

Clause 193. The method of clause 192, wherein the segmented balloon structure comprises a pair of opposed conical balloon having flat bases which comprise the flat surfaces.

Clause 194. The method of clause 188 to 193, wherein a plurality of calcification disruption features are distributed over at least one of opposed internal walls of the segmented balloon structure.

Clause 195. The method of clause 194, wherein the calcification disruption features are distributed over both of the opposed internal walls of the segmented balloon structure.

Clause 196. The method of clause 188 to 195, wherein at least some of the calcification disruption features have convex rounded leaflet engaging surfaces configured to fracture the calcification while minimizing damage to the leaflet when the balloon structure is expanded in the patient valve.

Clause 197. The method as in clause any one of clauses 194 to 196, wherein the convex rounded upper surfaces of plurality of plaque-disrupting features are configured to extend from the opposed internal vails of the expandable balloon when said balloon is inflated.

Clause 198. The method as in clause 197, wherein the convex rounded upper surfaces of extend from the opposed internal walls by a distance in a range from 0.25 mm to 3 mm, preferably ranging from 0.5 mm to 3 nm, when said balloon is fully inflated.

Clause 199. The method as in any one of clauses 196 to 198, wherein the convex rounded upper surfaces of the calcification disruption features are free from edges and irregularities which could damage the leaflets when the balloon structure is inflated within the patient valve.

Clause 200. The method as in clause 196 to 198, wherein the calcification disruption features comprise a sharp element projecting outwardly from the convex rounded upper surface and wherein the sharp element is configured to concentrate stress when engaged against the calcification on the valve leaflet when pressed against a surface of the valve leaflet.

Clause 201. The method as in any one of clauses 188 to 200, wherein the balloon segments are fixed on the catheter body with a fixed spacing between the opposed internal walls.

Clause 202. The method as in any one of clauses 188 to 200, wherein the balloon segments are configured to axially translate relative to each other on the catheter body, further comprising moving the balloon segments together to compress the walls surfaces against the valve leaflets after the balloon structure is inflated.

Clause 203. A method for disrupting a calcification or plaque at a lesion, said method comprising:

advancing a sleeve over a wire through the lesion;

advancing an expandable member over the wire and into an interior of the sleeve; and expanding the expandable member within the sleeve to outwardly radially displace features on an inside and/or outside of the sleeve against the lesion to disrupt the calcification or plaque.

Clause 204. A method as in clause 203, further comprising removing the expandable member from the sleeve and removing the expandable member and the sleeve over the wire.

Clause 205. A method as in clause 204, wherein the expandable structure is a balloon or other expandable member.

Clause 206. A method as in clause 203, wherein the expandable structure comprises a stent and wherein the sleeve is left in place between the stent and the lesion after the stent is expanded.

Clause 207. A method as in any one of clauses 203 to 206, wherein the stress-applying features protrude radially outwardly from the sleeve into the vessel wall when the expandable structure displaces them radially outwardly upon expansion.

Clause 208. A method for disrupting a calcification or plaque at a lesion, said method comprising:

advancing a cage or basket over a wire across the lesion; and expanding the cage of basket to radially displace stress-applying features on the cage or basket against the lesion to disrupt the calcification or plaque.

Clause 209. The method of clause 208, wherein expanding the cage or basket comprises mechanically reorienting structural components of the cage or basket.

Clause 210. The method of clause 208, wherein expanding the cage or basket comprises inflating a balloon within the cage or basket.

Clause 211. The method of clause 210, wherein the balloon is advanced to the lesion together with the cage or basket.

Clause 212. The method of clause 210, wherein the balloon is advanced to the lesion together after the cage or basket.

Clause 213. Apparatus for treating calcification on a wall in a patient's body lumen, said apparatus comprising:

a catheter including a catheter body having a proximal end and a distal segment;

an expandable structure disposed at the distal segment of the catheter body, said expandable structure having an outer surface configured to be displaced radially outwardly toward an inner surface of the body lumen wall; and a plurality of plaque-disrupting features distributed over the outer surface of the expandable structure, wherein at least some of the plaque-disrupting features are disposed on the outer surface of the expandable structure and have a convex rounded apex configured to fracture the calcification while minimizing damage to the body lumen when the expandable structure is expanded within the body lumen;

wherein the convex rounded apex of the plaque-disrupting features has a radial height above the outer surface of the expandable structure in a range from a minimum of 0.05 mm, 0.1 mm, 0.15 mm, 0.2 mm, or 0.25 mm to a maximum of 1 mm, 0.5 mm, 0.4 mm, 0.3 mm, or 0.25 mm, and a distribution density in a range from 0.1 to 5 features/mm$^2$, preferably from 0.2 to 4 features/mm$^2$, more preferably from 0.25 to 3 features/mm$^2$ when the expandable structure is expanded.

Clause 214. Apparatus as in clause 213, wherein the plaque-disrupting features have a footprint having a maximum width, diameter, or other lateral dimension of 4 mm or less, often being 3 mm or less, more often being no more than 1 mm, and frequently being no more than 0.75 mm, and sometimes being no more than 0.5 mm.

Clause 215. Apparatus as in clause 213 or 214, wherein the plaque-disrupting features comprise any one or more of balls, spheres, hemispheres, domes, and ellipsoidal solids.

Clause 216. Apparatus as in clause 213 to 215, wherein the plaque-disrupting features are solid.

Clause 217. Apparatus as in clause 213 to 215, wherein the plaque-disrupting features are hollow.

Clause 218. Apparatus as in clause 213 to 217, further comprising an encapsulation layer covering the outer surface of the expandable structure and the plaque-disrupting features to immobilize the plaque-disrupting features in a desired pattern on the outer surface of the expandable structure.

Clause 219. Apparatus as in clause 218, wherein the plaque-disrupting features comprise discrete bodies.

Clause 220. Apparatus as in clause 219, wherein the discrete bodies comprise a metal.

Clause 221. Apparatus as in clause 218 to 220, wherein the plaque-disrupting features are immobilized solely by encapsulation layer.

Clause 222. Apparatus as in clause 218 to 220, wherein the plaque-disrupting features are immobilized by an adhesive between the feature and the outer surface in addition to the encapsulation layer.

Clause 223. Apparatus as in clause 218 to 222, wherein the encapsulation layer encapsulates the entire plaque-disrupting feature including the convex rounded apex.

Clause 224. Apparatus as in clause 218 to 222, wherein the encapsulation layer encapsulates only a lower portion of the plaque-disrupting feature excluding the convex rounded apex.

Clause 225. Apparatus as in clause 213 to 224, wherein the plaque-disrupting feature is cradled in an indentation in the outer surface of the expandable structure.

Clause 226. Apparatus as in clause 213 to 225, wherein encapsulation layer comprises a polymer selected from the group consisting of thermoplastic fluoropolymers (PVDF), butyl methacrylates (PBMA), and thermoplastic polyesters (PLLA).

Clause 227. Apparatus as in clause 218 to 226, wherein the encapsulation layer is applied over the outer surface and the plaque-disrupting features by any one of coating, direct fluid application, laminating, and fusing.

Clause 228. Apparatus as in clause 218 to 227, wherein the encapsulation layer has a thickness in a range from 0.01 mm to 0.1 mm (0.4 mil to 4 mil), often being 0.01 mm to 0.05 mm (0.4 mil to 2 mil), and more often being 0.01 mm to 0.02 mm (0.4 mil to 0.8 mil).

Clause 229. Apparatus as in clause 213 to 228, wherein the plaque-disrupting features are disposed in a recess formed in the outer surface of the expandable structure.

Clause 230. Apparatus as in clause 213 to 229, wherein the plaque-disrupting features are constrained over the outer surface of the expandable structure by an elastic sleeve.

Clause 231. Apparatus as in clause 230, wherein the plaque-disrupting features are further attached to the outer surface of the expandable structure.

Clause 232. Apparatus as in clause 230, wherein the plaque-disrupting features are attached to an inner surface of the elastic sleeve.

Clause 233. Apparatus as in clause 213 to 228, wherein the plaque-disrupting features are hollow and mounted on a post projecting radially outwardly from the outer surface of the expandable structure.

Clause 234. Apparatus for treating calcification on a wall in a patient's body lumen, said apparatus comprising:
  a catheter including a catheter body having a proximal end and a distal segment; an expandable structure disposed at the distal segment of the catheter body, said expandable structure having an outer surface configured to be displaced radially outwardly toward an inner surface of the body lumen wall;
  a plurality of plaque-disrupting features distributed over the outer surface of the expandable structure, wherein at least some of the plaque-disrupting features are present on the outer surface of the expandable structure and have an upper surface configured to fracture the calcification while minimizing damage to the body lumen when the expandable structure is expanded within the body lumen; and
  an encapsulation layer covering at least a portion of the outer surface of the expandable structure and the plaque-disrupting features to immobilize the plaque-disrupting features in a desired pattern on the outer surface of the expandable structure.

Clause 235. Apparatus as in clause 234, wherein at least some of the upper surfaces of the plaque-disrupting features comprise a convex rounded apex.

Clause 236. Apparatus as in clause 234 or 235, wherein the encapsulation layer covers the entire outer surface of at least some the plaque-disrupting features including the upper surface.

Clause 237. Apparatus as in clause 234 or 235, wherein the encapsulation layer cover only a lower portion of the outer surface of at least some of the plaque-disrupting features.

Clause 238. Apparatus as in clause 234 to 237, wherein the plaque-disrupting feature is disposed in an indentation on the outer surface of the expandable structure.

Clause 239. Apparatus as in clause 234, wherein the plaque-disrupting feature comprises a hemisphere with a flat bottom adhered to the outer surface of the expandable structure.

Clause 240. Apparatus as in clause 234 to 239, wherein the plaque-disrupting features comprise discrete bodies.

Clause 241. Apparatus as in clause 240, wherein the discrete bodies comprise a metal.

Clause 242. Apparatus as in clause 234 to 240, wherein the plaque-disrupting features comprise any one or more of a ball, a sphere, a hemisphere, an ellipsoidal solid, and a dome.

Clause 243. Apparatus as in clause 234 to 242, wherein the plaque-disrupting features are immobilized solely by encapsulation layer.

Clause 244. Apparatus as in clause 234 to 243, wherein the plaque-disrupting features are immobilized by an adhesive between the feature and the outer surface in addition to the encapsulation layer.

Clause 245. Apparatus as in clause 234 to 244, wherein encapsulation layer comprises a polymer selected from the group consisting of thermoplastic fluoropolymers (PVDF), butyl methacrylates (PBMA), and thermoplastic polyesters (PLLA).

Clause 246. Apparatus as in clause 234 to 245, wherein the encapsulation layer is applied over the outer surface and the plaque-disrupting features by any one of coating, direct fluid application, laminating, and fusing.

Clause 247. Apparatus as in clause 234 to 246, wherein the encapsulation layer has a thickness in a range from 0.01 mm to 0.1 mm (0.4 mil to 5 mil), often being 0.01 mm to 0.05 mm (0.4 mil to 2 mil), and more often being 0.01 mm to 0.02 mm (0.4 mil to 0.8 mil).

Clause 248. Apparatus as in clause 234 to 247, wherein the convex rounded apex of the plaque-disrupting features has a radial height above the outer surface of the expandable structure in a range from a minimum of 0.05 mm, 0.1 mm, 0.15 mm, 0.2 mm, or 0.25 mm to a maximum of 1 mm, 0.5 mm, 0.4 mm, 0.3 mm, or 0.25 mm, and a distribution density in a range from 0.1 to 5 features/mm$^2$, preferably from 0.2 to 4 features/mm$^2$, more preferably from 0.25 to 3 features/mm$^2$ when the expandable structure is expanded.

Clause 249. Apparatus as in clause 248, wherein the plaque distribution feature has footprint having a maximum width, diameter, or other lateral dimension of 4 mm or less, often being 3 mm or less, more often being no more than 1 mm, and frequently being no more than 0.75 mm, and sometimes being no more than 0.5 mm.

Clause 250. A method for treating a lesion on a wall in a patient's body lumen, said apparatus comprising:
  providing a catheter having an expandable structure disposed at a distal end thereof, said expandable structure having an outer surface configured to be displaced radially outwardly toward an inner surface of the body lumen wall, wherein the outer wall has a plurality of space-separating features distributed over the outer surface of the expandable structure; and expanding the expandable structure in the patient's body lumen such that a radially outward force is applied by the outer surface and the features against the wall while the features maintain a gap between the outer surface of the expandable structure and the inner wall.

Clause 251. A method as in clause 250, wherein the spacer features have axially aligned through holes permitting the passage of contrast media therethrough.

Clause 252. A method as in clause 277 or 278, wherein the gap allows fluid perfusion therethrough and past the expandable structure while the expandable structure is expanded.

Clause 253. A method as in clause 277 or 278, further comprising perfusing a drug into the gap while the expandable structure is expanded.

Clause 254. A method as in clause 253, wherein the expandable structure comprises a balloon and the drug is perfused through a wall of the balloon.

Clause 255. A method as in clause 254, wherein at least some of the space-separating features comprise a drug which is released into the gap.

Clause 256. A method as in clause 250 to 255, wherein expanding the expandable structure creates one or more gaps between the outer surface of the expandable structure and the inner wall under physiological pressure to allow fluid perfusion through the one or more gaps.

Clause 257. A method as in clause 250 to 256, wherein the body lumen comprises a blood vessel and the body fluid perfusion comprises blood.

Clause 258. A method as in clause 257, wherein the body fluid perfusion further comprises at least one of a contrast media and a drug.

Clause 259. A method as in clause 250 to 258, wherein at least some of the features have a convex rounded apex.

Clause 260. A method as in clause 250 to 259, wherein the features have a radial height above the outer surface of the expandable structure in a range from a minimum of 0.05 mm, 0.1 mm, 0.15 mm, 0.2 mm, or 0.25 mm to a maximum of 1 mm, 0.5 mm, 0.4 mm, 0.3 mm, or 0.25 mm, and a distribution density in a range from 0.1 to 5 features/mm$^2$, preferably from 0.2 to 4 features/mm$^2$, more preferably from 0.25 to 3 features/mm$^2$ when the expandable structure is expanded.

Clause 261. A method as in clauses 250 to 260, wherein the expandable structure is expanded with a force sufficient to create and/or maintain one or more gaps against a physiologic pressure from 0.5 psi to 5 psi, preferably from 1 psi to 3 psi.

Clause 262. A method as in clauses 250 to 261, wherein the features are configured to create and/or maintain the one or more gaps by separating the lesion from the outer surface of the expandable structure adjacent to the features when the structure is in the expanded configuration.

Clause 263. A method as in clauses 250 to 262, wherein the feature comprises a plurality of features positioned in a configuration around the circumferential length and/or axial length of the expandable structure to provide, create, or maintain said gaps.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 2F-1A to 2F-3B illustrate additional configurations examples of the stress-applying features of the present invention.

FIGS. 2G-1A to 2G-4B illustrate examples of the placement of points, edges, and other sharp features on the stress-applying features of the present invention.

FIGS. 2H-1 to 2H-22 illustrate a variety of design examples for the stress-applying features of the present invention.

FIG. 3 illustrates an expandable sleeve example having a helical pattern of stress-applying features on an outer surface thereof.

FIGS. 4A and 4B illustrate a tubular scaffold or sleeve having a first arrangement of stress-applying features on an outer surface thereof.

FIGS. 5A and 5B illustrate a tubular scaffold or sleeve having a second arrangement of stress-applying features on an outer surface thereof.

FIGS. 14A and 14B illustrate a spherical plaque-disrupting feature in accordance with the principles of the present invention mounted in a circular base (FIG. 14A) and a cylindrical base (FIG. 14B) present on an outer surface of an angioplasty balloon.

FIG. 15 illustrates exemplary peripheral dimensions for the plaque-disrupting feature and/or supporting base of the present invention.

FIGS. 16D-1 to 16D-6 illustrate exemplary attachment methods for spherical, conical other plaque-disrupting features in accordance with the principles of the present invention, wherein the features are attached in preformed indentations in an outer surface of a balloon or other expandable member which provides a receptacle or "cradle" for immobilizing the feature using one or more adhesive or polymeric materials. FIG. 16D-1 is a perspective view. FIG. 16D-2 is a cross-sectional view of the balloon, and FIGS. 16D-3 to 6 are detailed views of the features in the indentations, taken along lines 1603-1603, 1604-1604, 1605-1605, and 1606-1606 in FIG. 16D-2, respectively. These examples are similar to that illustrated in FIG. 16D.

FIGS. 18A to 18C illustrate attachment of spherical plaque-disrupting features on an inner surface of an elastic sleeve and methods for expansion using an inflatable balloon.

FIG. 19 illustrates plaque-disrupting features present on an outer surface of a drug delivery balloon catheter.

FIGS. 20A and 20B are cross-sectional views of the drug delivery balloon catheter of FIG. 19 shown in pre-inflated and post-inflated configurations, respectively, as used in drug delivery.

FIG. 22 illustrates the plaque-disrupting features of the present invention placed on an exterior of a balloon-expandable scaffold or "cage" of a type intended for temporary placement in a target vascular location for plaque-disrupting and subsequent removal.

FIG. 23A shows the placement of the expandable scaffold of FIG. 22 on a balloon catheter prior to expansion of the balloon catheter.

FIG. 23B shows the expandable scaffold of FIG. 23A on the balloon catheter following expansion of the balloon catheter.

FIGS. 24A to 24D are cross-sectional views of an expandable structures, such as a balloon catheter, having features, such as metal spheres, contacting and/or expanding plaque tissue, showing different distribution patterns for the features, for example having spaces created for fluid and/or contrast material to pass through between an outer surface of the expanded structure and an inner surface of the vessel (or plaque) by the features, such as metal spheres.

FIGS. 24D-1 to 24D-3 illustrate features of the type illustrated in FIG. 24D having holes though the features which further promote perfusion of contrast media past balloons when inflated in the vasculature.

FIGS. 27, 28, 29, 30A, 30B, 31A and 31B illustrate different embodiments of a catheter having a segmented balloon design or multi-balloon design with opposed surfaces with plaque-disrupting feature configured to capture cardiac or other valve leaflets to disrupt calcification of the patient valve.

DETAILED DESCRIPTION OF THE INVENTION

Figure 1A:
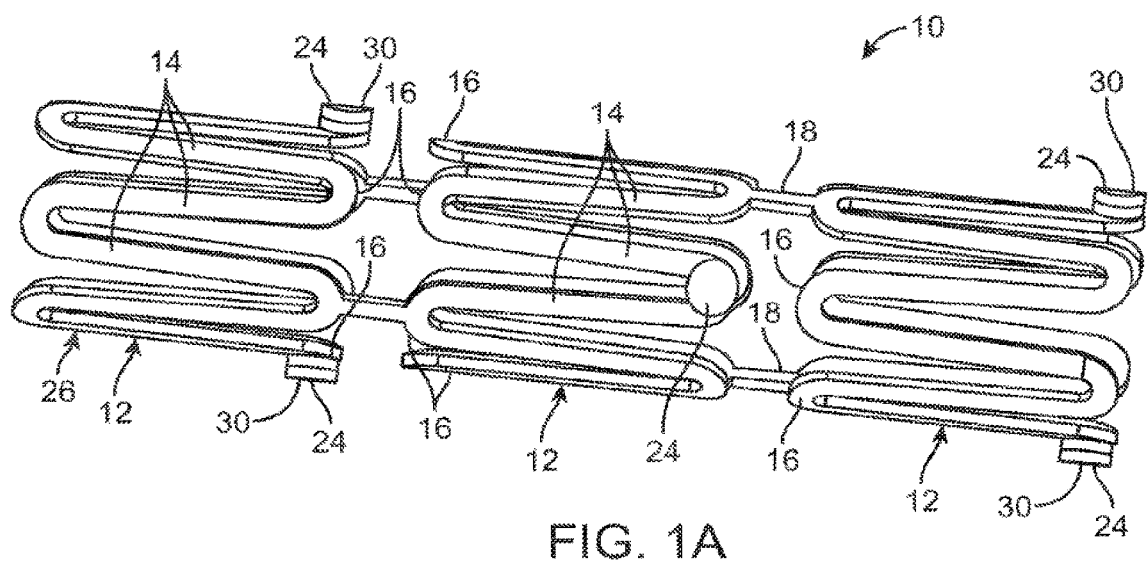
FIGS. 1A and 1B illustrate a scaffold having a plurality of stress-applying features distributed over an outer surface thereof in accordance with the principles of the present invention.
Figure 1B:
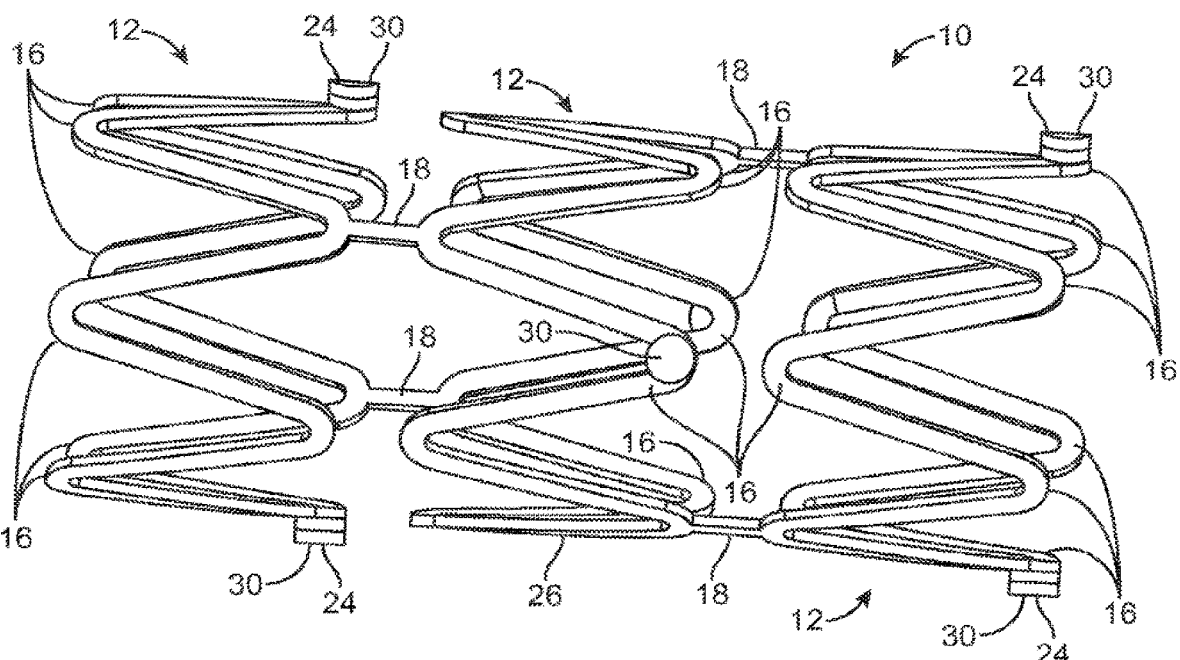

Referring to FIGS. 1A and 1B, an expandable structure comprising an endoluminal prosthesis comprises a radially expanding scaffold 10, illustrated in the form of a stent including a plurality of ring structures 12. The stent scaffold 10, as illustrated in FIGS. 1A and 1B, includes three discrete circumferential rings 12 joined by axial links 18 which together form a cylindrical or other envelope having free ends. While three rings are illustrated, it will be appreciated that stent scaffolds according to the present invention may comprise anywhere from a single circumferential ring structure to as many as 5, 10, or even more ring structures. The ring structures are usually joined into cylinders having generally circular cross-sectional shapes, but may other tubular geometries such as ellipsoidal, tapered, hourglass shaped, dog-bone shaped, oblong, other, and the like, as are well known in the art of vascular and other intraluminal scaffolds.

Each of the ring structures 12 comprises a plurality of struts, 14, usually straight struts, joined by U-shaped or other crowns 16. While such "serpentine" ring structures are most common in the fabrication of vascular stents, other geometries including zig-zag rings, spiral wire, helical wire, wire bent, diamond-shaped cells, other, and the like, are also well known in the vascular stent art and could be used in the present invention.

As shown in FIG. 1A, the scaffold 10 will initially be in a "crimped" or small configuration, i.e. having a narrow profile suitable for introduction to a patient's blood vessel or other body lumen. Once in place, the scaffold 10 will be caused to assume a radially expanded profile, as shown in FIG. 1B. Such radial expansion can be affected in any conventional manner, typically by balloon expansion or by "self-expansion" where an elastic stent is initially radially compressed and subsequently released from compression to allow expansion at a target location in the vasculature or other body lumen.

Of particular interest to the present invention, the scaffolds 10 of the present invention will have a plurality of stress-applying features 24 over their outer surfaces 26. The stress-applying features 24 may be pre-formed and attached to the outer surface of the scaffold after the scaffold has been separately fabricated, e.g., by gluing with an adhesive, soldering, welding, mechanical crimping, press fit, threaded attachment, or the like. Alternatively, the stress-applying features may be formed as part of the scaffold during fabrication of the scaffold, e.g., by cutting, machining, deposition, deformation, or combinations thereof. Particular methods for forming the stress-applying features are described with reference to FIGS. 6A to 6C, 7A to 7C, and 8A to 8C.

As shown FIGS. 1A and 1B, the stress-applying features 24 are disk-shaped and have generally circular blunt contact regions 30 on their radially outwardly exposed surfaces. Although generally preferred, such stress-applying figures may have a variety of other geometries some of which are described throughout the present invention with reference to FIGS. 2A to 2E, FIG. 2F, FIG. 2G, and FIG. 2F.

While some of the stress-applying features and/or plaque-disrupting features described herein are illustrated together with specific radially expanding scaffolds, such as stents, sleeves, balloons, valvuloplasty balloons, and the like, it should be appreciated that the stress-applying features and plaque-disrupting features described herein will be useful with and/or apply to at least some or any radially expanding structure, including at least balloons, stents, sleeves, valvuloplasty balloons and the like.

As further shown in FIGS. 1A and 1B, the stress-applying features 24 are attached over "free" ends of crowns 16 located on opposite sides of a ring structure 12. By "free" ends, it is meant that the crowns are free from attachment to adjacent crowns or other structure of the scaffold 10.

Successive pairs of stress-applying features 24 are located 180 apart on each ring structures 12, but the alignment is typically staggered by 90° on each successive ring 12. While a preferred arrangement, it will be appreciated that the number of and arrangements of individual stress-applying features 24 may vary widely as described previously in the present application.

Figure 2A:
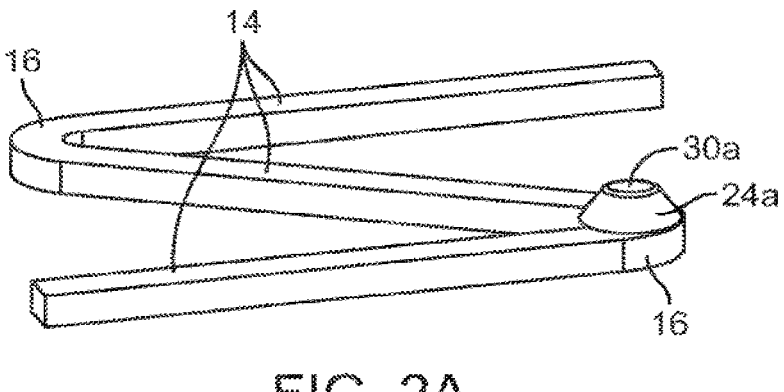
FIGS. 2A to 2E illustrate different designs examples for and locations examples of the stress-applying features of the present invention.

As shown in the examples of FIGS. 2A through 2E, the geometry and position of the stress-applying feature may vary significantly. As shown in FIG. 2A, a stress-applying feature 24a may be shaped as a truncated cone with the truncation forming a blunt contact region 30a.

Figure 2B:
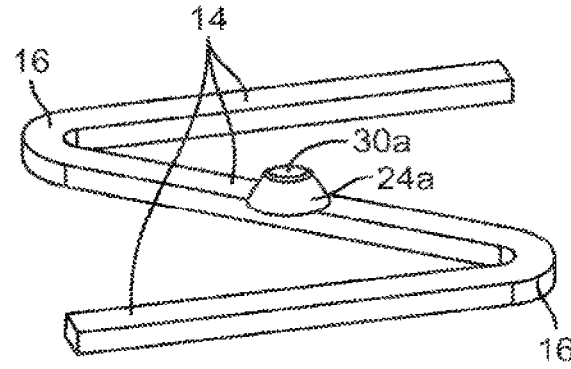

As shown in the example of FIG. 2B, the truncated cone 24a may be positioned on a strut 14, e.g., at a center of the strut. Additionally or alternatively, stress-applying features can be positioned anywhere along a strut length as well as at different locations on an individual scaffold 10, including crowns, struts, links, and the distribution of individual stress-applying features may vary over different axial and circumferential regions of the outer scaffold surface.

Figure 2C:
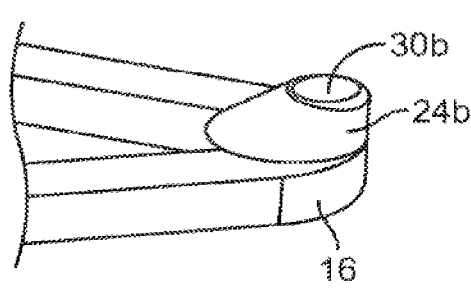
Figure 2D:
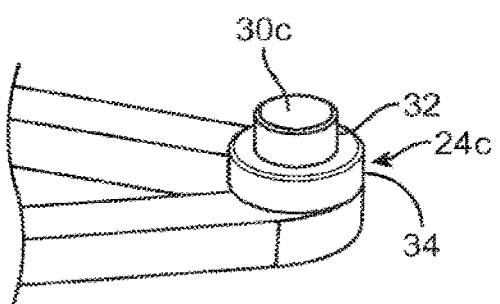
Figure 2E:
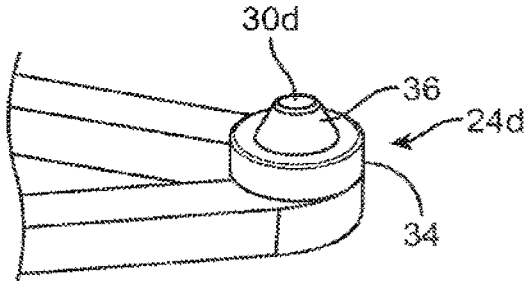

Referring now to FIGS. 2C through 2E the geometry of individual stress-applying features 24b to 24d may vary. For example, as shown in FIG. 2C, a stress-applying feature 24b may be formed asymmetrically as a truncated cone having a blunt contact region 30b displaced into alignment with an outer distal tip of the crown 16. As shown in FIG. 2D, a stress-applying feature 24c may be formed as two or more stacked disks or other stacked features having other shapes, where each of the stack features may have the same or a different configuration, for example including a larger diameter base disk 34 and a smaller diameter upper disk 32 with a blunt contact region 30c on the exposed surface of a smaller diameter upper disk 32. As shown in FIG. 2E, the larger diameter base disk 34 can be combined with a smaller upper truncated cone 36 with blunt contact region 30d formed by the truncation. The one or more features may also be convex, rounded, blunt, and/or atraumatic type shaped as described in this invention.

In most cases, the blunt contact region 30 is located at or near a top of the stress-applying feature 24, i.e., the most radially outward location on the outer surface of the scaffold (or other expandable balloon, sleeve, or the like, as discussed below). As such, the blunt contact regions 30 will be the first regions on a scaffold 10 to engage any occlusive material present on the inner wall of the blood vessel or other body lumen when the scaffold is radially expanded therein, as explained further with reference to FIGS. 9A and 9B, below.

Figures 1A, 2F:
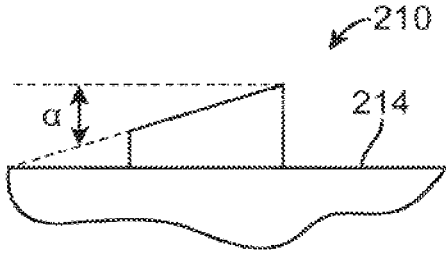
Figures 1B, 2F:
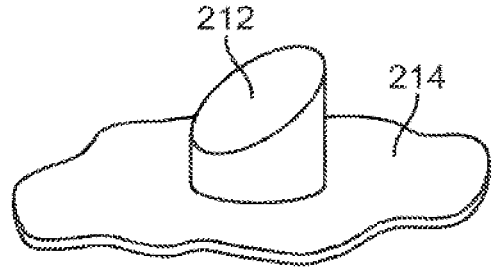
Figures 2A, 2F:
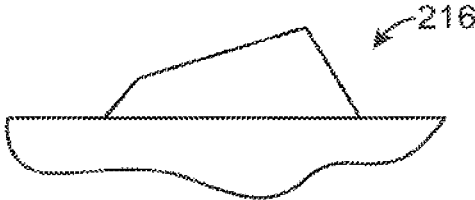
Figures 2B, 2F:
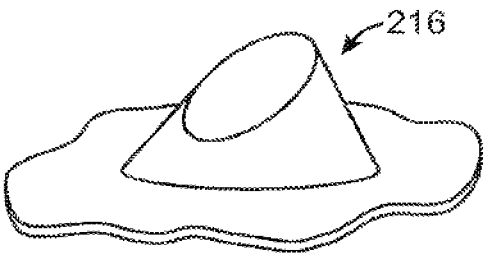

As described at this point, the stress-applying features of the present invention have been shown to have blunt contact regions which are generally parallel the surfaces upon which they are mounted. In other instances, the blunt contact regions may be inclined relative the surfaces upon which they are mounted. As shown in FIGS. 2F-1A/1B, an exemplary disk-like stress-applying feature 210 has a blunt contact region 212 inclined at an angle α relative to the surface 214 upon which is mounted. Angle α is typically in a range from 5° to 45°, usually being from 10° to 35°. A conical stress-applying feature 216 as well as a stacked stress-applying feature 218 may also have inclined contact regions, as shown in FIGS. 2F-2A/2B and 3A/3B, respectively.

Figures 2, 2F, 3, 3A:
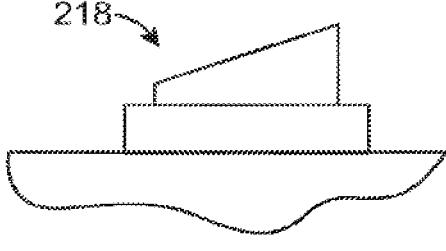
Figures 2, 2F, 3, 3B:
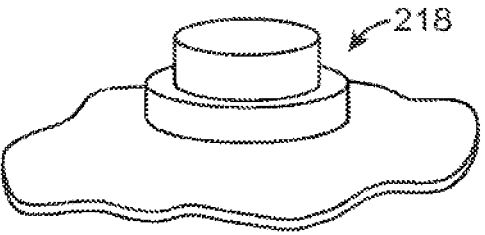
Figures 1A, 1B, 2, 2A, 2B, 2G, 3, 3A, 3B, 4, 4A, 4B:
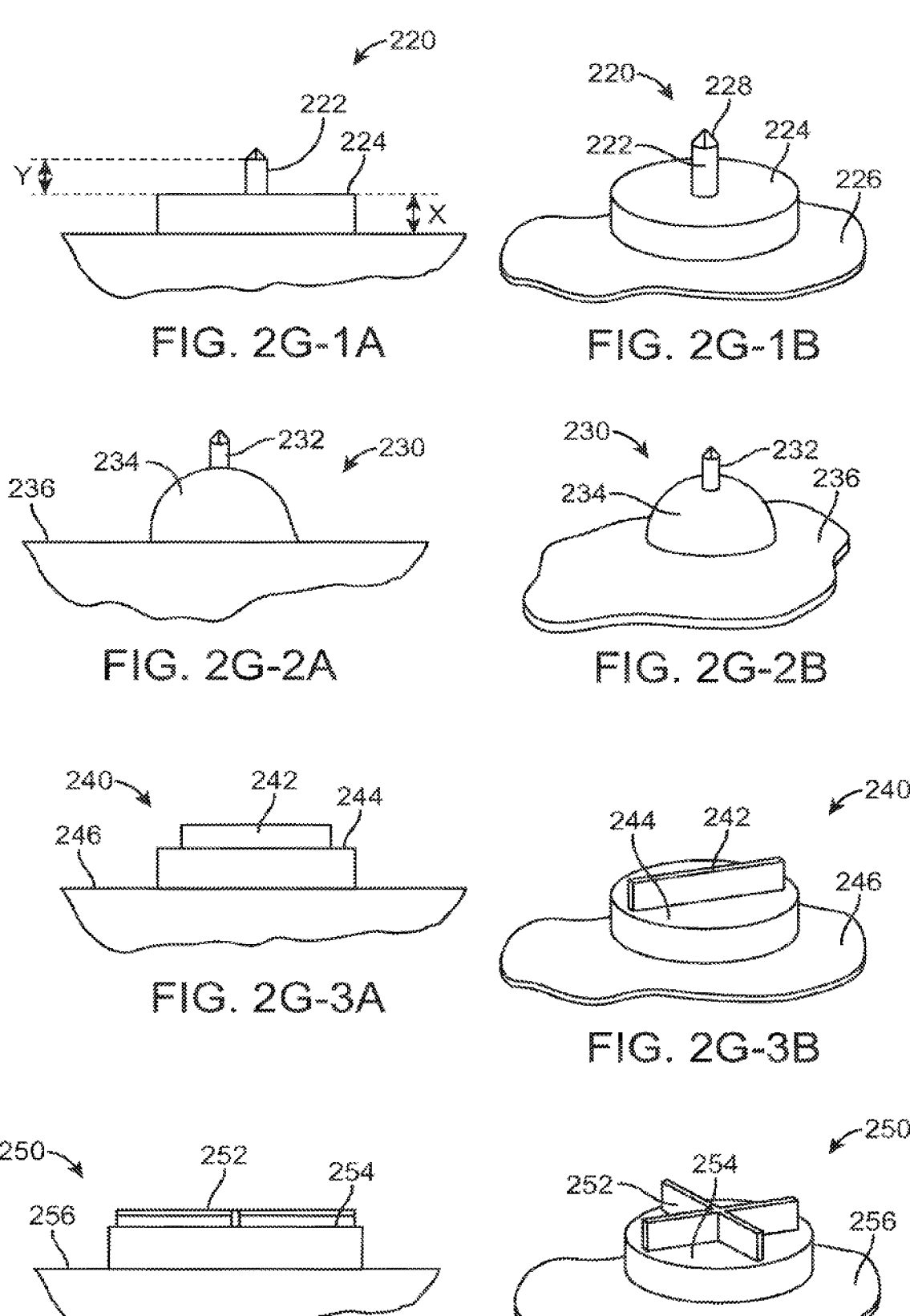

As shown in FIGS. 2G-1A and 2G-1B, an exemplary stress-applying feature 220 includes a sharp element 222 mounted on and projecting upwardly from a blunt contact region 224. The stress-applying feature 220 may be mounted on a surface 226 of any one of a scaffold, a sleeve, or an angioplasty or other balloon, as described in detail elsewhere herein. The sharp element 222 typically comprises a short shaft having a pointed tip 228 configured to initiate disruption of plaque or calcification as the stress-applying feature is pressed against the plaque or calcification. Preferred dimensions for the sharp element are provided elsewhere herein As shown in FIGS. 2G-2A and 2G-2B, a stress-applying feature 230 comprises a dome-like or hemispherical body with a rounded upper surface 234 for engaging plaque or calcification, as described in detail elsewhere herein. A sharp element 232 projects upwardly from the rounded upper surface 234, typically from the apex of the rounded upper surface. The stress-applying feature 230 is mounted on a surface to 236 of a scaffold, sleeve, balloon, or other structure as described in more detail elsewhere herein. The sharp element 232 is a short shaft having a pointed distal tip, similar to the sharp element 222.

The sharp elements may also comprise blades having one or more elongate sharp edges for initiating the calcification disruption. As shown in FIGS. 2G-3A and 3B, a stress-applying feature 240 comprises a disc-like blunt contact region 244 having a sharp element 242 projecting upwardly therefrom. The sharp element 242 consists of a single blade having a sharp edge, and the stress-applying feature is mounted on a surface 246 of a scaffold, balloon, cage, or sleeve as with other embodiments herein. As shown in FIGS. 2G-4A and 4B, a stress-applying feature 250 may comprise a disk-like blunt contact region 254 with a sharp element 252 including a pair of sharpened blades. As with previous embodiments, the stress-applying feature 250 is configured to be mounted on a surface 256 of a scaffold, balloon, cage, or sleeve.

The stress-applying features of the present invention may have any one of a variety of forms and designs, including blunt tissue-engagement surfaces, curved tissue-engagement surfaces, stacked-tissue engagement structures, segmented tissue-engagement structures, and the like, and a number of specific designs have already been shown and described. A number of additional, exemplary designs are shown in FIGS. 2H-1 to 2H-22, as will now be described. All specific stress-applying feature designs illustrated herein, including but not limited to those shown in FIGS. 2F-1A through 2H-22. May be used with any of the expandable structures describe herein, including but not limited to scaffolds, balloons, sleeves, cages, prosthetic valves, cages, and the like.

Figures 1, 2, 2H, 3:
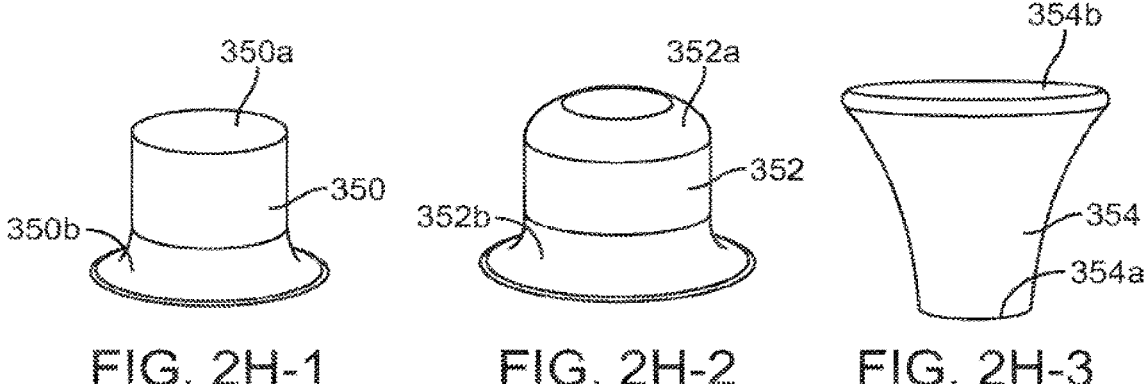

Stress-applying features comprising cylindrical posts are shown in FIGS. 2H-1 and 2H-2. FIG. 2H-1 illustrates a cylindrical post 350 having a flat cylindrical top 350a and a flared base 350b configured for attachment to an outer surface of a radially expanding structure. The flared base increases the surface area available for attachment to the surface of the expandable structure. The flat cylindrical top may have a peripheral edge (as shown) but in other instances may have rounded or beveled peripheral edge (not shown). The contact region of the cylindrical top may be coated with a material to provide one or more of an adherent (increased friction) surface, a smooth surface, a low-friction surface, or the like. Material can be bonded, fused, coted, laminated, or otherwise added to the surface to modify the surface geometry, e.g., make the surface flatter, more rounded, add texture, or the like. FIG. 2H-2 illustrates a cylindrical post 352 having a domed top 352a and a flared base 352b configured for attachment to an outer surface of a radially expanding structure.

Exemplary stress-applying features comprising tapered cylindrical posts are shown in FIGS. 2H-3 and 2H-4. FIG. 2H-3 illustrates a post 354 having a flat, circular bottom 354a which tapers radially outwardly in an upward direction to a flat circular top 354b that is larger than the bottom. FIG. 2H-4 illustrates a post 356 having a flat, round bottom 356a which tapers radially inwardly in an upward direction to a flat round top 356b that is smaller than the bottom.

Exemplary stress-applying features comprising stacked structures having an upper spherical or near-spherical plaque-engaging element and a variety of lower supporting elements are illustrated in FIGS. 2H-5 to 2H-9. FIG. 2H-5 illustrates a stress-applying feature 360 having a lower spherical support element 360a and an upper spherical plaque-engaging element 360b. FIG. 2H-6 illustrates a stress-applying feature 362 having a lower truncated conical element 362a and an upper spherical plaque-engaging element 362b. The truncated conical element 326a may provide an additional plaque disruption feature where a truncated top 362c can have a flat surface or other type of surface to contact a hardened plaque tissue. FIG. 2H-7 illustrates a stress-applying feature 364 having a lower truncated spherical support element 364a and an upper spherical plaque-engaging element 364b. A truncated top 364c of the truncated spherical element 364a may provide an additional plaque disruption feature to contact a hardened plaque tissue. FIG. 2H-8 illustrates a stress-applying feature 366 having a lower domed support element 366a and an upper spherical plaque-engaging element 366b. FIG. 2H-9 illustrates a stress-applying feature 368 having a lower support post 368a which has a reduced waist diameter (a "concaved" midsection) and an upper spherical plaque-engaging element 368b.

Stress-applying features comprising stacked structures having an upper dome-like plaque-engaging element and a variety of lower supporting elements are illustrated in FIGS. 2H-10 to 2H-13. FIG. 2H-10 illustrates a stress-applying feature 370 having a lower spherical support element 370a and an upper dome-like plaque-engaging element 370b. FIG. 2H-11 illustrates a stress-applying feature 372 having a lower truncated hemispherical element 372a and an upper partial spherical plaque-engaging element 372b which together form an integrated dome structure. Typically, the upper and lower elements will be formed from the different materials and/or will have different hardness's or other material properties, but in some instances may be formed from the same materials having similar or identical material properties. FIG. 2H-12 illustrates a stress-applying feature 374 having a lower support post 374a which is tapered about its midsection and an upper dome-like plaque-engaging element 374b. FIG. 2H-13 illustrates a stress-applying feature 376 having a lower truncated, tapered conical supporting element 376a and an upper dome-like plaque-engaging element 376b.

FIG. 2H-14 illustrates a stress-applying feature 378 which comprises a monolithic dome 378a having rounded top 378b asymmetrically positioned relative to a circular or ovoid-perimetered base 378c.

Stress-applying features having channeled plaque-engaging element and a variety of lower supporting elements are illustrated in FIGS. 2H-15 to 2H-18. FIG. 2H-15 illustrates a stress-applying feature 380 having an integrated structure, similar to that shown in FIG. 2H-11, with orthogonally oriented channels 380a and 380b dividing the structure into four symmetric quadrants. FIG. 2H-16 illustrates a stress-applying feature 382 comprising a cylindrical post 382a with orthogonally oriented channels 382b and 382c dividing the structure into four symmetric quadrants. The top of each quadrant includes smaller features 382d which assist in gripping and fracturing clot engaged by the post. FIG. 2H-17 illustrates a stress-applying feature 384 comprising a cylindrical post 384a similar to that illustrated in FIG. 2H-16 with orthogonally oriented channels 384b and 384c dividing the structure into four symmetric quadrants. Such channels, gaps, or spacers may be oriented axially along the axial length of the expandable structure and allow for medicaments or contrast agents to flow past the expandable structure in a direction from a proximal region to a distal region thereof under, at, or above physiologic pressures and conditions when such medicaments or contrast media is injected proximally to the expandable structure when the structure is expanded or inflated to the expanded inflated configuration.

In yet another alternative example (not shown), the features being hollow or solid such as a sphere is inserted inside the post and is secured by glue or other adhesive material to the inner surface of the post. This provides additional securing of the feature to the expandable structure surface, while providing hardened features such as formed from a metal or metal alloy to disrupt plaque when the expandable structure is expanded pushing the features against plaque or hardened tissue while the feature being encapsulated by the expandable structure outer surface. In yet another alternative or example (not shown), the feature comprises a hole through the feature extending axially and/or circumferentially to the expandable structure axial or circumferential direction, wherein the features hole forms a cavity in the base of the feature and wherein post 260 of the outer surface of the expandable structure protrudes into said cavity. The post in such example would optionally be glued to the cavity surface of the feature to provide further securement of the feature to the expandable structure post. The post may be pre-formed, e.g., molded as part of the balloon or other substrate 254 or may be separately formed and attached to the balloon, or may be formed or molded in the balloon outer surface when the balloon is in the expanded configuration after forming the balloon. The top of each quadrant includes smaller features 384c which assist in gripping and fracturing clot engaged by the post 384b which is mounted on a flared base 384d. The channels 384b and 384c provide a path for fluid to pass through when the expandable structure is in the expanded configuration. FIG. 2H-18 illustrates a stress-applying feature 386 is identical in all expect to the stress-applying feature 384 of FIG. 2H-17 except that two of the post quadrants have a shorter height than two of the other quadrants. In other embodiments, any two, three, or four quadrants may have the same or a different height, width, diameter, symmetry, asymmetry, or combinations thereof.

Stress-applying features having multiple plaque engaging elements on their upper surfaces are illustrated in FIGS. 2H-19 to 2H-21. FIG. 2H-19 illustrates a stress-applying feature 388 having four spherical plaque-engaging elements 388a on an upper surface of a cylindrical base 388b. FIG. 2H-20 illustrates a stress-applying feature 390 having four spherical plaque-engaging elements 390a supported by a cylindrical base 390b. The four spherical plaque-engaging elements 390a are mounted on a tapered conical support having a plaque-piercing tip 390c that its center. FIG. 2H-21 illustrates a stress-applying feature 392 which is identical to that of FIG. 2H-20, including four spherical plaque-engaging elements 392b surrounding a plaque-piercing tip 392c, but not including a cylindrical or other base. It will be appreciated that the different elements of the stress-applying features of FIGS. 2H-1 to 2H-21 can be combined and substituted in various ways to provide additional designs within the scope of the present invention.

FIG. 2H-22 illustrates a stress-applying feature 394 which comprises a simple arcuate bar 394a having a lower surface 394b which is attached directly or indirectly to an outer surface of a radially expanding structure.

As shown in FIG. 3 and subsequent drawings herein, the stress-applying features of the present invention may be attached to a variety of expandable structures including balloons, cages, sleeves, prosthetic valve bodies, valvulo-plasty members, drug delivery members, and the like, in addition to the stents and scaffolds which have been described above. For example, an expandable structure of the present invention may comprise a radially expandable sleeve 40, as shown in FIG. 3. The sleeve may be a tubular elastic membrane 42 configured to be placed over a balloon, a stent, a graft, or any other primary structure configured to be expanded within the lumen of a blood vessel or other body passage or lumen. The stress-applying features 24 may be attached to an outer surface 44 of the sleeve 40 in any one of a variety of configurations. As illustrated in FIG. 3, the stress-applying features 24 are arranged in a helical pattern with one end region 46 of the sleeve being free of stress-applying features.

Referring now to FIG. 4A, a sleeve scaffold 40a comprises a similar tubular elastic membrane 42 having individual stress-applying features 24 arranged in a diametrically opposed pattern on the outer surface of the tubular elastic membrane 42. Each successive pair of diametrically opposed stress-applying features 24 is staggered by 90°, as shown in FIG. 4B.

In other instances, as shown in FIGS. 5A and 5B, an elastic sleeve 40b comprises a tubular elastic membrane 42 having individual stress-applying features 24 arranged in groups of three ("triplets"), with each stress-applying feature in the triplet being spaced-apart from circumferentially adjacent features by 120°. Typically, successive "triplets" are staggered by 60°, as best seen in FIG. 5B.

While the patterns of stress-applying features shown in FIGS. 3, 4A, 4B, 5A, and 5B, are shown on elastic sleeves 40, it would be apparent to one of skill that these feature patterns can be employed on any expandable structure, including stents, grafts, scaffolds, expandable valvuloplasty cages, cages for performing, expandable angioplasty balloons and the like, in addition to the sleeves illustrated.

Figure 6A:
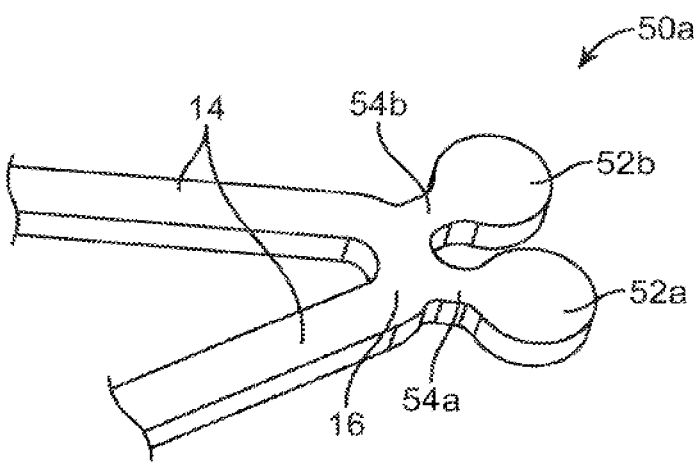
FIGS. 6A to 6C illustrate a first method for folding integral scaffold elements into stress-applying features on an outer surface of a scaffold.
Figure 6B:
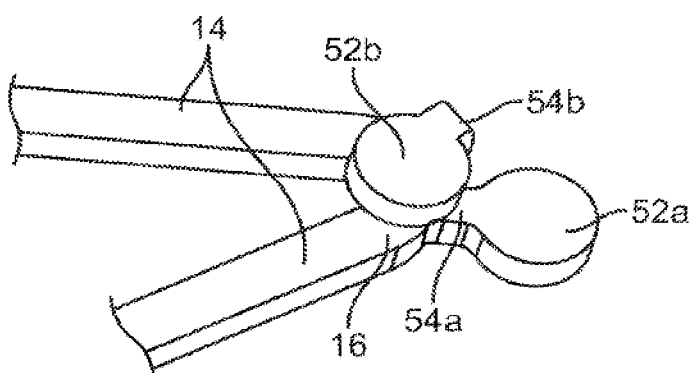
Figure 6C:
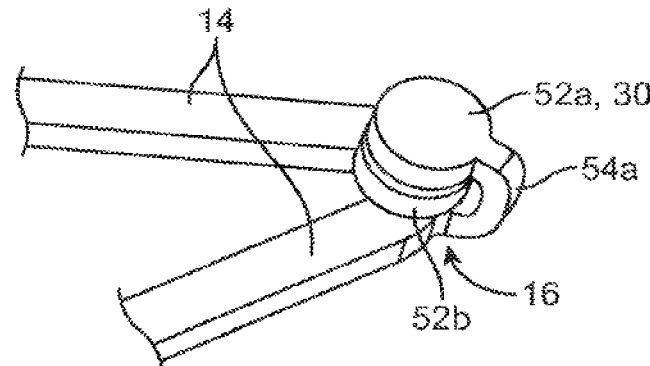

In some instances, the stress-applying features 24 may be formed as part of a scaffold fabrication process, as shown in FIGS. 6A through 8C. Referring to now FIGS. 6A through 6C, a scaffold may be patterned in any conventional serpentine or other pattern comprising struts 14 joined by U-shaped crowns 16 by laser cutting, photo-chemical etching, or the like. In accordance with the present invention, stress-applying features 50a may be provided by forming projecting elements 52a and 52b on the outer curve of the crown 16 during the initial fabrication of the tubular scaffold body, as shown in FIG. 6A. The projecting elements 52a and 52b are formed as disks joined to the crown by arms 54a and 54b. Disk 54b is first folded over an outer surface of the crown 16 by bending the arm 54b, as shown in FIG. 6B. Thereafter, disk 54a is folded over the exposed surface of disk 52b, as shown in FIG. 6C. In this way, the exposed surface of disk 52a provides the blunt contact region 30. While circular disks 52a and 52b are illustrated, a variety of other plate geometries could be utilized, such as square, rectangular, polygonal, oval, teardrop shaped, irregular, and the like.

As can be seen in FIGS. 6A to 6C, the projecting elements 50a will be formed within a cylindrical envelope of the scaffold as it is fabricated, requiring little departure from convention scaffold fabrication methods. In particular, a tubular blank can be used as the starting structure. The individual disks 52a and 52b then be sequentially folded over onto the outer surface of the crown 16 by bending arm 54 to provide the blunt contact region 30". In this way the two disks stack upon each other to create a stress-applying feature having a height twice the thickness of the struts 14 and crowns 16. What is initially the lower surface of the disk 52a then becomes the blunt contact region 30 of the resulting stress-applying feature, as shown in FIG. 6C.

Figure 7A:
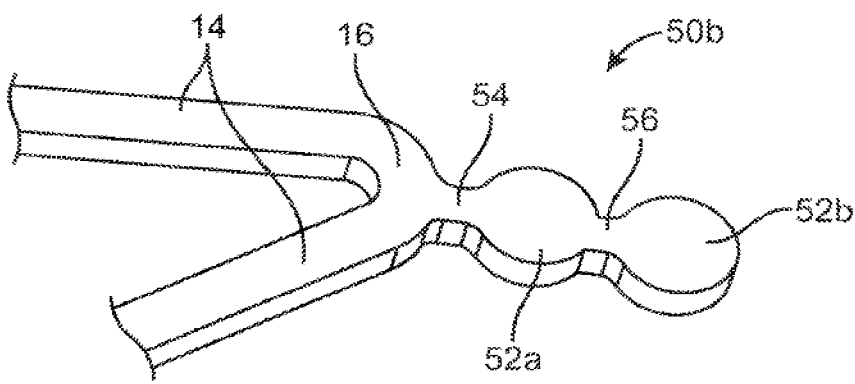
FIGS. 7A to 7C illustrate a second method for folding integral scaffold elements into stress-applying features on an outer surface of a scaffold.
Figure 7B:
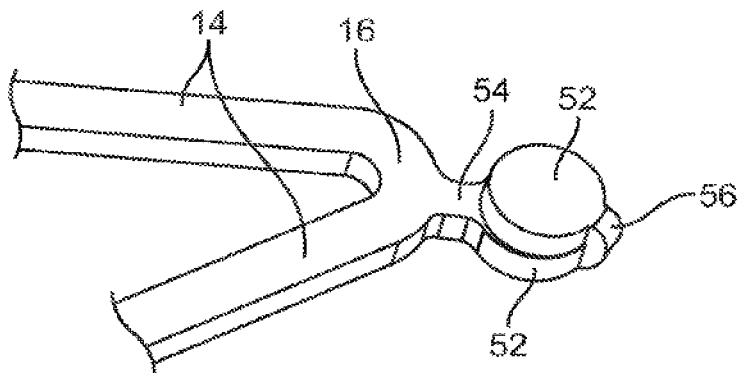
Figure 7C:
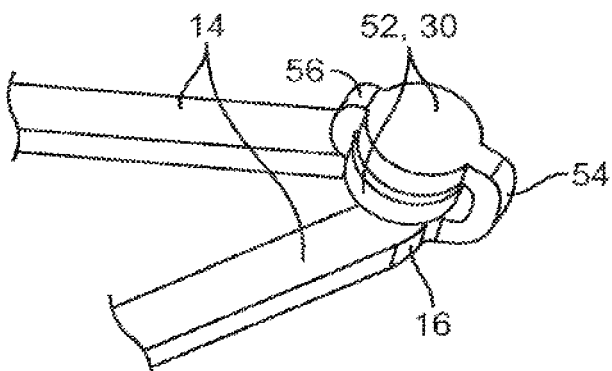

As shown in FIGS. 7A through C, a projecting element 50b includes two disks 52a and 52b join to a crown 16 in tandem by arms 54 and 56. The stress-applying feature is then formed over an outer surface of the crown 16 by first folding the outer disk 52b over the inner disk 52a by bending arm 56 as shown in FIG. 7B. The pair of stacked disks 52a and 52b are then folded over the outer surface of the crown 16 to provide the blunt contact region 30, as shown in FIG. 7C.

Figure 8A:
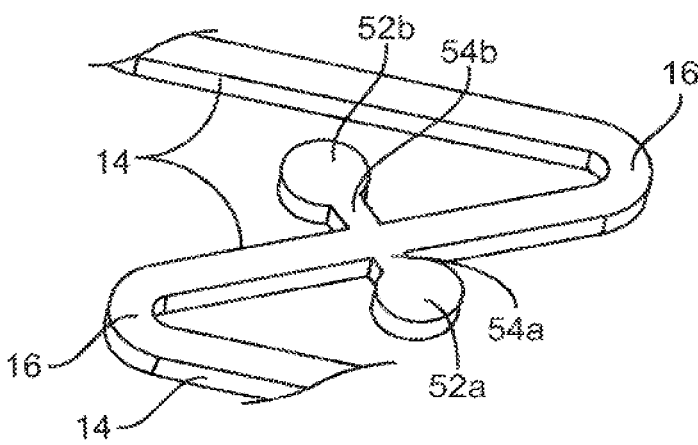
FIGS. 8A to 8C illustrate a third method for folding integral scaffold elements into stress-applying features on an outer surface of a scaffold.
Figure 8B:
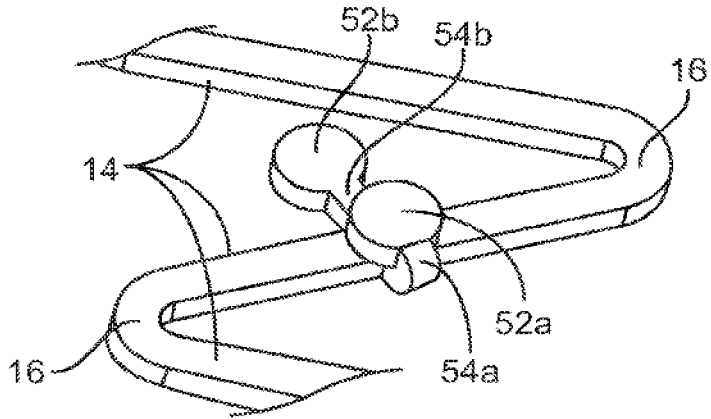
Figure 8C:
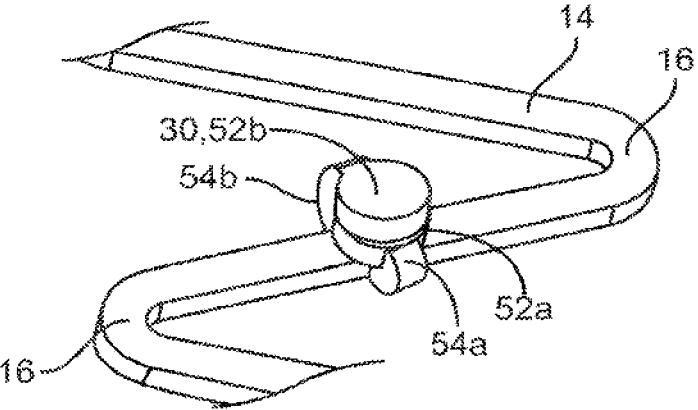

In a third example, as seen in FIGS. 8A to 8C, a pair of disks 52a and 52b are located on opposite sides of a strut 14 and attached by arms 54a and 54b. A first of the disks 52a is then folded over an outer surface of the strut 14, as shown in FIG. 8B, and the second disk 52b is then folded over the first disk 52a, as shown in FIG. 8C. The exposed surface of the second disk 52b thus provides the blunt contact region 30 of the present invention.

Figure 9A:
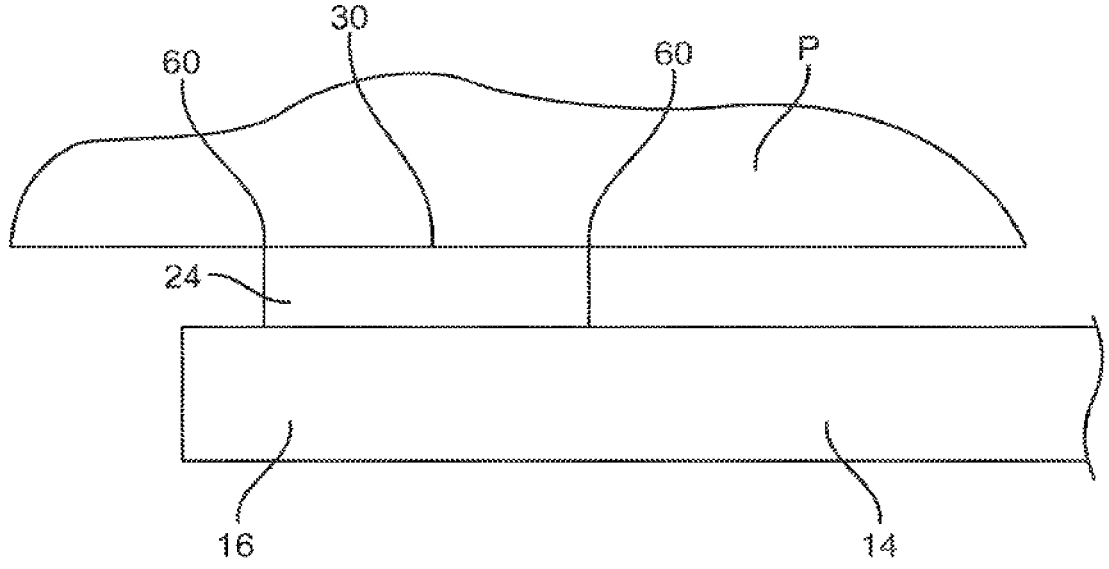
FIGS. 9A and 9B illustrate an example of how the stress-applying features of the present invention fracture calcified plaque when radially engaged against the plaque.
Figure 9B:
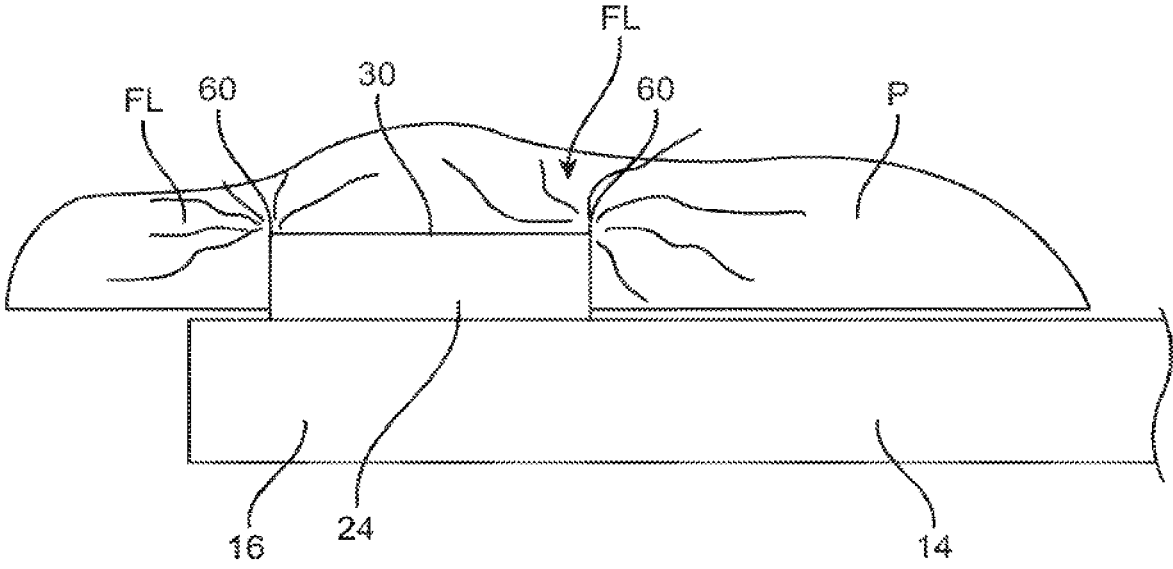

As shown in FIGS. 9A and 9B, a blunt contact region 30 of a stress-applying feature 24 is pressed radially outwardly against a region of plaque P or other occlusive material within a blood vessel lumen. As the expandable structure, such as a scaffold strut 14 shown in this figure, is radially expanded, a peripheral edge 60 of the blunt contact region 30 contacts an exposed surface of the plaque region P, as shown in FIG. 9A. As a crown 16 is deflected further by a balloon or other expansive force, the peripheral edge 60 is forced through the surface of the plaque region PR, causing the plaque region to fracture along fracture lines FL the while the blunt contact region 30 prevents injury to vascular wall. In other examples (not shown), the peripheral edge of the plaque disrupting feature may be beveled or rounded or may be coated with one or more material(s) to provide a beveled, a rounded, or smoother surface. In yet another example (not shown), the plaque-disrupting feature has rounded, convex, dull, or otherwise atraumatic contact region, body, or base, void of any edges that can hinder the advance of system into the body vasculature.

Figures 10A, 10B, 10C:
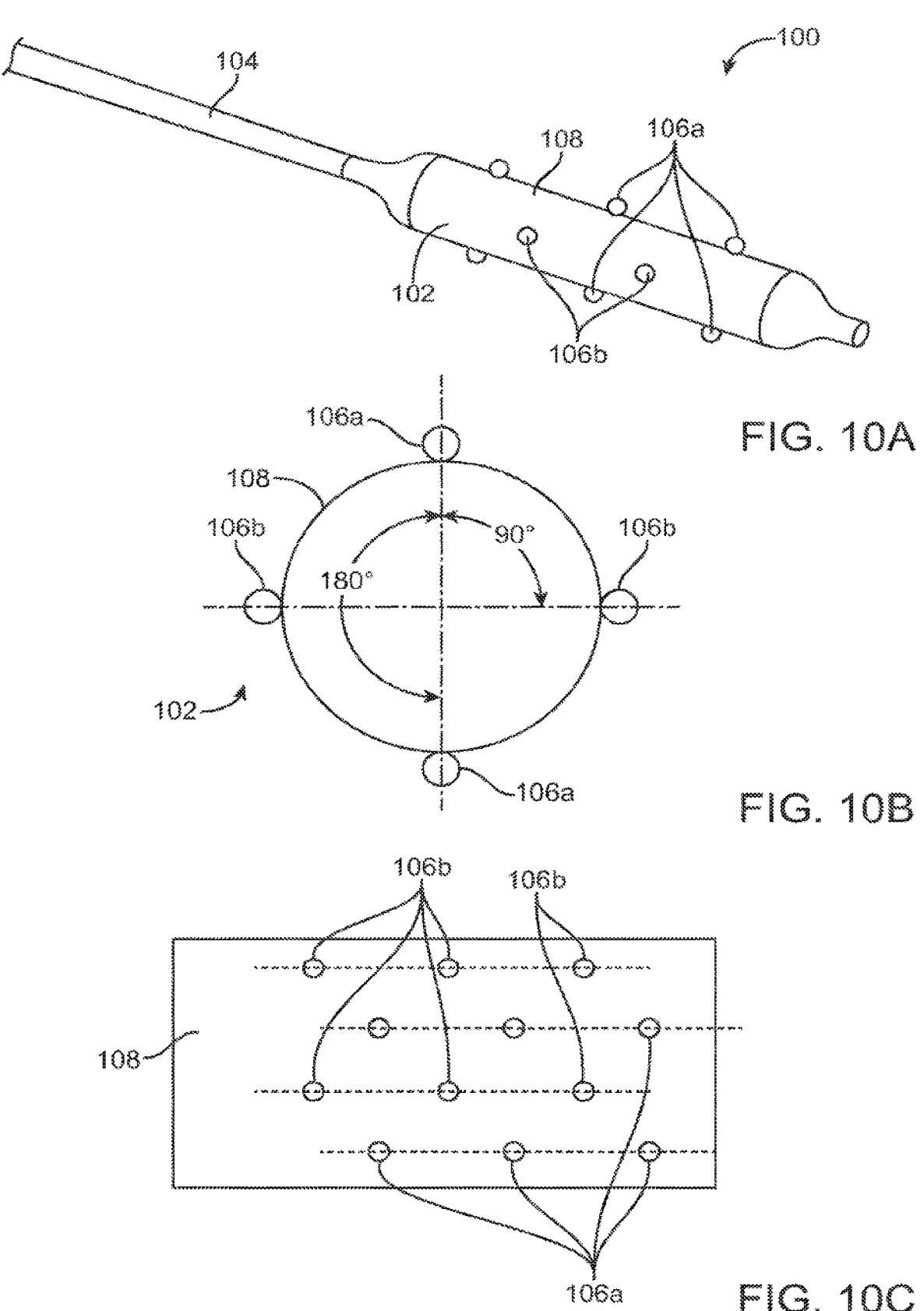
FIGS. 10A to 10C illustrate an alternative example of the present invention where a plurality plaque-disrupting features are present on an outer surface of an expandable structure, such as an inflatable angioplasty balloon or other medical balloon.

As shown in FIGS. 10A to 10C, a balloon catheter 100 has an inflatable balloon 102 at a distal end of shaft 104. A plurality of spherical plaque-disrupting features 106 are distributed over an outer surface 108 of the inflatable balloon 102. The spherical plaque disruption features 106 are arranged with pairs of disruption features 106a and 106b located on opposite sides of the balloon surface 108. Additionally, each pair of features 106a and 106b is rotationally or circumferentially displaced from the adjacent pair by 90°, as best seen in FIGS. 10B and 10C.

Figures 11A, 11B, 11C:
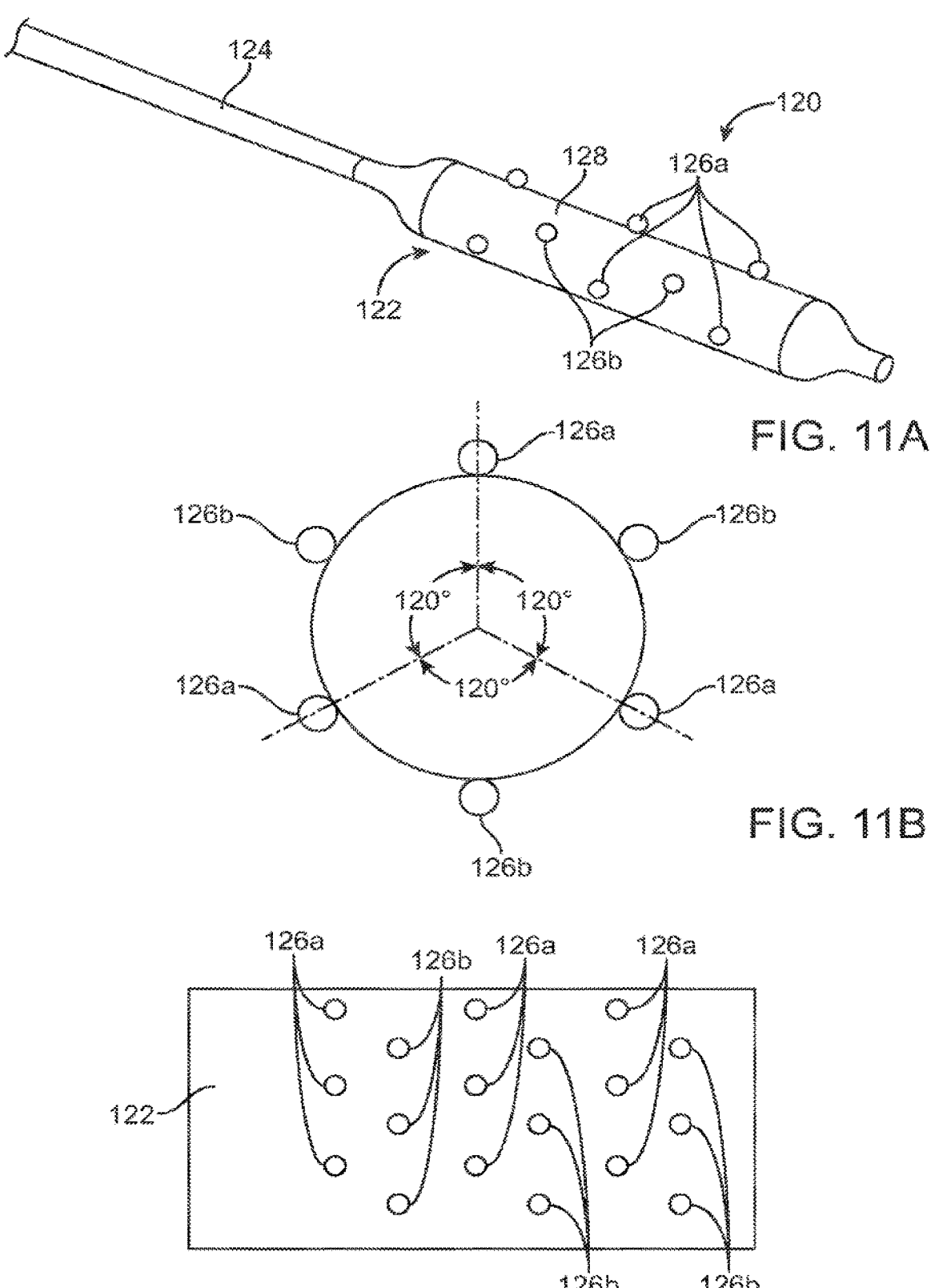
FIGS. 11A to 11C illustrate an example of the present invention having a plurality of plaque-disrupting features similar to those illustrated in FIGS. 10A to 10C but arranged in yet another pattern.

As shown in FIGS. 11A to 11C, a balloon catheter 120 has an inflatable balloon 122 at a distal end of shaft 124. A plurality of spherical plaque-disrupting features 126a and 126b are distributed over an outer surface 128 of the inflatable balloon 122. The spherical plaque-disruption features 126a-b are arranged with triplets of disruption features 126a and 126b located with a spacing of 120° the balloon surface 128. Additionally, each triplet of features 126a and 126b is rotationally or circumferentially displaced from the adjacent pair by 60°, as best seen in FIGS. 11B and 11C.

Figures 12A, 12B, 12C:
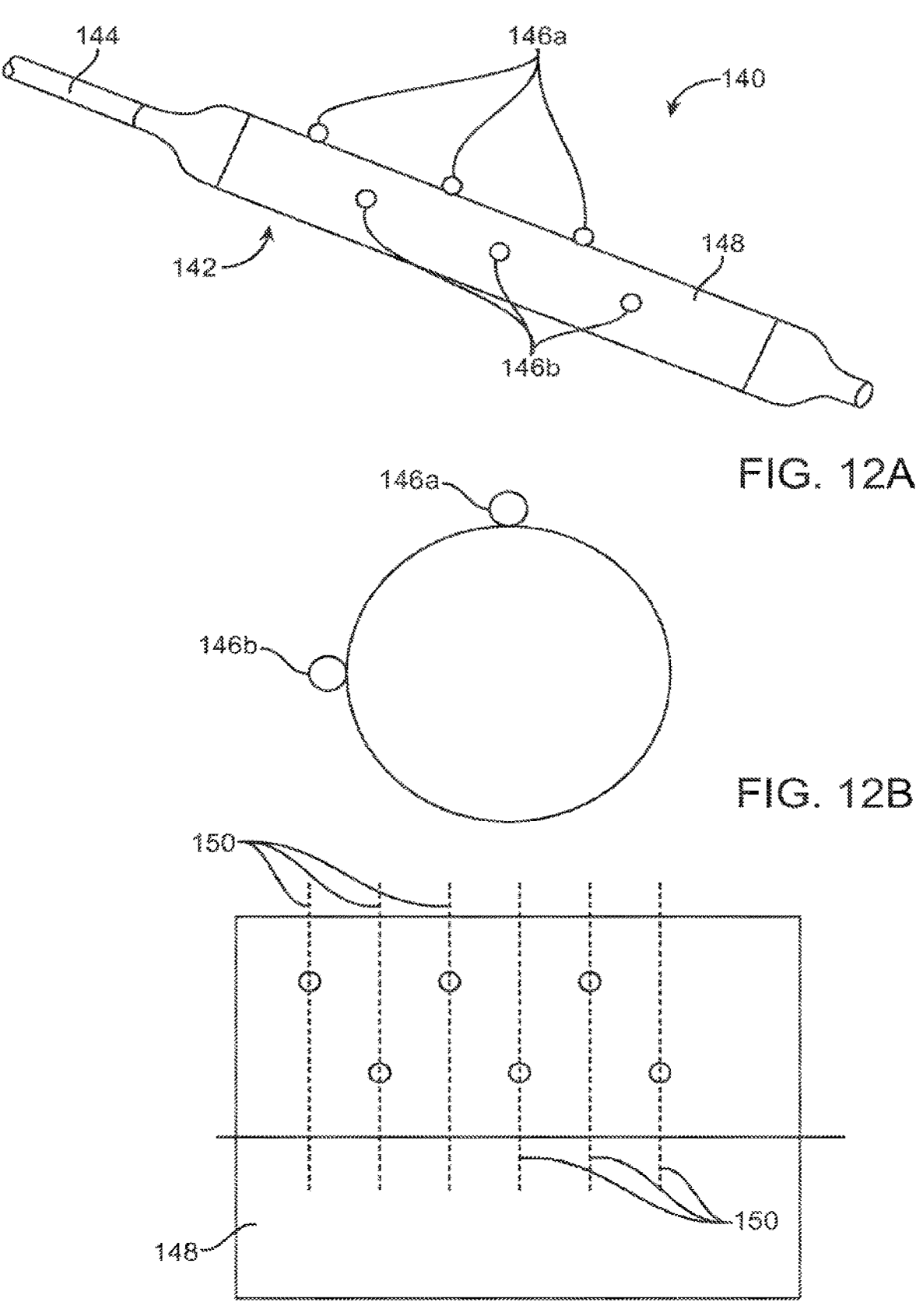
FIGS. 12A to 12C illustrate an example of the present invention having a plurality plaque-disrupting features similar to those illustrated in FIGS. 10A to 10C but arranged in different patterns in accordance with the principles of the present invention.

As shown in FIGS. 12A to 12C, a balloon catheter 140 has an inflatable balloon 142 at a distal end of shaft 144. A plurality of spherical plaque-disrupting features 146a and 146b are distributed over an outer surface 148 of the inflatable balloon 142. In contrast to prior environments, however, the plaque-disrupting features 146a/b are not arranged symmetrically. Instead, they are arranged in two axial lines comprising features 146a and 146b, respectively, spaced apart by 90° along the edges of one quadrant of the balloon. The spherical plaque-disrupting features 146 are also axially staggered so that they lie on different, axially spaced apart circumferential lines 150 around the balloon surface 148.

Figure 12D:
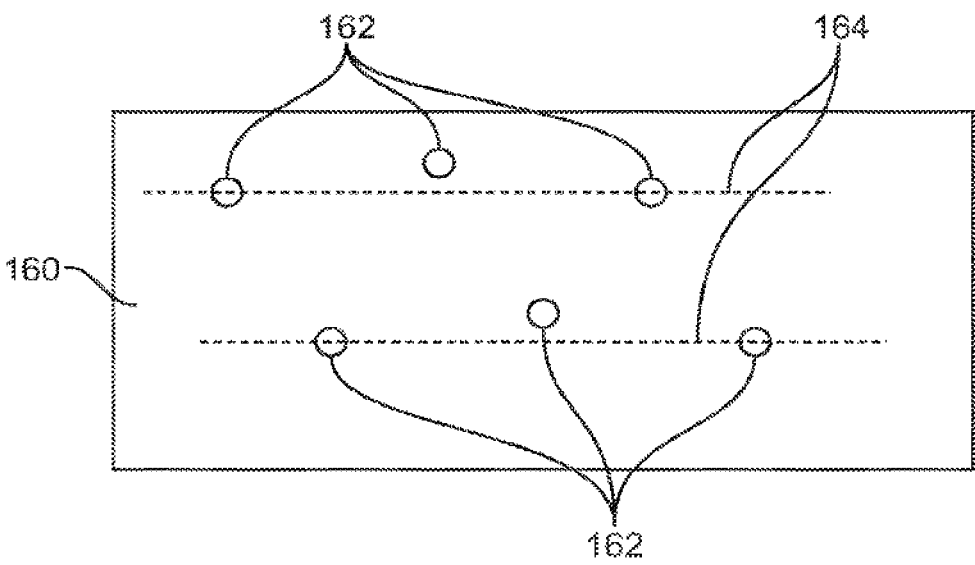
FIGS. 12D to 12H illustrate yet further variations of the plaque-disrupting feature patterns of the present invention.
Figure 12E:
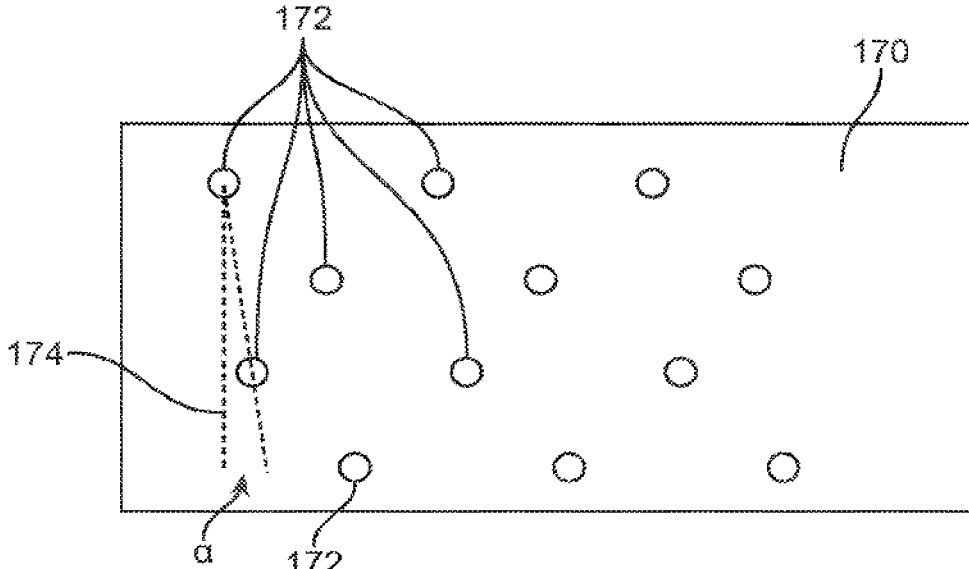
Figure 12F:
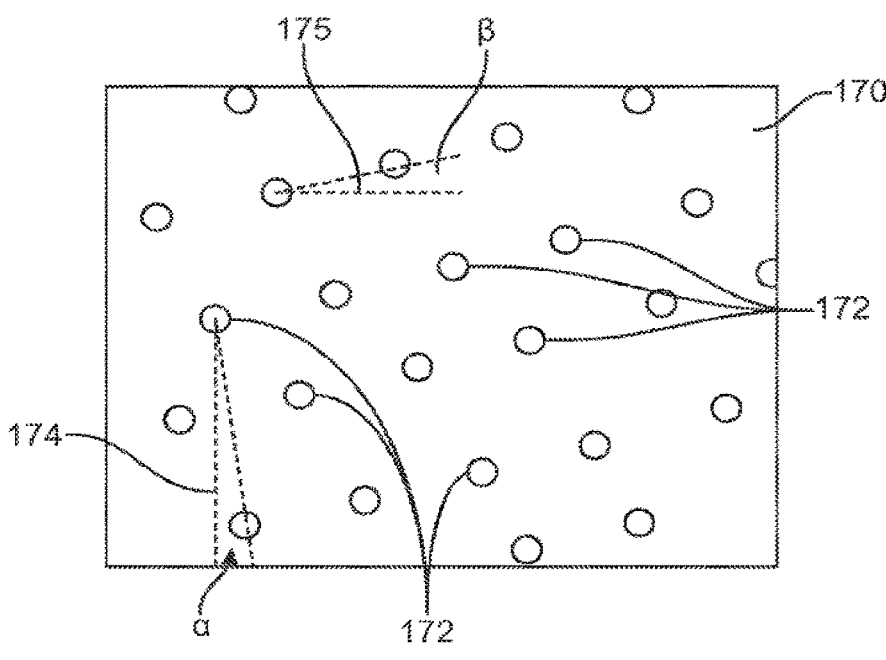

Although specific symmetric and asymmetric disruption feature patterns have been illustrated, it will be appreciated that a wide variety of patterns are possible and that some patterns may be configured fall out of alignment. For example, in FIG. 12D, the disruption features 162 generally positioned along axial lines 164 on a balloon surface 160 (shown rolled out) but may be configured to fall circumferentially away from those lines. As shown in FIG. 12E, disruption features 172 which generally lie on circumferential lines 174 on a balloon surface 170 may circumferentially deviate from those lines by a small angle α. Similarly, as shown in FIG. 12F, those disruption features 172 which are generally positioned along axial lines 175 may axially deviate from those lines by a small angle β. Such small misalignments help space the features apart and minimize or avoid interference between features when the expandable structure is radially crimped or collapsed prior to expansion. For example, if a plurality of features were all attached along a single circumferential line, the features could circumferentially collapse against each other when the expandable member is radially crimped or collapsed prior to expansion. Such interference can be reduced or eliminated by moving some or all of the features off of the circumferential line, even by just a small distance such as a width of the feature.

Figure 12G:
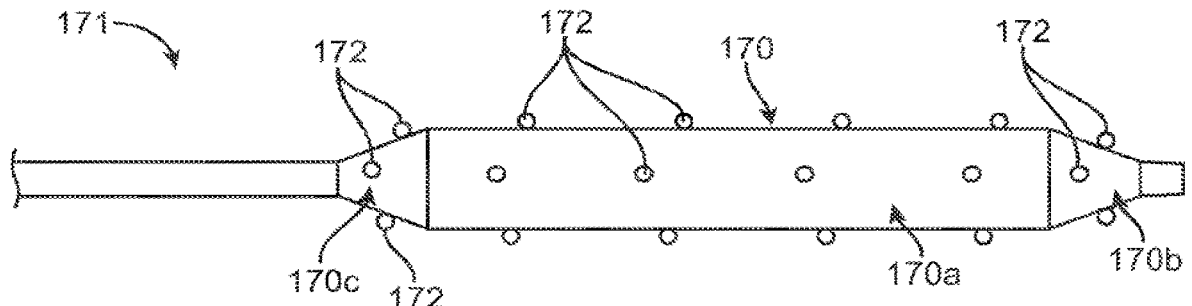
Figure 12H:
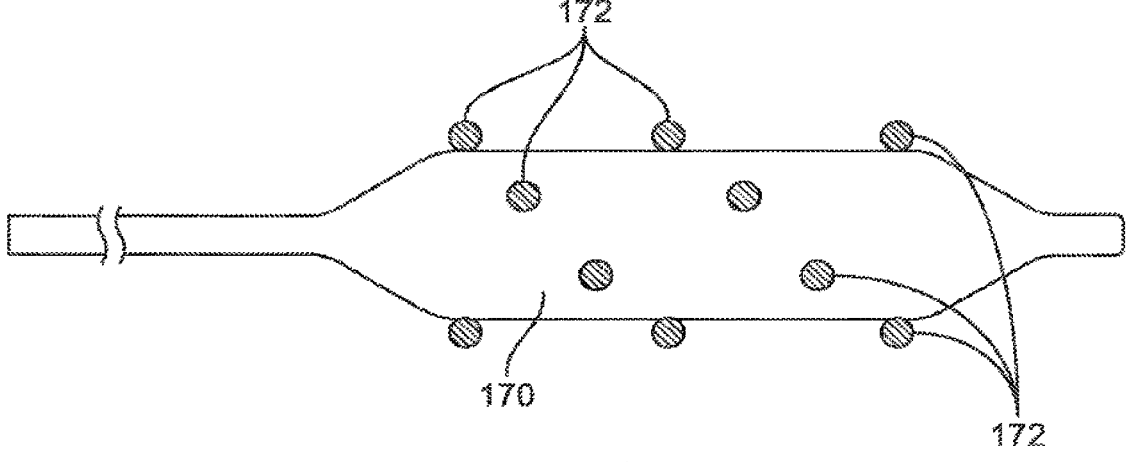

Referring now to FIGS. 12G and 12H, disruption features 172 may be distributed over a balloon surface 170 of a fully formed balloon catheter 171 in a variety of patterns. The disruption features 172 will usually be distributed over all or a portion of at least a central region 170a of the balloon surface. Optionally, the disruption features 172 may also be distributed over a tapered distal region 170 b (FIG. 12G) of the balloon surface 170 as well as over a tapered proximal region 170c thereof. Specific distribution patterns may be any of those described elsewhere in this application including at least those shown FIGS. 12G and 12H.

Figures 12I, 12J, 12K, 12L:
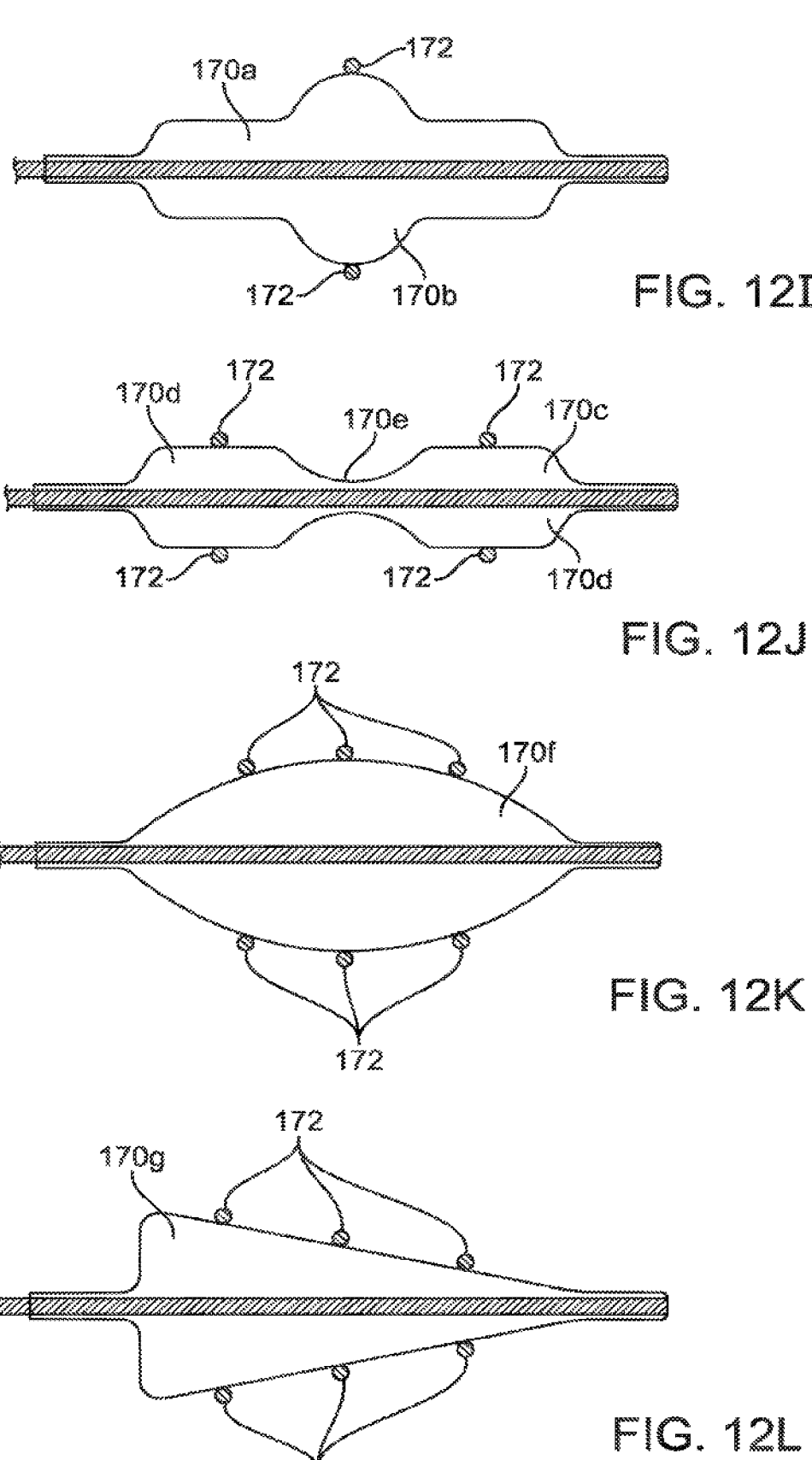
FIGS. 12I to 12L illustrate different balloon shapes and stress-inducing feature distribution patterns in accordance with the principles of the present invention

As shown in FIGS. 12I to 12L, the plaque-disrupting features 172 of the present invention may be placed on balloons and other expandable structures having a variety of different geometries and configurations. For example, as shown in FIG. 12I, the plaque disrupting features 172 may be placed on an oversized middle section 170b of an inflatable support balloon 170a, or on adjacent cylindrical or tapered end sections (not shown). As shown in FIG. 12J, the plaque disrupting features 172 may be placed on adjacent segments 170d of a balloon 170c having a depression, waist 170e at its middle. In some cases, the depression 170e could have a plurality of plaque disruption features while adjacent segments 170d could be free of plaque disruption features. As shown in FIG. 12K, the plaque-disrupting features 172 may be placed on balloons or other expandable supports 170f having ovoid or spheroidal shapes. As shown in FIG. 12L, the plaque-disrupting features 172 may be placed on balloon supports 170g having a tapered conical shape on one side and a flat surface at a proximal end thereof. In some instances, the tapered conical surface of the balloon or other support can have plaque disruption features on the flat end (not shown), while the conical tapered segment is void of plaque disruption features (not shown).

In such exemplary arrangements, the preferred hemispherical or spherical plaque disrupting features are "discrete," i.e., separated from each other in the circumferential and axial directions and protruding radially outwardly from the outer surface of the balloon or other expandable structure before and after expansion of the expandable structure. The hemispherical or spherical plaque disrupting features may be placed on the working length of the balloon only (as shown in FIGS. 10A, 11A, 12A, and 12H), on both the working length and the proximal and/or distal regions (FIG. 12G), or in some cases only the proximal and/or distal regions (not shown).

Figure 13A:
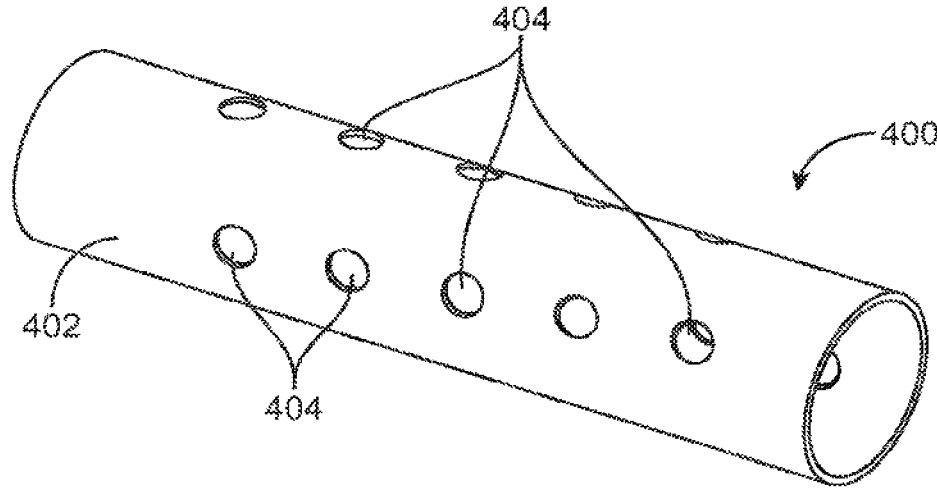
FIGS. 13A and 13B illustrate tubular templates that may be used in positioning a plurality plaque-disrupting features on an outer surface of a balloon or other expandable structure.
Figure 13B:
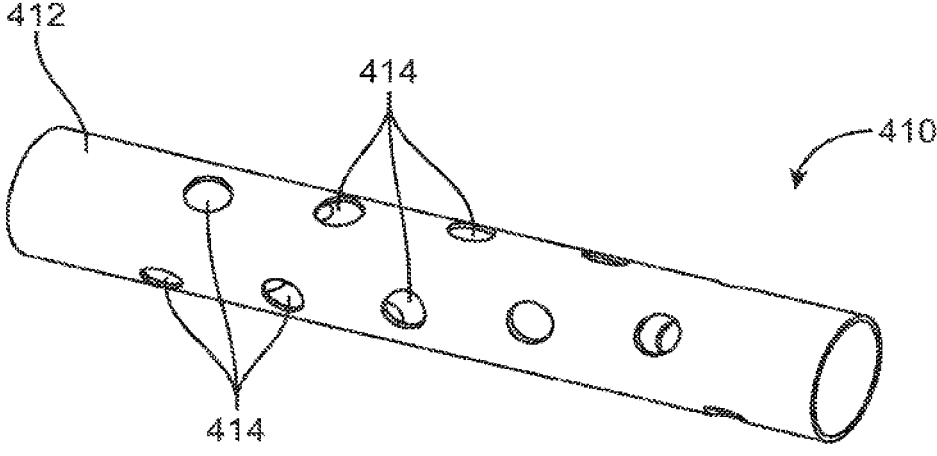
Figure 15:
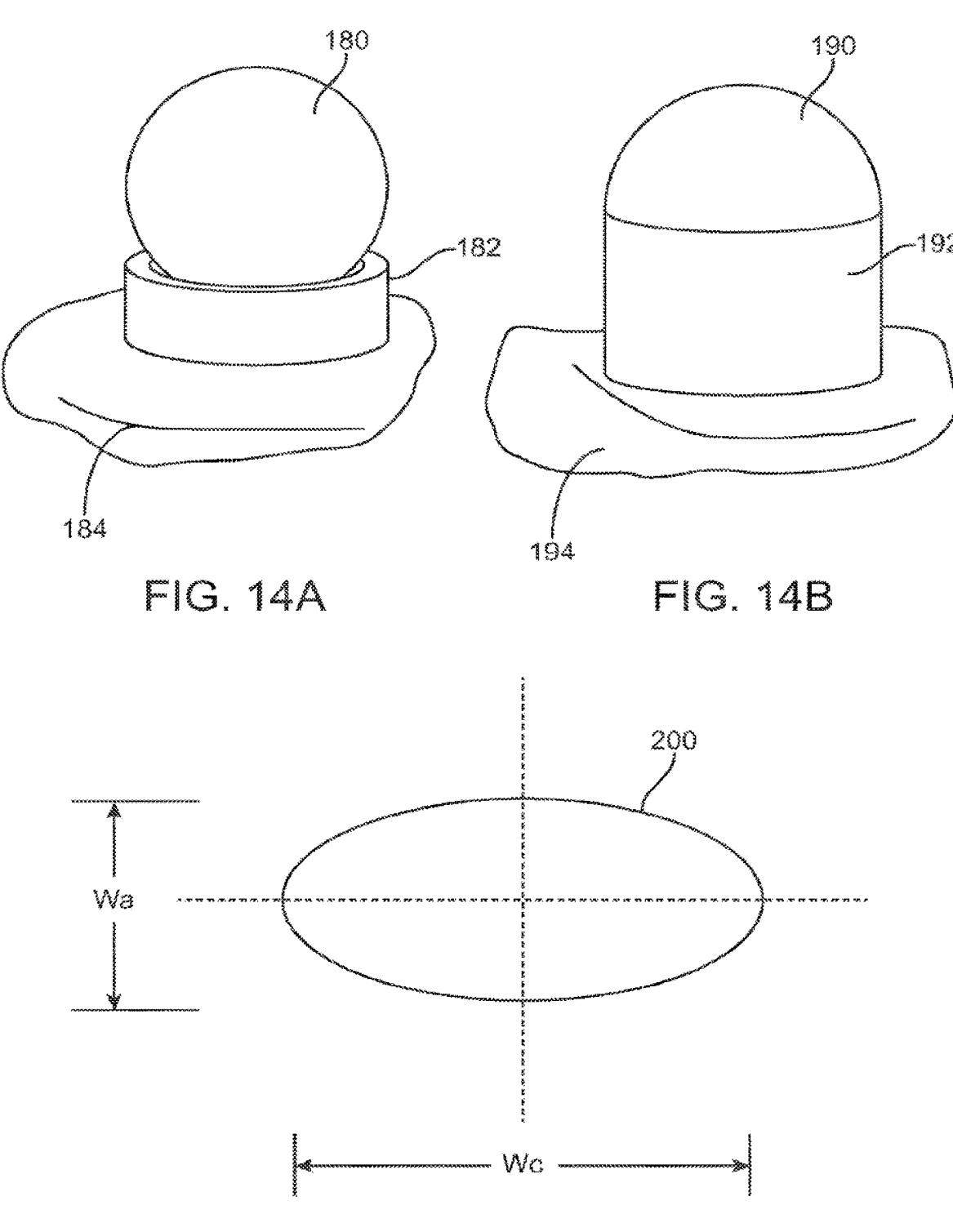
Figures 16A, 16B, 16C, 16D, 16E, 16F, 16G, 16H:
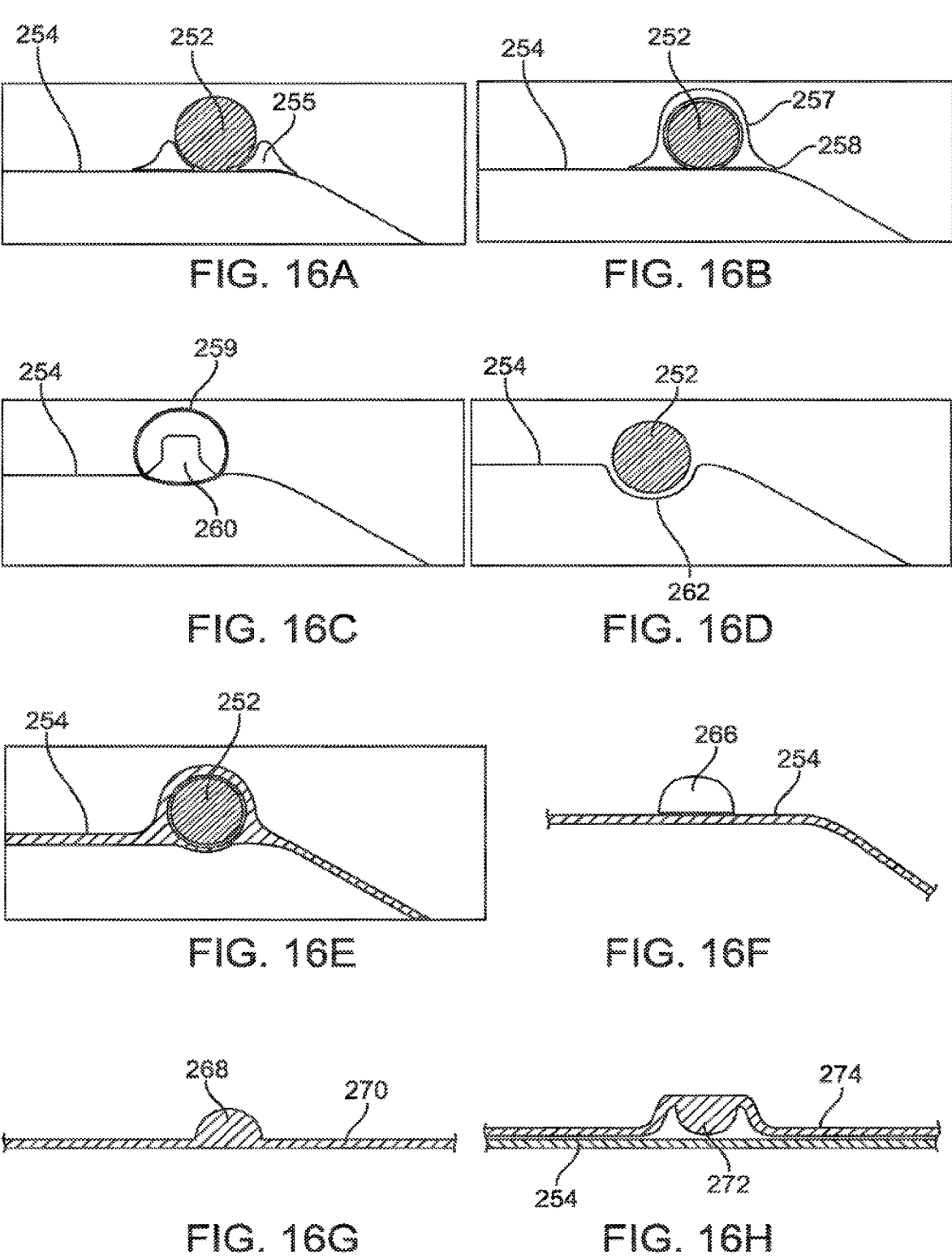
FIGS. 16A to 16H illustrate exemplary attachment methods for spherical, hemispherical and other plaque-disrupting features in accordance with the principles of the present invention.
Figures 1, 16D:
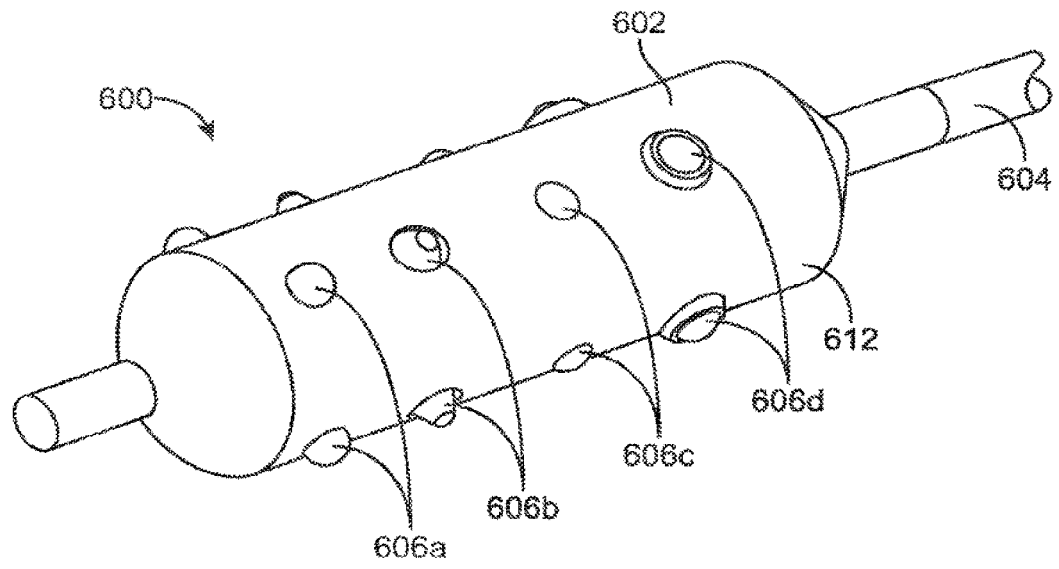
Figures 2, 16D:
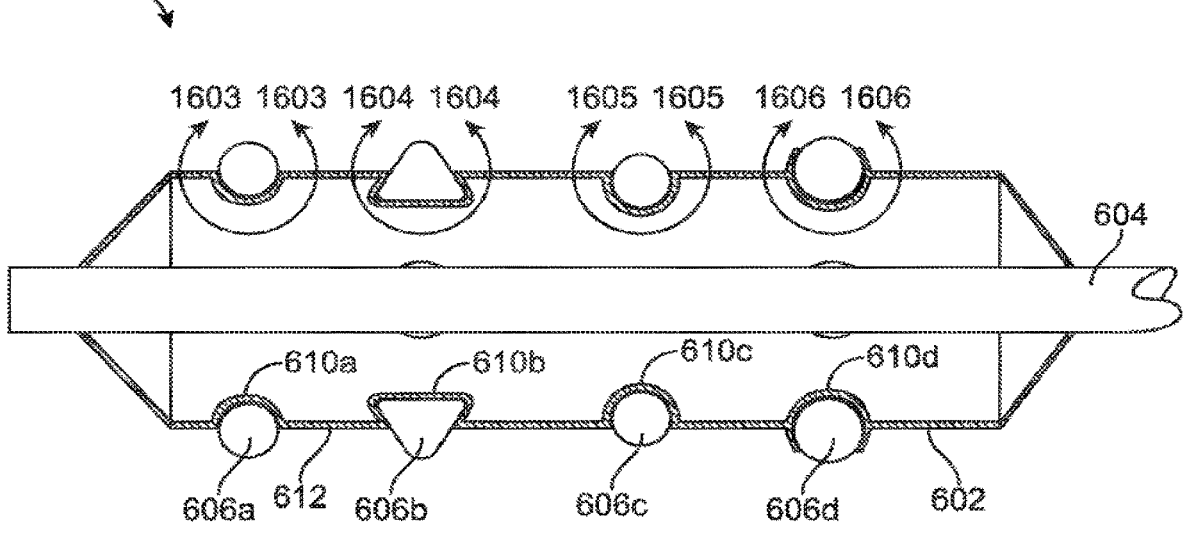
Figures 3, 4, 5, 6, 16D:
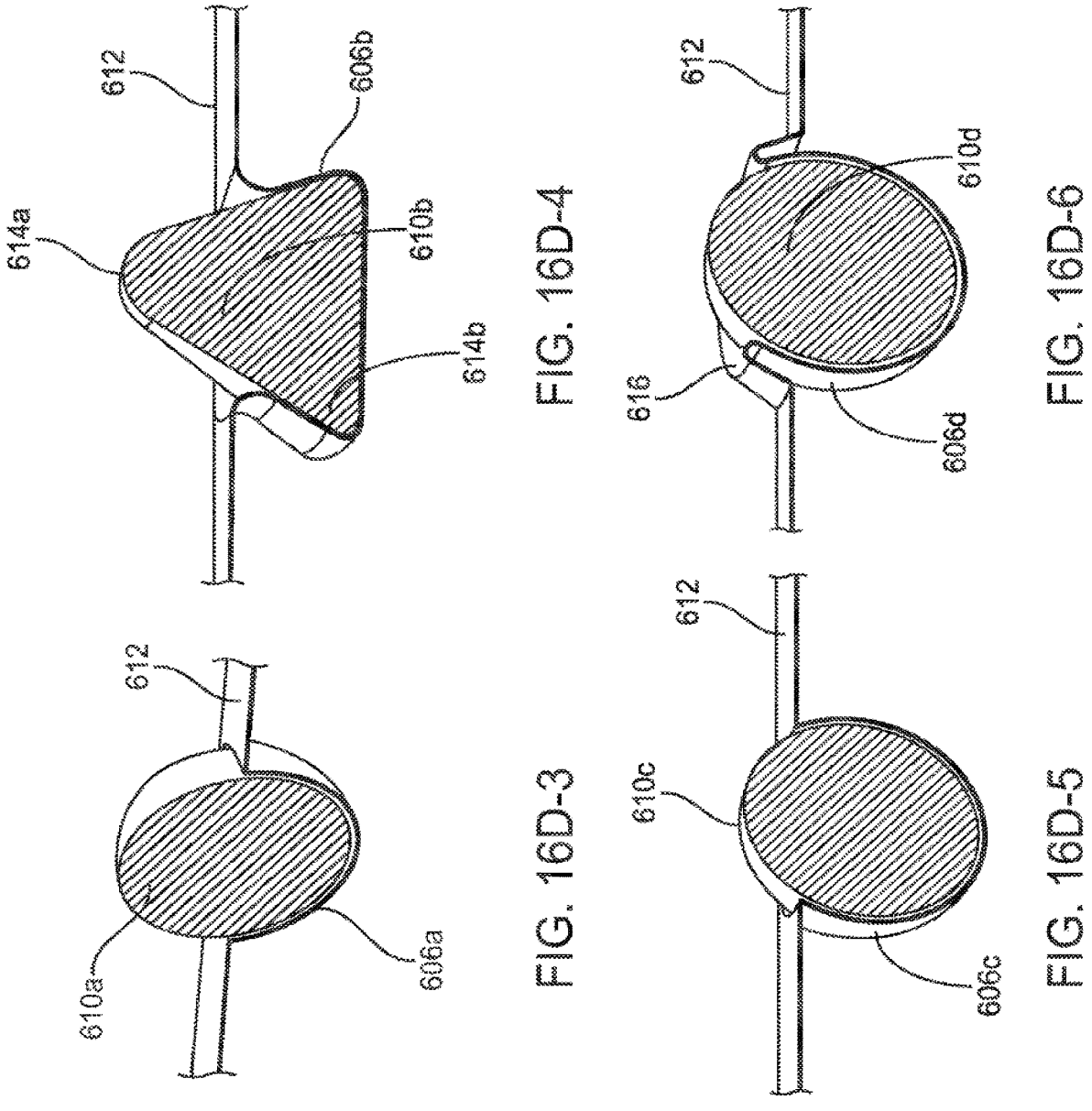

As shown in FIGS. 13A and 13B, plaque disrupting features may be positioned on an outer surface of the balloon, sleeve or other expandable member using a tubular template. Tubular tube 400 shown in FIG. 13A comprises a PTFE sheath 402 with a pre-selected pattern of circular or other cutouts 404 configured to be placed over an outer surface of an expanded balloon or sleeve where the cutouts allow the placement of adhesive material such as adhesive droplets onto the surface of the expandable structure such as an outer surface of a balloon, sleeve or other expandable structure for attachment of the plaque disrupting features, e.g., as shown in FIG. 16A described below. Smaller tubular templates 410 comprising a PTFE or other sheath 412 with circular or other cutouts 414 may be provided for placement over uninflated or unexpanded balloons and sleeves or smaller expanded balloons and sleeves. After placement of the adhesive droplets, the tubular template is removed and the features are placed and press fit on the droplets along the length and circumference of the outer surface expandable member, typically while partially or fully inflated.

Referring now to FIG. 14A, a spherical plaque-disrupting feature 180 may be secured to a balloon surface 184 using a circular base 182. The circular base 182 helps stabilize the disruption feature 180 on the balloon surface and may be secured by adhesive attachment, laser welding, heat welding, or other means known in the art. In addition, the entire structure of the disruption feature 180 and the circular base 182 may be further held in place by placing of a cover (not shown) over the structure as described previously herein.

Referring now to FIG. 14B, a hemispherical plaque-disrupting feature 190 may be secured to an outer surface of an expandable structure, such as a balloon, cage, or sleeve using a cylindrical base or pillar 192. The base 192 stabilizes the disruption feature 190 on the balloon surface and also elevates the surface of the disruption feature 190 by pre-determined height or elevation above the balloon surface 194. In this way, the radially outward extent of the disruption feature can be elevated at any desired distance above the balloon surface, typically in the range is set forth above. It's described previously, the base or pillar 192 and the hemispherical feature 190 may be secured to the balloon service 194 using adhesive attachment, laser welding, heat welding, or other means known in the art. In addition, the entire structure of the disruption feature 190 and the base or pillar 192 may be further held in place by placing of a cover (not shown) over the structure as described previously herein.

Figures 2, 2H, 3, 4, 5, 6:
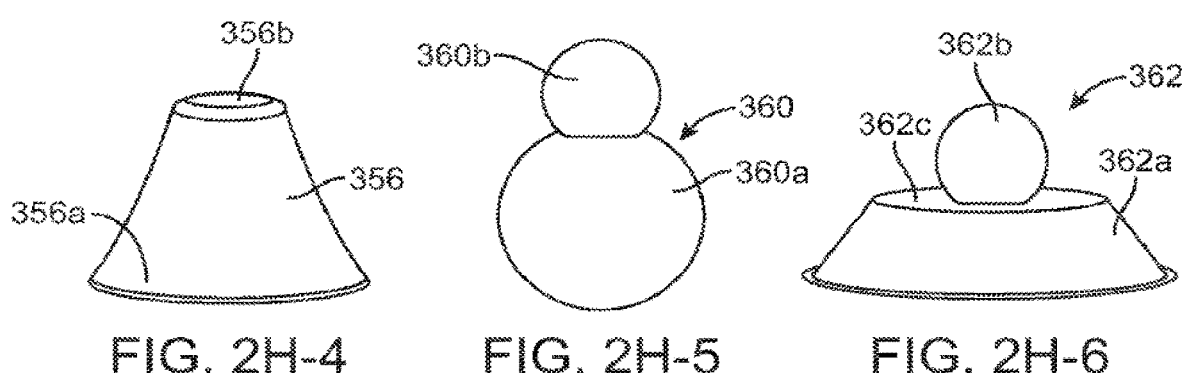
Figures 2, 2H, 3, 4, 5, 6, 7, 8, 9:
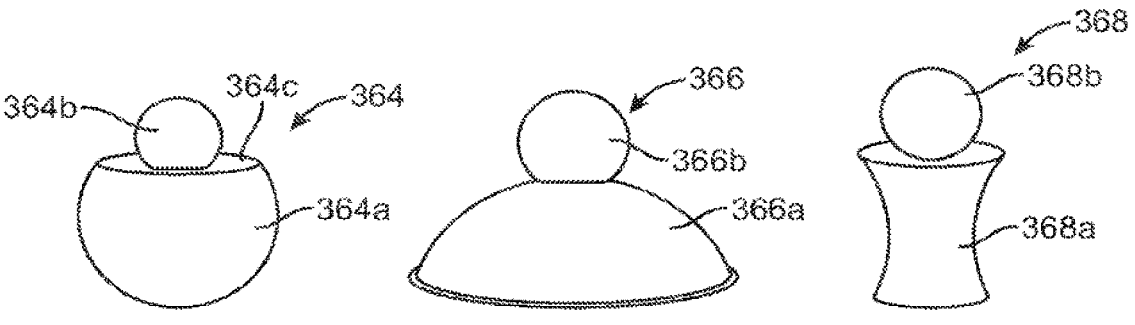
Figures 2, 2H, 3, 4, 5, 6, 7, 8, 9, 10, 11, 12, 13, 14, 15, 16, 17, 18:
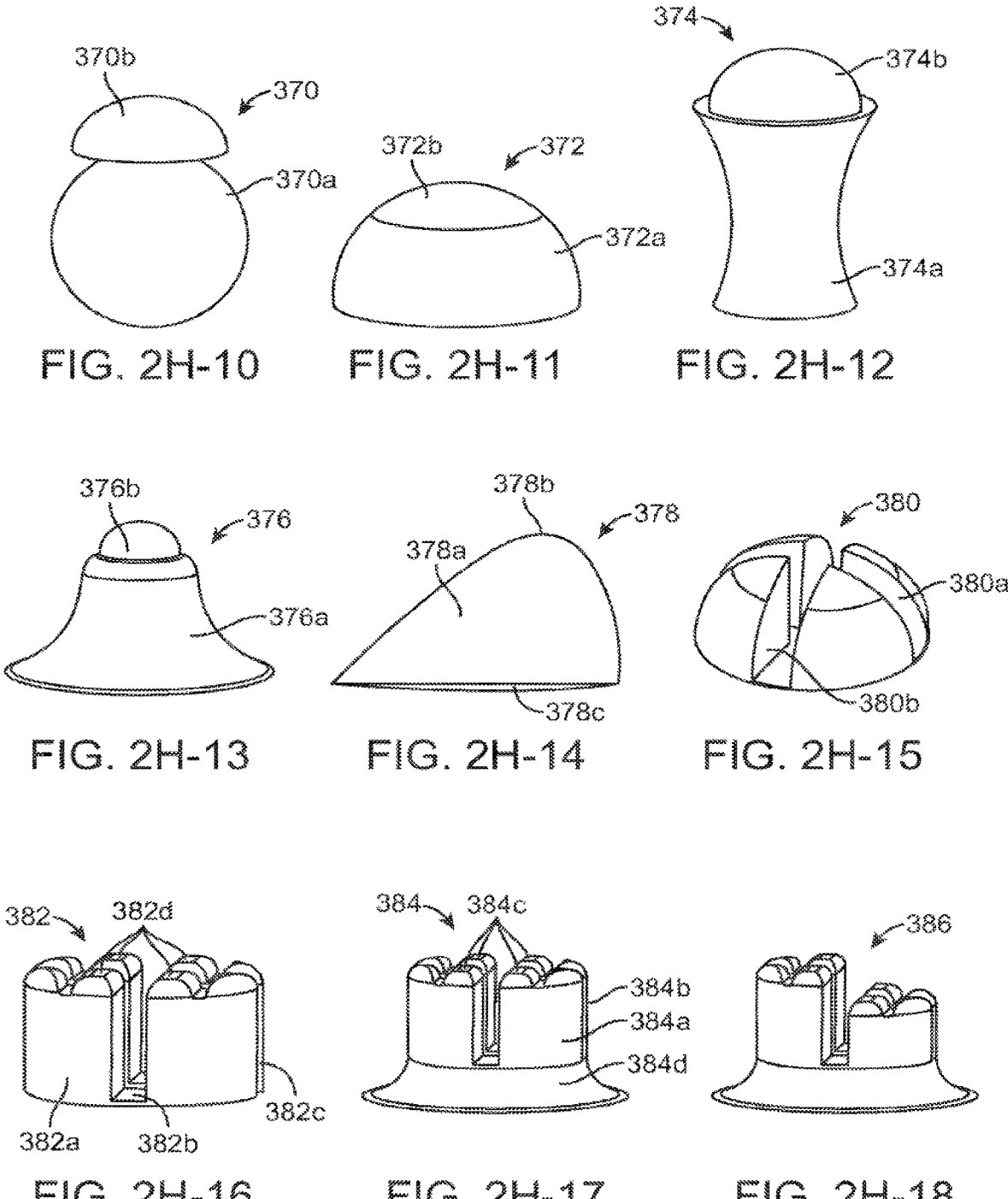

Referring now to FIG. 15, the plaque-disrupting features of the present invention will preferably be discrete, as described above, and secured directly to the surface of the expandable structure, preferably to the outer surface of the expandable structure such as balloon, sleeve, cage, or other expandable member. In particular, the disruption features and optional bases will not extend any significant axial distance along the surface of the balloon, sleeve, cage, or other expandable member. In contrast, the cutting elements on typical cutting balloons are elongate blades which extend axially over a major portion of the balloon length in order improve cutting performance. The disruption features of the present invention preferably do not extend significantly in either the axial or circumferential directions on the surface of the expandable member and are physically independent of each other (i.e., not coupled or linked to each to each other except by the expandable member itself) with relatively small footprints on the balloon surface. In particular, as shown in FIG. 15, the ratio of axial width $W_a$ to circumferentially width $W_c$ of the peripheral footprint 200 will be in a range from 0.5 to 5, usually from 1 to 5, more usually from 2 to 5, and typically being 1 to 1 which is characteristic of a circular base or footprint. In rare instances, the Wa:Wc ratio is 3:1 to 1.5:1.

As shown in FIGS. 16A to 16H, plaque-disrupting features may be attached to an outer or inner surface of an expandable structure or other underlying substrate in a variety of ways. For example, a solid or hollow metal or other spherical plaque-disrupting features 252 may be glued, welded, or otherwise adhered to a surface of a substrate 254, where the substrate can be any of a structure the scaffold, an elastic, semi-elastic, or non-distensible membrane of a balloon catheter, an elastic sleeve, cage, valvuloplasty balloon, or the like.

As shown in FIG. 16A, the spherical stress-applying or plaque-disrupting features 252 may be fixed in place by use of an adhesive and/or polymer coating and/or by partially or fully encapsulating the feature. The adhesive/coating material may comprise a single material or a combination of two or more materials. For example, an adhesive, polymer or cement may be formed providing a base or a "cradle" 255 surrounding and adhering to a lower portion of the spherical stress-applying feature 252. The adhesive contours to and partially or fully surrounds the lower portion of the stress-applying feature 252 (as shown) and can extend beyond the footprint of the feature (as shown). The adhesive typically surrounds the feature boundary. In some instances (not shown), the adhesive material can contour to, surrounding, and/or partially cover or encapsulate the outer surface of an upper portion of the feature.

As shown in FIG. 16B, the plaque-disrupting feature 252 may be fixed in place by an adhesive or a polymer coating 257 which covers and encapsulates the entire surface of plaque-disrupting feature 252 exposed over the surface. The adhesive or coating 257 adheres to the substrate 254 about a bottom periphery 258 of the feature.

As shown in FIG. 16C a hollow feature, such as a hollow sphere 259 having a truncated or open bottom, may be mounted on a post 260 which protrudes outwardly from a surface of a substrate, typically the outer surface of the substrate 254. The post may be pre-formed, e.g., molded as part of the balloon or other substrate 254 or may be separately formed and attached to the balloon using an adhesive, cement, ultrasonic bonding, or other conventional procedure. The post will typically be formed to conform to a cavity in the hollow sphere 259 and will also be attached using an adhesive, cement, ultrasonic bonding, or other conventional procedure (as shown). Optionally, the hollow truncated sphere may be attached to the balloon surface where the adhesive and/or polymeric material covers the inside of the sphere partially or fully (not shown).

As shown in FIG. 16D, the spherical plaque-disrupting feature 252 may be attached to the outer surface 254 of the substrate in a preformed indentation 262 which provides a receptacle or "cradle" for immobilizing the feature using one or more adhesive or polymeric materials. The cradle may be formed to conform closely to the feature to improve attachment. The feature may have a slightly wider base than the cradle to provide further support or securement.

FIGS. 16D-1 to 16D-6 illustrate further examples of features attached in preformed indentations in an outer surface of a balloon which provides a receptacle or "cradle" for immobilizing a plurality stress-inducing feature using one or more adhesive or polymeric materials. Although a balloon is illustrated, it will be appreciated that the use of indentations for immobilizing stress-inducing features will be applicable to other expandable members which comprise a polymeric membrane or sheet forming an expandable surface, specifically including but not limited to elastomeric and non-elastomeric sleeves.

A catheter 600 having an angioplasty or other inflatable, interventional balloon 602 at a distal end of a shaft 604 is illustrated in FIGS. 16D-1 and 16D-2. A plurality of stress-inducing features 606a to 606d are held in indentations 610a to 610d formed in an outer surface 612 of the balloon. The indentations in the surface 612 may be pre-formed or molded over a bottom surface of the stress-inducing features, and in both cases will preferably conform closely to the geometry of the lower portion of the feature 606a-606d. The stress-applying features 606a, 606c and 606d are shown as spheres. In contrast, the stress-applying feature 606b has a conical shape with a rounded apex 614a (FIG. 16D-4) protruding from the indentation 606b and over the surface 612. The conical stress-applying feature 610b has an enlarged base 614b which retained in the conforming indentation 606b. All stress-applying features 606a to 606d are shown as solid structures, typically metal or other hard materials as described previously, but could also be formed as hollow structures, as for example shown in FIG. 16C.

In exemplary cases, an adhesive would cover at least a portion of a surface or "interface" of the indentation 610a to 610d between the feature 606a to 606d and balloon 602 or other expandable structure. In other examples, an adhesive could protrude above the expandable structure surface further cradling or encapsulating of at least part of the outer surface of the feature, sometimes encapsulating the entire outer surface of the feature. In some instances, such as shown in FIGS. 16D-4 to 16D-6, a lower portion of the indentation 610*b* to 610*d* is larger than a neck of the indentation to provide more protection in holding the feature in place. As shown in FIG. 16D-6, the expandable surface has a lip 616 that protrudes above the surface 612 of the balloon 602 surrounding the neck to enhance retention when the balloon is inflated by pressing the lip against the surface of the feature adjacent to the neck.

As shown in FIG. 16E, the feature 252 may be encapsulated or integrated in the outer surface of the balloon or other substrate 254 by fusing or laminating the feature in one, two or more layers of one or more balloon materials, optionally being fused to form one inseparable layer.

As shown in FIG. 16F, A solid metal or other hemispherical plaque-disrupting features 266 may be attached to the surface of the membrane 254 in any of the ways just described, typically being fixed in place by use of an adhesive, a polymer coating, and/or by partially encapsulating the feature.

Alternatively, hemispherical and other plaque disruption features 268 may be molded over otherwise integrally formed with a polymeric membrane to 270, as shown in FIG. 16G.

As a further alternative, plaque-disrupting features 272 may be molded or otherwise integrally formed as a part of an elastic, constraining sleeve or sheath 274, typically on an inner surface of the sleeve, as shown in FIG. 16H. The sleeve or sheath 274 may be placed over a surface 254 of an expandable member of any of the types described elsewhere herein, typically a balloon, scaffold, or tubular elastic sleeve, so that the feature causes the outer surface of the sleeve to protrude radially outwardly as the expandable member is expanded. The sleeve provides an atraumatic surface or cover to the plaque disruption features 272.

Alternatively or in addition to use of an adhesive, welding, or the like, the stress-applying or plaque-disrupting features of the present invention, such as spherical features 252, may be immobilized on a surface of a substrate 254 using an elastic, constraining sleeve or sheath 276*a*-276*d*, as shown in FIGS. 17A to 17D. The sleeve conforms to the shape of the surface and the features 252 to hold and immobilize the features as the expandable member or other substrate is inflated or otherwise expanded from an initial narrow width or diameter configuration to a radially expanded or inflated configuration.

Figure 17A:
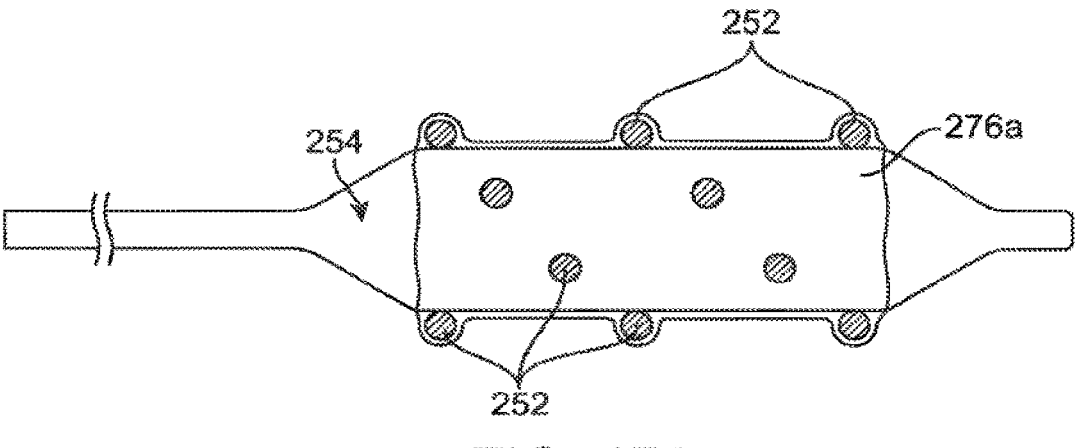
FIGS. 17A to 17D illustrate spherical plaque-disrupting features constrained or otherwise held on an outer surface of a balloon using an elastic sleeve.
Figure 17B:
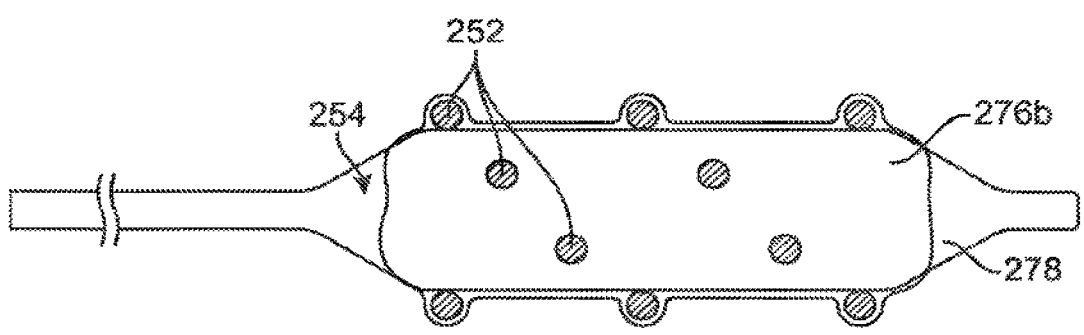
Figure 17C:
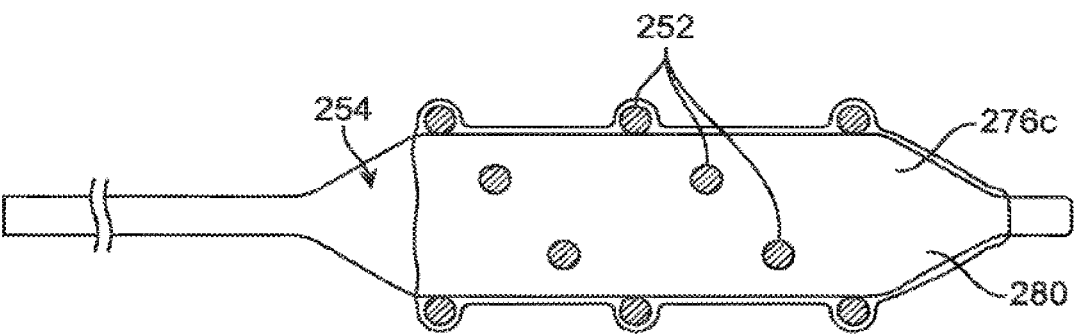
Figure 17D:
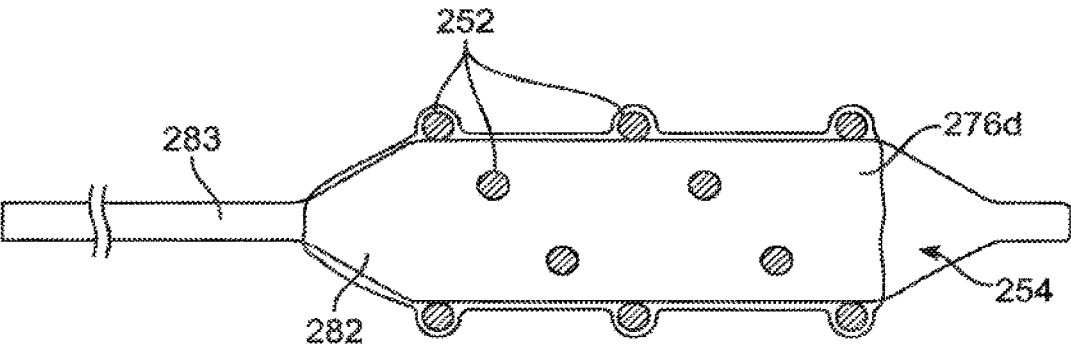

As shown in FIG. 17A, a sleeve 276*a* may be attached to a cylindrical working length of the balloon or other substrate. In other examples (not shown), a sleeve may be attached to one side only (proximal or distal) of the cylindrical working length of the balloon or other substrate. As shown in FIG. 17B, a sleeve 276*b* may be attached to a tapered/conical proximal portion and distal portion 278 of the expandable substrate 254. As shown in FIG. 17C, a sleeve 276*c* is attached at its distal end to a tapered/conical distal tip 280 of the expandable substrate 254. As shown in FIG. 17D, a proximal end 282 of sleeve 276*d* is attached to a proximal conical/tapered end of the expandable structure 254 or proximal shaft 283.

In other embodiments, the stress-applying and plaque-disrupting features 252 of the present invention may be placed on an inner surface of an expandable structure such as an inner surface of an elastic sleeve 290 or other expandable, cage or structure, as shown in FIGS. 18A to 18C. A folded or otherwise unexpanded balloon 292 is advanced into an interior of the sleeve 290, or the sleeve is advanced or retracted over the balloon, prior to inflation or expansion of the balloon, to center the balloon within the interior of the sleeve, as shown in FIG. 18B. The balloon 292 may be inflated causing the features 252 to partially or fully protrude radially outwardly through the sleeve, or balloon membrane, as shown in FIG. 18C.

Figures 2, 2H, 3, 4, 5, 6, 7, 8, 9, 10, 11, 12, 13, 14, 15, 16, 17, 18, 19, 20, 21:
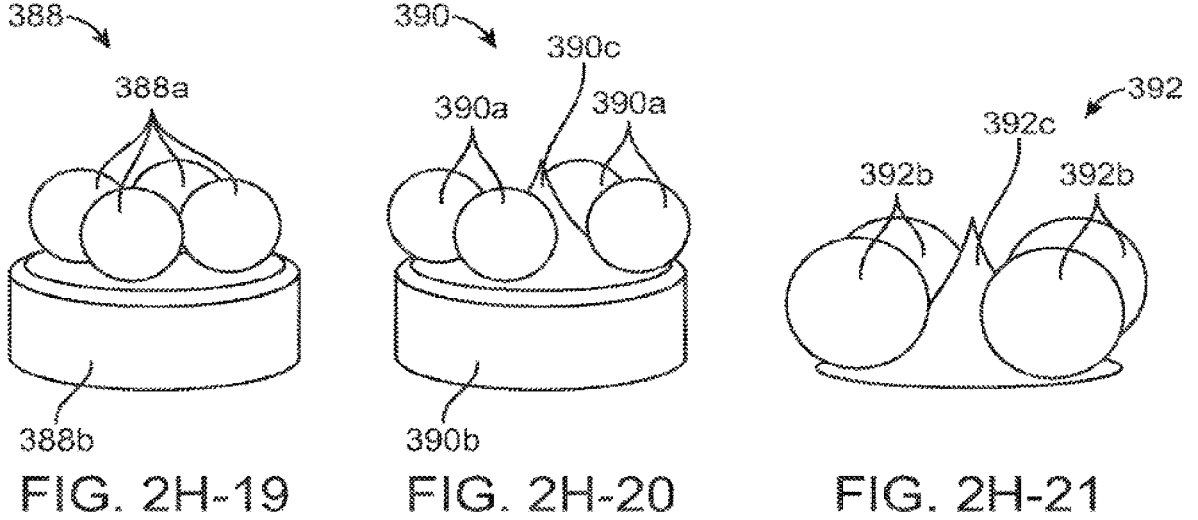

Referring now to FIGS. 19, 20A, and 20B, a drug delivery catheter 300 includes a balloon 302 having both a plurality of plaque-disrupting features 304 and a plurality of expandable ports 306 disposed over an exterior surface thereof. The balloon 302 will typically be elastic or semi-compliant, allowing the ports 306 to expand from a closed or substantially closed configuration, as shown in FIG. 20A, to an open or expanded configuration, as shown in FIG. 20B, in response to balloon inflation. The balloon 302 may be inflated with an inflation medium carrying a drug or other medicament introduced into an interior 308 of the balloon to effect both balloon expansion and release of the medicament medium through the ports 306 as they open in response to pressurization. The ports 306 will typically be configured to open in response to an internal pressure above a minimum threshold value, typically above 3 atm, 5 atm, or 7 atm.

Figures 21A, 21B, 21C, 21D:
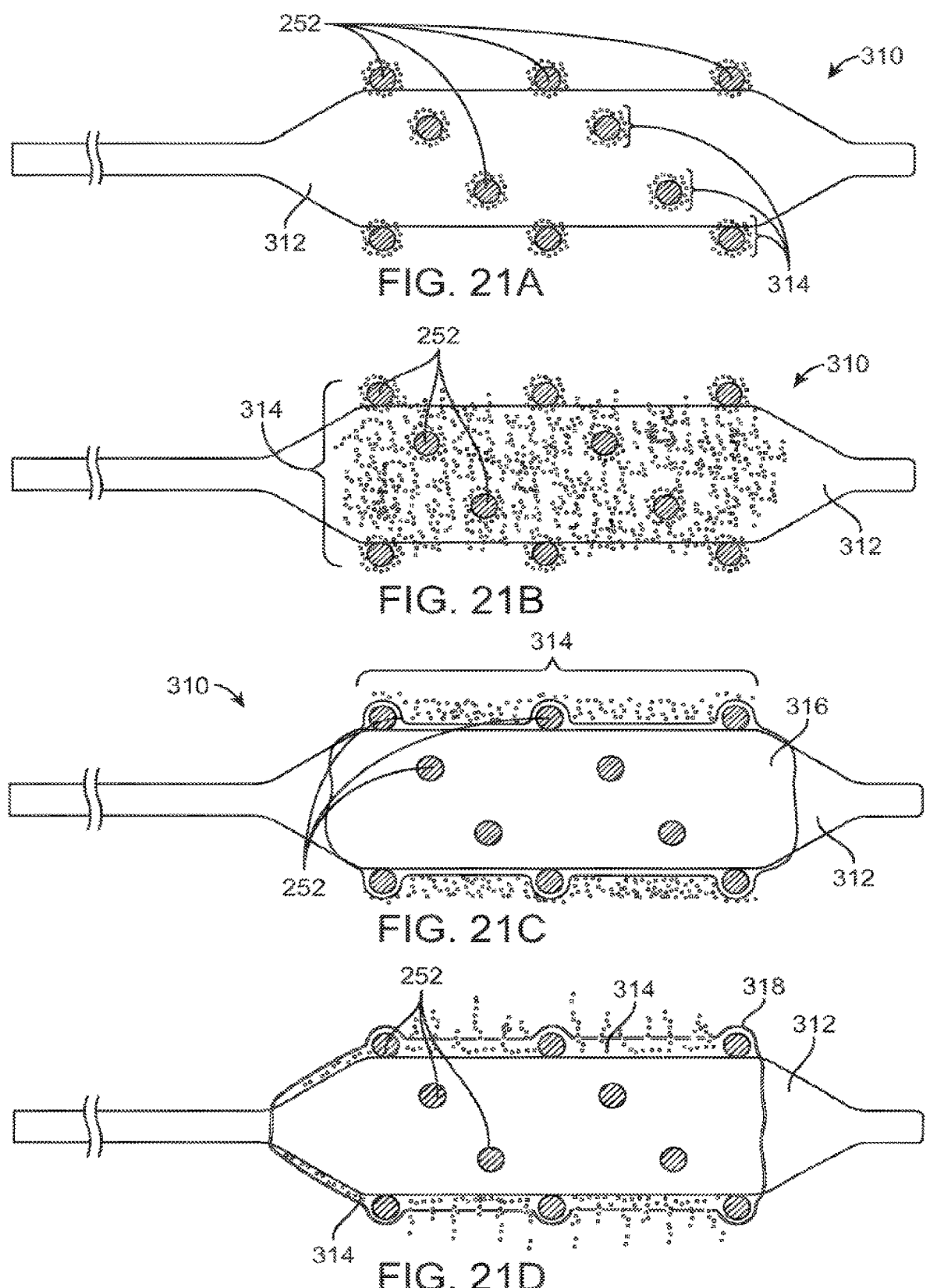
FIGS. 21A to 21D illustrate alternative structures and methods for the intravascular delivery of drugs using plaque disrupting features of the present invention. The structures of FIGS. 21C and 21D incorporate elastic sleeves.

Referring now to FIGS. 21A to 21D, drug delivery catheters 310 carrying the stress-applying and plaque-disrupting features 252 of the present invention and having alternative structures are illustrated. As shown in FIG. 21A, a drug delivery balloon 312 carries a plurality of features 252 which radially outwardly protrude from the balloon's outer surface. Drug particles 314 are coated over and/or incorporated within the features 252, e.g., the drug may be absorbed within porous features or may be held within a reservoir or hollow interior of the features. As shown in FIG. 21B, the drug may be coated over the surface and/or be releasably absorbed within the surface of either or both of the features 252 and the delivery balloon 312. As shown in FIG. 21C, the drug 314 may be coated over the surface and/or absorbed within an elastic membrane 316 which in turn is placed over balloon 312 in a manner similar to that described above with reference to FIG. 17A to 17C. In some instances, the drug 314 may be held within a porous, elastic membrane 318, as shown in FIG. 21D. In such instances, the drug 314 will be released through the porous or perforation in the membrane of elastic member 318 as the balloon 312 is expanded.

Figures 2, 2H, 3, 4, 5, 6, 7, 8, 9, 10, 11, 12, 13, 14, 15, 16, 17, 18, 19, 20, 21, 22:
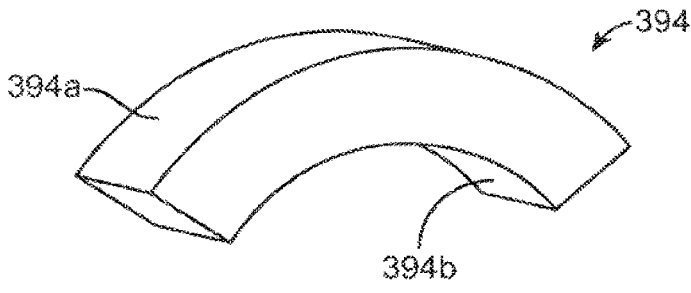

Referring now to FIG. 22, plaque-disrupting features 340 of the present invention may be placed on an exterior surface of a balloon-expandable scaffold or "cage" 342 of a type intended for temporary placement in a target vascular location for plaque-disrupting and subsequent removal. The cage may be formed from an elastic polymeric material, from an elastic metal such as nickel-titanium alloy, or from another material that expands and contracts when an expandable structure is expanded and deflated (or collapsed) inside the cage.

Figures 22, 23A, 23B:
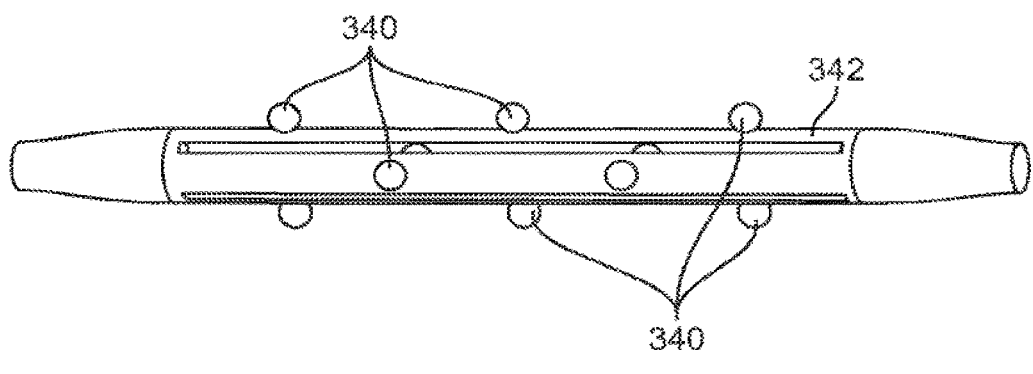

Referring now to FIG. 23A the expandable scaffold 342 of FIG. 22 has a central lumen or passage that may be placed over a balloon 342 (FIG. 23B) of a balloon catheter 344 prior to expansion of the balloon.

As shown in FIG. 23B the balloon 342 may be inflated to expand the expandable scaffold 342 to push the plaque-disrupting features 342 on the scaffold radially outwardly to engage plaque. The scaffold will be formed from an elastic material, usually an elastic metal such a nickel-titanium alloy, e.g., Nitinol® or other superelastic metal or polymer, so that it will open with the balloon when the balloon is inflated as well as close radially inwardly over the balloon as the balloon is deflated.

Figure 24:
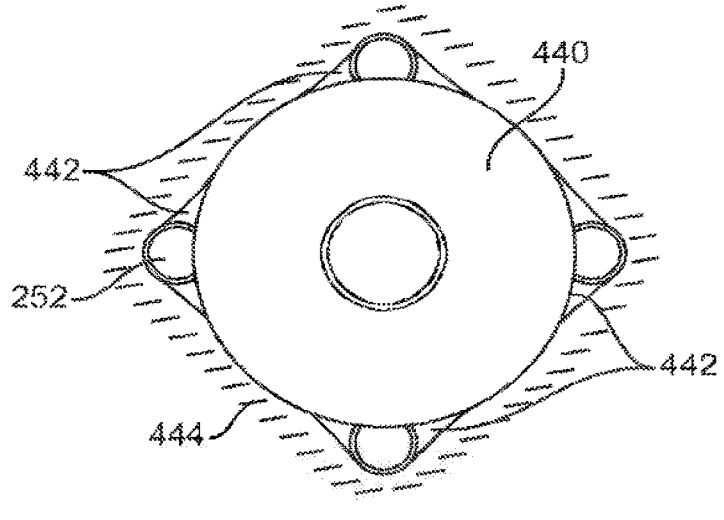
FIG. 24 is an end view an expandable structure, such as a balloon catheter, having features, such as metal spheres, contacting and/or expanding plaque tissue, showing spaces created for fluid and/or contrast material to pass through between an outer surface of the expanded structure and an inner surface of the vessel (or plaque) by the features such as metal spheres.
Figure 25:
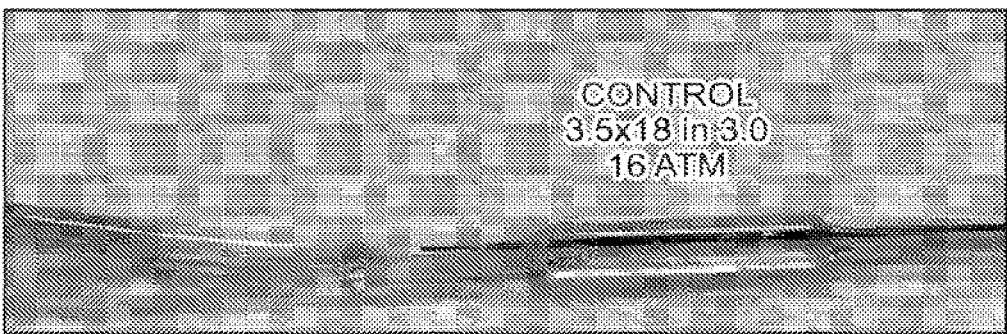
FIG. 25 shows a conventional balloon angioplasty catheter in a mock blood vessel (clear plastic tube) being perfused with a colored or contrast fluid where the flow is blocked by the expanded balloon.
Figure 26:
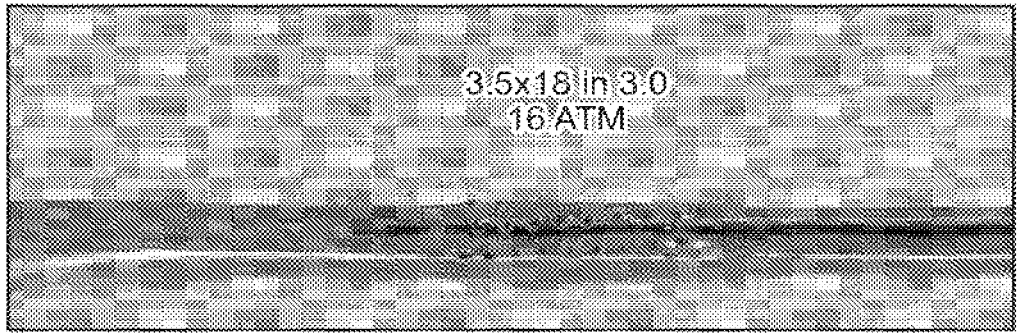
FIG. 26 a mock blood being perfused with a colored or contrast fluid where the flow bypasses the expanded balloon through spaces created between an outer surface of the expanded balloon and an inner surface of the mock blood vessel by the metal spheres or other features.

As shown in end view in FIG. 24, a balloon or other expanded member 440 has a plurality of discrete stress-applying or plaque-disrupting features 252 distributed over its circumference and length where the features act as spacers and are arranged in a pattern, density, size, shape, and/or footprint of the features create a plurality of potential pathways 442 along the length of the balloon between an outer surface of the expanded member and inner surface of the lesion 444, providing plurality of channels or gaps which permits the perfusion (flow) of blood, contrast media, drugs, and the like, past the inflated outer surface of the expanded member under expected vascular conditions. In a preferred example, the channels conduct fluid such as contrast fluid delivered at a pressure ranging from 1 psi to 10 psi, preferably at a pressure ranging from 1 psi to 5 psi, more preferably at a pressure ranging from 1 psi to 3 psi. In some instances, the channels may not allow the flow of blood or contrast media at physiologic pressure. In such circumstances, it may be necessary to pressurize the vessel or body lumen by from 1 psi to 3 psi above physiologic pressure. Compare FIG. 25 which shows how an inflated conventional balloon will block the flow of a colored medium in a mock vessel with FIG. 26 where the colored medium will flow past a balloon 440 having the surface features of the present invention.

In some instances, the spacer-features are configured or arranged to allow passage of contrast medium through channels around or adjacent to the features, and/or through holes (see FIGS. 24D, 24D-1, 24D-3, and 24D-3) in the features, at pressures ranging from 10 mmHg to 500 mmHg, preferably from 10 mm Hg to 200 mm Hg, more preferably from 10 mmHg, to 100 mmHg. Alternatively, the spacer-features may be configured to allow passage of fluid, contrast, and/or medicaments from 0.5 psi to 5 psi, preferably from 0.5 psi to 3 psi, more preferably from 0.5 psi to 2 psi, when the expandable structure is expanded to nominal expanded configuration or nominal diameter.

Figures 24C, 24D:
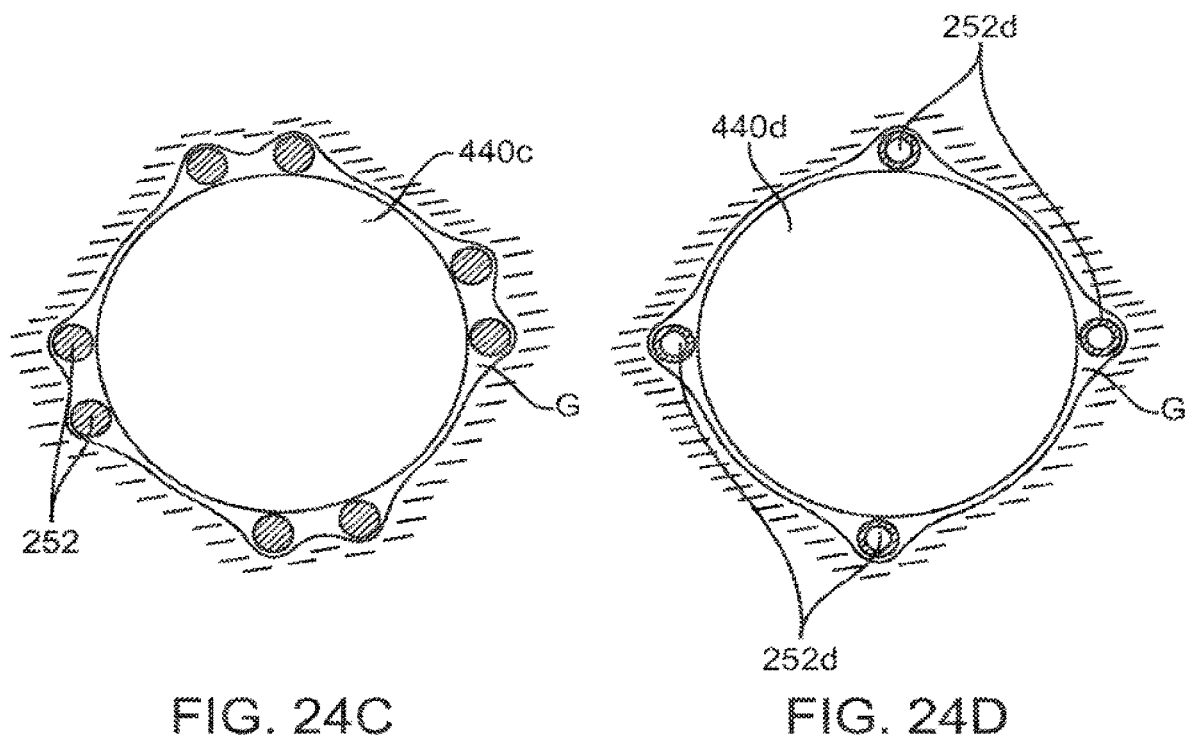
Figures 1, 24D:
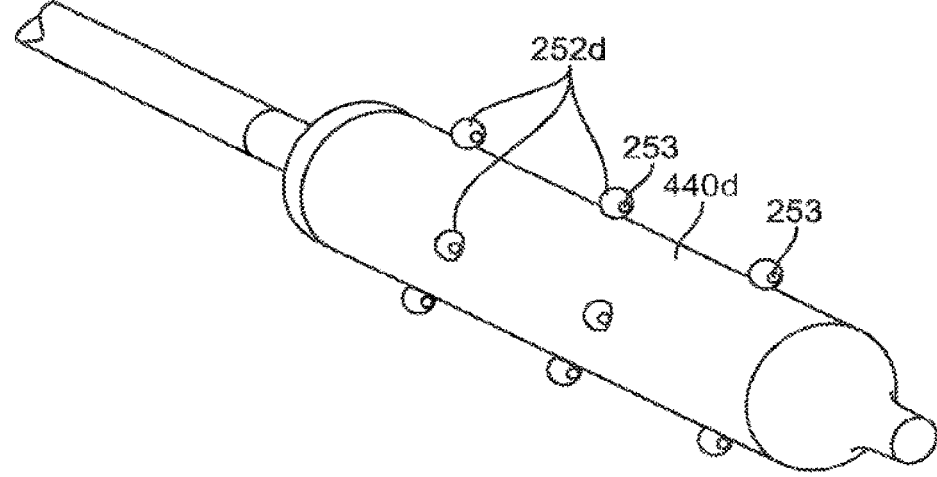
Figures 2, 24D:
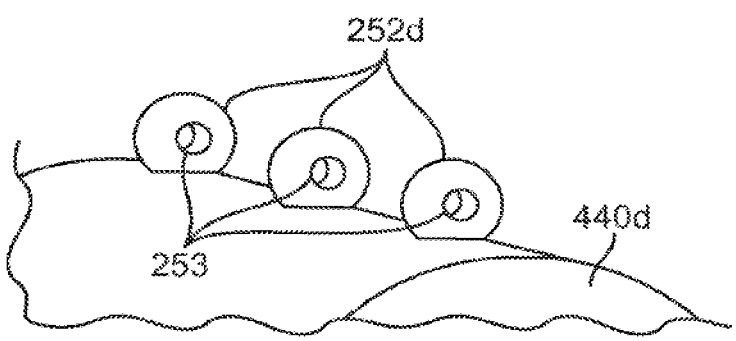
Figures 3, 24D:
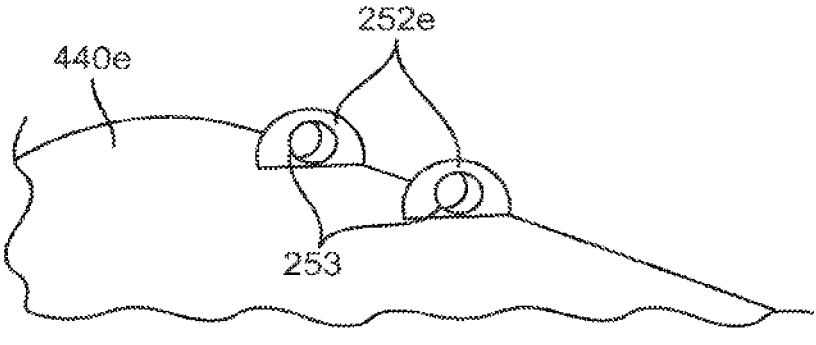

FIGS. 24A to 24D illustrates balloons 440a to 440d having different feature patterns to create bypass channels or gaps G according to the present invention. Such constructions are particularly advantageous when performing fluoroscopy or medication injection across an expanded member in I blood vessel or other lumen where contrast or a drug solution is injected into the vessel proximal to the expandable member at pressure above physiologic pressures, sufficient to allow the channels to conduct fluid across the axial length of the expanded structure. FIG. 24A shows a plurality of features configured to provide channels sufficient to allow contrast fluid bypass across the axial length of the expandable structure when the structure is in the expanded configuration such as an expanded (fully inflated balloon). FIG. 24B is another example of a dual adjacent feature along the circumference and/or axial length of the expandable structure to provide channels to conduct contrast fluid or medicaments across the axial length of the expandable structure when the structure is in the expanded configuration. FIG. 24C example shows another example of a plurality of features oriented to create channels (gaps) between the features in an axial direction and/or circumferential direction. FIG. 24D shows holes 253 (FIGS. 24D-1 and 24D-2) formed in the features oriented axially (shown) to allow contrast, fluid, and/or medicaments to bypass an expanded structure such as an expanded balloon.

FIGS. 24D-1 to 24D-3 illustrate features of the type illustrated in FIG. 24D having holes 253 through the features 252d which further promote perfusion of contrast media past balloons when inflated in the vasculature. As shown in FIGS. 24D-1 and 24D-2, spherical features 252d have through-holes 253 which further promote and allow the flow of contrast medium past the outer surface of the balloon 440d. Similarly, as shown in FIG. 24D-3, through holes 253 may be provided in hemispherical or other spacer-features 252e on the outer surface of a balloon 440e or other expandable structure. By arranging the spacer features along axial lines, elongate gaps are effectively created along axial paths on the balloon surface. Such axial paths, however, can sometimes be blocked by the spacer features 252d and 252e themselves. Such blockages can be lessened or eliminated by including through or bypass holes in the spacer features, preferably being axially aligned with the balloon.

It has been found that the use of spacers features (even without holes) can be effective in permitting contrast perfusion past balloons inflated at nominal pressures (typically 7 atm to 11 atm or higher) in the vasculature. In particular, the spacer features lower the pressure necessary to flow the contract past the balloon to assist in imaging the vasculature downstream of the balloon and reduce the back flow of contrast into the aorta or elsewhere. The inclusion of through holes has been found to lower the necessary contrast delivery pressure even further, further protecting the patient from excess delivery of toxic contrast media. Similarly, the inclusion of channels through the features as shown, for example, in FIGS. 2H-15 to 2H-21 would similarly promote contrast and blood perfusion in comparison to features lacking such internal flow paths.

Figure 27:
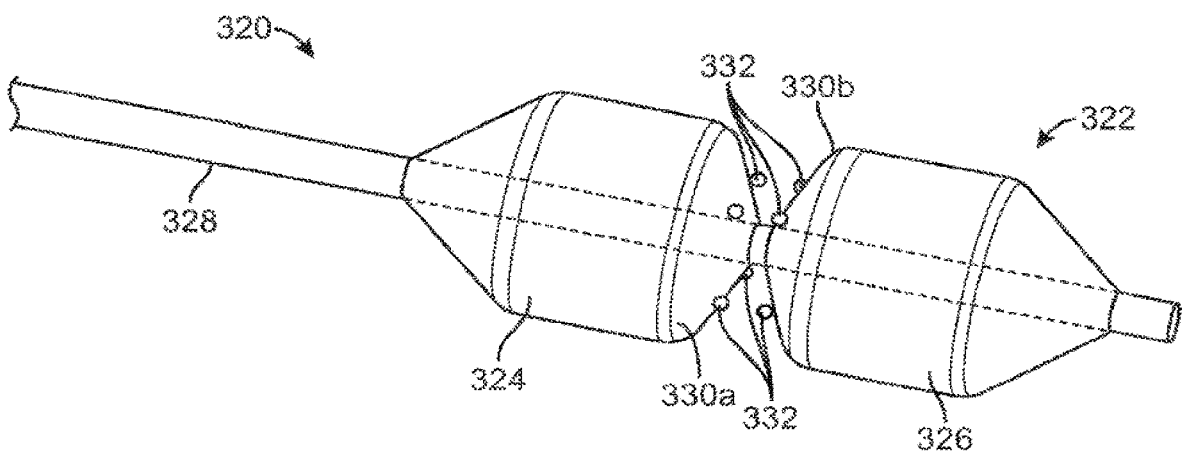

Referring now to FIG. 27, a valvuloplasty catheter 320 includes a segmented balloon structure 322 mounted on a distal end of a catheter shaft 328. The segmented balloon structure 322 includes both a proximal segment 324 and a distal segment 326, and the segments have opposed internal faces 330a and 330b. Each of these opposed surfaces has a plurality of plaque-disrupting features 332 distributed thereover. By inflating each of the segments and capturing calcified cardiac or other valve leaflets therebetween, the calcified plaque may be disrupted in order to improve valve function. In some instances, the segments 324 and 326 will be inflated simultaneously, while in other cases, one of the segments may be inflated initially, the inflated segment drawn against one side of the valve leaflets, and the other segment then inflated to effect disruption of the calcifications.

Figure 28:
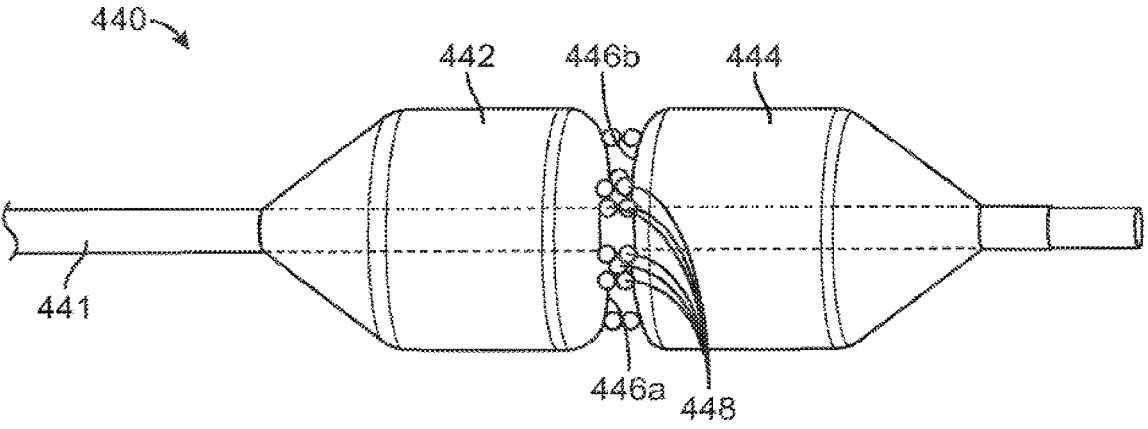

Valvuloplasty devices having other patterns of plaque-disrupting features are shown in FIGS. 28 to 31B. As shown in FIG. 28, a valvuloplasty catheter 440 includes a catheter shaft 441 having a proximal balloon 442 and a distal balloon 444 having opposed balloon surfaces 446a and 446b with flat faces each having a plurality of plaque-disrupting features 448 distributed thereover. Pairs of plaque-disrupting features 448 are arranged so that features on opposed services directly engage each other to apply force to a cardiac or other valve leaflet trapped therebetween.

Figure 29:
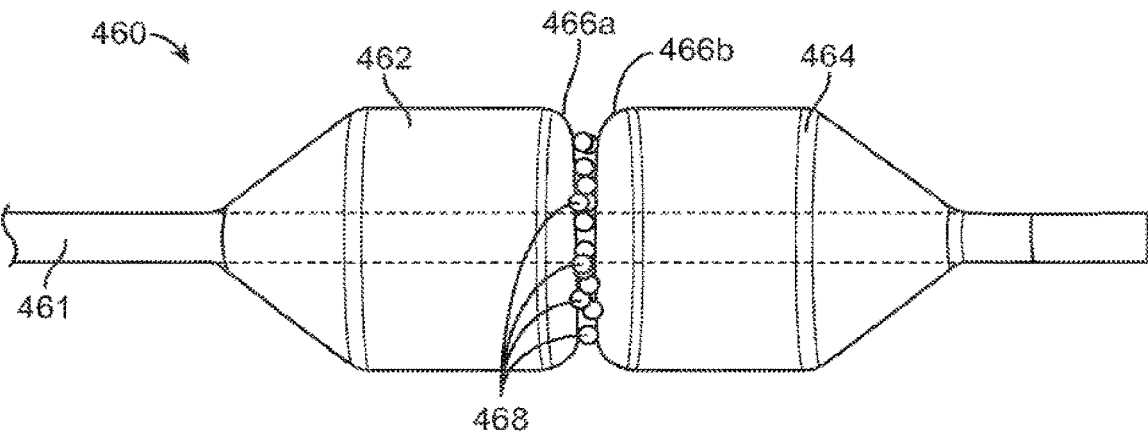

Valvuloplasty catheter 460 illustrated in FIG. 29 is similar to that illustrated in FIG. 28 having a proximal balloon 462 and a distal balloon 464 with opposed faces 466a and 466b thereon. The plaque disrupting features 468, however, are arranged so that they do not engage each other and instead directly engage the opposed balloon surface.

The balloons 322, 324, 442, 444, 462, and 464 may be fixedly attached to their respective catheter shafts so that the valve leaflets are entrapped only by inflating the balloons but will more often be slidably mounted relative to each other so that the balloons may be spaced-apart to capture the valve leaflets and then brought together to trap the valve leaflets and apply focused forces through the features to stress and disrupt calcifications and plaque on the leaflets.

As shown in FIGS. 30A and 30B, a valvuloplasty catheter 480 has a pair of nesting balloons 484 and 486 mounted on a shaft 482. Proximal balloon 484 has a concave conical surface 488a with a plurality of stress-applying features 486 distributed thereover. Distal balloon 486 has a convex conical surface 488b with a plurality of stress-applying features 489 distributed over its surface. A cardiac or other valve leaflet L may be captured between the balloon surfaces 488a and 488b when the surfaces are spaced apart, as shown in FIG. 30A, and plaque or other calcifications on the leaflets may be disrupted by drawing the distal and proximal balloons 486 and 484 together, as shown in FIG. 30B.

As shown in FIGS. 31A to 31B, valvuloplasty catheter 490 has a proximal balloon 494 and a distal balloon 496 mounted to slide relative to each other on a shaft 492. Opposed surfaces 498a and 498b of the balloons may be separated to capture a valve leaflet and brought together to engage stress-applying features 499 against the leaflets trapped therebetween. As can be seen, only surface 498b carries the stress-applying features and surface 498a is free from such features. The balloon 494 and 496 are shown to be conical which can be advantageous in accessing smaller regions.

The valvuloplasty balloon structures will typically be configured to compress or "sandwich" the valve leaflet(s) between the opposed surfaces. In some instances, the surfaces will be positioned by inflation only, i.e., the opposed surfaces will deploy and compress the leaflets as they reconfigure in response to inflation alone. In other instances, segments of the balloon structure having the opposed surfaces may be first deployed by inflation or otherwise and then drawn axially together to compress the valve leaflets between the opposed surfaces and engage the stress-applying features. The valvuloplasty balloon structures will typically be configured to compress or "sandwich" the valve leaflet(s) between the opposed surfaces of the balloon or expandable structure axial length.

Although certain embodiments or examples of the disclosure have been described in detail, variations and modifications will be apparent to those skilled in the art, including embodiments or examples that may not provide all the features and benefits described herein. It will be understood by those skilled in the art that the present disclosure extends beyond the specifically disclosed embodiments or examples to other alternative or additional examples or embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or sub-combinations of the specific features and aspects of the embodiments and examples may be made and still fall within the scope of the present disclosure. Accordingly, it should be understood that various features and aspects of the disclosed embodiments can be combined with or substituted for one another in order to form varying modes or examples of the present disclosure. Thus, it is intended that the scope of the present disclosure herein disclosed should not be limited by the particular disclosed embodiments or examples described above. For all of the embodiments and examples described above, the steps of any methods for example need not be performed sequentially.

What is claimed is:

1. An apparatus for treating calcification on a wall in a patient's body lumen, the apparatus comprising:
   a catheter including a catheter body having a proximal end and a distal segment;
   an expandable polymeric balloon disposed at the distal segment of the catheter body, the expandable polymeric balloon having an outer surface configured to be displaced radially outward toward an inner surface of the wall in the patient's body lumen; and
   a plurality of plaque-disrupting features distributed over the outer surface of the expandable polymeric balloon, wherein at least some of the plurality of plaque-disrupting features have an upper surface configured to fracture the calcification while reducing damage to the patient's body lumen when the expandable polymeric balloon is expanded within the patient's body lumen;
   wherein the at least some of the plurality of plaque-disrupting features comprise discrete bodies;
   wherein the at least some of the plaque-disrupting features comprise any one or any combination of a ball, a sphere, a partial sphere, a hemisphere, an ellipsoidal solid, or a dome; and wherein a bottom-most surface of each of the ball, the sphere, the partial sphere, the hemisphere, the ellipsoidal solid, or the dome is directly bonded to the outer surface of the expandable polymeric balloon.

2. The apparatus as in claim 1, wherein the at least some of the upper surfaces of the plurality of plaque-disrupting features comprise a convex rounded upper surface.

3. The apparatus as in claim 2, wherein the convex rounded upper surface of the at least some of the plurality of plaque-disrupting features has a radial height above the outer surface of the expandable polymeric balloon in a range from a minimum of 0.05 mm, 0.1 mm, 0.15 mm, 0.2 mm, or 0.25 mm to a maximum of 1 mm, 0.5 mm, 0.4 mm, 0.3 mm, or 0.25 mm, and a distribution density in a range from 0.1 to 5 features/mm$^2$ when the expandable polymeric balloon is expanded.

4. The apparatus as in claim 2, wherein the convex rounded upper surface comprises a single convex rounded upper surface.

5. The apparatus as in claim 1, wherein the at least some of the plurality of plaque-disrupting features have a lower portion disposed in an indentation on the outer surface of the expandable polymeric balloon.

6. The apparatus as in claim 1, wherein the at least some of the plurality of plaque-disrupting features comprise a sphere, partial sphere, or hemisphere.

7. The apparatus as in claim 1, wherein the discrete bodies comprise a metal or a metal alloy.

8. The apparatus as in claim 1, wherein at least a portion of the plurality of plaque-disrupting features have a footprint with a maximum width, diameter, or other lateral dimension of 4 mm or less.

9. The apparatus as in claim 1, wherein the at least some of the plurality of plaque-disrupting features comprise solid metal spheres, partial spheres, or hemispheres with flat or concave bottoms.

10. The apparatus as in claim 1, wherein bottoms of the at least some of the plurality of plaque-disrupting features are recessed along the outer surface of the expandable polymeric balloon.

11. The apparatus as in claim 1, wherein an encapsulation layer covers an entire working length of the outer surface of the expandable polymeric balloon.

12. The apparatus as in claim 1, wherein the at least some of the plurality of plaque-disrupting features are constrained over the outer surface of the expandable polymeric balloon by an elastic sleeve.

13. The apparatus as in claim 1, further comprising an encapsulation layer covering the upper surface of the at least some of the plurality of plaque-disrupting features and covering an entire working length of the outer surface of the expandable polymeric balloon.

14. The apparatus as in claim 1, wherein the at least some of the plurality of plaque-disrupting features, prior to bonding with the outer surface of the expandable polymeric balloon, are pre-coated with an adhesive, a polymeric material, a hydrophilic material or any combination thereof.

15. The apparatus as in claim 1, wherein the plurality of plaque-disrupting features cover a working length of the outer surface of the expandable polymeric balloon.

16. The apparatus as in claim 1, wherein the plurality of plaque-disrupting features cover an entire length of the outer surface of the expandable polymeric balloon.

17. The apparatus as in claim 1, further comprising an encapsulation layer extending beneath the at least some of the plurality of plaque-disrupting features and covering an entire working length of the outer surface of the expandable polymeric balloon.

18. The apparatus as in claim 17, wherein the encapsulation layer comprises at least one of an adhesive, a polymer, or a hydrophilic material.

19. The apparatus as in claim 17, wherein the encapsulation layer comprises a polymer selected from the group consisting of thermoplastic fluoropolymers, butyl methacrylates, and thermoplastic polyesters.

20. The apparatus as in claim 17, wherein the encapsulation layer is applied over the outer surface of the expandable polymeric balloon and the plurality of plaque-disrupting features by any one of coating, direct fluid application, laminating, or fusing.

21. The apparatus as in claim 17, wherein the encapsulation layer has a thickness in a range from 0.01 mm to 0.1 mm.

22. The apparatus as in claim 17, wherein the at least some of the plurality of plaque-disrupting features, prior to bonding with the outer surface of the expandable polymeric balloon, are pre-coated with an adhesive, a polymeric material, a hydrophilic material or any combination thereof.

23. The apparatus of claim 17, wherein the plurality of plaque-disrupting features are directly bonded to the outer surface of the expandable polymeric balloon through an adhesive, through the encapsulation layer, or both.

24. The apparatus as in claim 23, wherein the at least some of the plurality of plaque-disrupting features are immobilized solely by one or more adhesives, the encapsulation layer, or both.

25. The apparatus as in claim 23, wherein the encapsulation layer comprises a polymer selected from the group consisting of thermoplastic fluoropolymers, butyl methacrylates, and thermoplastic polyesters.

26. The apparatus as in claim 23, wherein the encapsulation layer is applied over the outer surface of the expandable polymeric balloon and the plurality of plaque-disrupting features by any one of coating, direct fluid application, laminating, or fusing.

* * * * *